US009090570B2

(12) United States Patent
Sun et al.

(10) Patent No.: US 9,090,570 B2
(45) Date of Patent: Jul. 28, 2015

(54) COMPOUNDS FOR INFLAMMATION AND IMMUNE-RELATED USES

(71) Applicant: Synta Pharmaceuticals Corp., Lexington, MA (US)

(72) Inventors: Lijun Sun, Harvard, MA (US); Shoujun Chen, Bedford, MA (US); Jun Jiang, Westwood, MA (US); Yu Xie, Natick, MA (US); Chih-Yi Yu, Malden, MA (US)

(*) Notice: Subject to any disclaimer, the term of this patent is extended or adjusted under 35 U.S.C. 154(b) by 0 days.

(21) Appl. No.: 13/948,541

(22) Filed: Jul. 23, 2013

(65) Prior Publication Data

US 2013/0309272 A1 Nov. 21, 2013

Related U.S. Application Data

(62) Division of application No. 11/340,184, filed on Jan. 25, 2006, now Pat. No. 8,518,950.

(60) Provisional application No. 60/646,683, filed on Jan. 25, 2005.

(51) Int. Cl.

| | |
|---|---|
| *A61K 31/50* | (2006.01) |
| *A61K 31/497* | (2006.01) |
| *A61K 31/4965* | (2006.01) |
| *A61K 31/495* | (2006.01) |
| *A61K 31/505* | (2006.01) |
| *C07D 241/20* | (2006.01) |
| *C07D 401/12* | (2006.01) |
| *C07D 401/14* | (2006.01) |
| *C07D 403/10* | (2006.01) |
| *C07D 405/14* | (2006.01) |
| *C07D 413/10* | (2006.01) |
| *C07D 413/14* | (2006.01) |
| *C07D 417/14* | (2006.01) |
| *A61P 37/06* | (2006.01) |
| *A61P 17/06* | (2006.01) |
| *A61P 7/06* | (2006.01) |
| *A61P 1/04* | (2006.01) |
| *A61P 19/02* | (2006.01) |

(52) U.S. Cl.
CPC ............ *C07D 241/20* (2013.01); *A61K 31/495* (2013.01); *A61K 31/497* (2013.01); *A61K 31/4965* (2013.01); *A61K 31/50* (2013.01); *A61K 31/505* (2013.01); *C07D 401/12* (2013.01); *C07D 401/14* (2013.01); *C07D 403/10* (2013.01); *C07D 405/14* (2013.01); *C07D 413/10* (2013.01); *C07D 413/14* (2013.01); *C07D 417/14* (2013.01)

(58) Field of Classification Search
CPC .. C07D 401/12; C07D 401/14; C07D 401/04; C07D 241/20; C07D 401/10
USPC .............................. 514/255.06; 544/336, 405
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |

(Continued)

FOREIGN PATENT DOCUMENTS

| | | | |
|---|---|---|---|
| EP | 1 249 233 | A1 | 10/2002 |
| EP | 1 553 089 | A1 | 7/2005 |

(Continued)

OTHER PUBLICATIONS

Extended European Search Reprot for EP 1848435 mailed Aug. 26, 2010.
[No Author Listed] CAS Registry No. 777860-87-4. Nov. 10, 2004. 1 page.
Al-Dabbagh et al., Species differences in oxidative drug metabolism: some basic considerations. Arch Toxicol Suppl. 1984;7:219-31.
Bratusek et al., Transformations of (Z)-benzoylamino-4-dimethylamino-2-oxo-butene and Є-3-benzoylamino-4-cyano-2-oxo-3-butene into pyrimidine, pyrazole and isoxazole derivatives. ARKIVOC Journal. 2003;5:77-86.

(Continued)

*Primary Examiner* — Susanna Moore
(74) *Attorney, Agent, or Firm* — Krieg DeVault, LLP

(57) ABSTRACT

The invention relates to compounds of structural formula (I) and structural formula (VI):

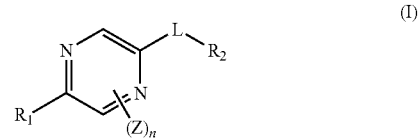

or a pharmaceutically acceptable salt, solvate, clathrate, or prodrug thereof, wherein R, $R_1$, $R_2$, Z, L, and n are defined herein. These compounds are useful as immunosuppressive agents and for treating and preventing inflammatory conditions, allergic disorders, and immune disorders.

23 Claims, No Drawings

(56) References Cited

U.S. PATENT DOCUMENTS

| | | | |
|---|---|---|---|
| 5,733,566 | A | 3/1998 | Lewis |
| 6,274,171 | B1 | 8/2001 | Sherman et al. |
| 6,599,905 | B2 | 7/2003 | Cox et al. |
| 6,649,624 | B2 | 11/2003 | Fukami et al. |
| 6,699,891 | B1 | 3/2004 | Kawanishi et al. |
| 6,803,372 | B2 | 10/2004 | Fukami et al. |
| 6,924,291 | B2 | 8/2005 | Song et al. |
| 8,518,950 | B2 | 8/2013 | Sun et al. |
| 2004/0048991 | A1 | 3/2004 | Kato et al. |
| 2004/0110802 | A1 | 6/2004 | Thorarensen et al. |
| 2005/0107436 | A1 | 5/2005 | Xie et al. |
| 2005/0148633 | A1 | 7/2005 | Xie et al. |
| 2006/0173006 | A1 | 8/2006 | Sun et al. |
| 2006/0173021 | A1 | 8/2006 | Sun et al. |
| 2006/0199845 | A1 | 9/2006 | Sun et al. |
| 2007/0249609 | A1 | 10/2007 | Chen et al. |
| 2007/0249661 | A1 | 10/2007 | Chen et al. |

FOREIGN PATENT DOCUMENTS

| | | | |
|---|---|---|---|
| JP | 11240832 | A | 9/1999 |
| JP | 2003-104884 | A | 4/2003 |
| JP | 2002249473 | A | 9/2009 |
| WO | WO 01/14376 | A1 | 3/2001 |
| WO | WO 01/37826 | A1 | 5/2001 |
| WO | WO 03/032970 | A1 | 4/2003 |
| WO | WO 03/033482 | A1 | 4/2003 |
| WO | WO 03/051870 | A1 | 6/2003 |
| WO | WO 03/076440 | A1 | 9/2003 |
| WO | WO 03/076443 | | 9/2003 |
| WO | WO 2004/009015 | A2 | 1/2004 |
| WO | WO 2004/011440 | A1 | 2/2004 |
| WO | WO 2004/056774 | A2 | 7/2004 |
| WO | WO 2004/089919 | A1 | 10/2004 |
| WO | WO 2004/110375 | A2 | 12/2004 |
| WO | WO 2005/000217 | A2 | 1/2005 |
| WO | WO 2005/003101 | A2 | 1/2005 |
| WO | WO 2005/018624 | A2 | 3/2005 |
| WO | WO 2005/090340 | A1 | 9/2005 |
| WO | WO 2006/066173 | A2 | 6/2006 |
| WO | WO 2007/017096 | A1 | 2/2007 |
| WO | WO 2007/056341 | A1 | 5/2007 |
| WO | WO 2007/067836 | A2 | 6/2007 |
| WO | WO 2007/084455 | A1 | 7/2007 |
| WO | WO 2007/089335 | A2 | 8/2007 |

OTHER PUBLICATIONS

Bundgaard, Design of Prodrugs. Elsevier Science Publishers. 1985. 1 page.

Gavezzotti et al., Are crystal structures predictable? Accounts of Chemical Research. 1994;27:309-14.

Hirano et al., Chemiluminescence of coelenterazine analogues—structures of emitting species. Tetrahedron Letters. 1992;33(39):5771-4.

Issac, Synthesis, reactions, and spectroscopy of 3-benzoyl-6-phenylpyridazines of expected biological activity. Verlag der Zeitschrift fur Naturforschung. 1999;54(b);1048-54.

Jeanjot et al., N-(Alkyl)-2-amino-1,4-pyrazine Derivatives: Synthesis and Antioxidative Properties of 3- and 3,5-p-Hydroxyphenyl-Substituted Compounds. Synthesis. 2003;4:513-22.

Lewis, Calcium oscillations in T-cells: mechanisms and consequences for gene expression. Biochem Soc Trans. Oct. 2003;31(Pt 5):925-9.

McCapra et al., Bioluminescence of coelenterates: chemiluminescent model compounds. J.C.S. Chem. Comm 1973:407-8.

Pinto et al., Discovery of 1-[3-(aminomethyl)phenyl]-N-3-fluoro-2'-(methylsulfonyl)-[1,1'-biphenyl]-4-yl]-3-(trifluoromethyl)-1H-pyrazole-5-carboxamide (DPC423), a highly potent, selective, and orally bioavailable inhibitor of blood coagulation factor Xa. J Med Chem. Feb. 15, 2001;44(4):566-78.

Silverman, The organic chemistry of drug decision and action. Academic Press, Inc. 1992. pp. 352-400.

Vippagunta et al., Crystalline solids. Adv Drug Deliv Rev. May 16, 2001;48(1):3-26.

International Search Report and Written Opinion for PCT/US2006/002874 mailed Apr. 10, 2007.

International Preliminary Report on Patentability for PCT/US2006/002874 mailed Aug. 9, 2007.

Japanese Office Action in corresponding Japanese patent application (i.e., JP2014-177307), transmitted May 19, 2015 (9 pages with English translation).

COMPOUNDS FOR INFLAMMATION AND IMMUNE-RELATED USES

RELATED APPLICATIONS

This application is a divisional of U.S. patent application Ser. No. 11/340,184, filed on Jan. 25, 2006, now U.S. Pat. No. 8,518,950, issued Aug. 27, 2013, which claims the benefit of U.S. provisional application No. 60/646,683, filed on Jan. 25, 2005. The contents of each of these applications are incorporated herein by reference in their entireties for all purposes.

FIELD OF THE INVENTION

This invention relates to biologically active chemical compounds, namely pyrazinyl, pyrimidinyl and pyridazinyl derivatives that may be used for immunosuppression or to treat or prevent inflammatory conditions, allergic disorders and immune disorders.

BACKGROUND OF THE INVENTION

Inflammation is a mechanism that protects mammals from invading pathogens. However, while transient inflammation is necessary to protect a mammal from infection, uncontrolled inflammation causes tissue damage and is the underlying cause of many illnesses. Inflammation is typically initiated by binding of an antigen to T-cell antigen receptor. Antigen binding by a T-cell initiates calcium influx into the cell via calcium ion channels, such as $Ca^{2+}$-release-activated $Ca^{2+}$ channels (CRAC). Calcium ion influx in turn initiates a signaling cascade that leads to activation of these cells and an inflammatory response characterized by cytokine production.

Interleukin 2 (IL-2) is a cytokine that is secreted by T cells in response to calcium ion influx into the cell. IL-2 modulates immunological effects on many cells of the immune system. For example, it is a potent T cell mitogen that is required for T cell proliferation, promoting their progression from G1 to S phase of the cell cycle; it stimulates the growth of NK cells; and it acts as a growth factor to B cells and stimulates antibody synthesis.

IL-2, although useful in the immune response, can cause a variety of problems. IL-2 damages the blood-brain barrier and the endothelium of brain vessels. These effects may be the underlying causes of neuropsychiatric side effects observed under IL-2 therapy, e.g. fatigue, disorientation and depression. It also alters the electrophysiological behaviour of neurons.

Due to its effects on both T and B cells, IL-2 is a major central regulator of immune responses. It plays a role in inflammatory reactions, tumour surveillance, and hematopoiesis. It also affects the production of other cytokines, inducing IL-1, TNF-α and TNF-β secretion, as well as stimulating the synthesis of IFN-γ in peripheral leukocytes.

T cells that are unable to produce IL-2 become inactive (anergic). This renders them potentially inert to any antigenic stimulation they might receive in the future. As a result, agents which inhibit IL-2 production can be used for immunosupression or to treat or prevent inflammation and immune disorders. This approach has been clinically validated with immunosuppressive drugs such as cyclosporin, FK506, and RS61443. Despite this proof of concept, agents that inhibit IL-2 production remain far from ideal. Among other problems, efficacy limitations and unwanted side effects (including dose-dependant nephrotoxicity and hypertension) hinder their use.

Over production of proinflammatory cytokines other than IL-2 has also been implicated in many autoimmune diseases. For example, Interleukin 5 (IL-5), a cytokine that increases the production of eosinophils, is increased in asthma. Overproduction of IL-5 is associated with accumulation of eosinophils in the asthmatic bronchial mucosa, a hall mark of allergic inflammation. Thus, patients with asthma and other inflammatory disorders involving the accumulation of eosinophils would benefit from the development of new drugs that inhibit the production of IL-5.

Interleukin 4 (IL-4) and interleukin 13 (IL-13) have been identified as mediators of the hypercontractility of smooth muscle found in inflammatory bowel disease and asthma. Thus, patients with athsma and inflammatory bowel disease would benefit from the development of new drugs that inhibit IL-4 and IL-13 production.

Granulocyte macrophage-colony stimulating factor (GM-CSF) is a regulator of maturation of granulocyte and macrophage lineage population and has been implicated as a key factor in inflammatory and autoimmune diseases. Anti-GM-CSF antibody blockade has been shown to ameliorate autoimmune disease. Thus, development of new drugs that inhibit the production of GM-CSF would be beneficial to patients with an inflammatory or autoimmune disease.

There is a continuing need for new drugs which overcome one or more of the shortcomings of drugs currently used for immunosuppression or in the treatment or prevention of inflammatory disorders, allergic disorders and autoimmune disorders. Desirable properties of new drugs include efficacy against diseases or disorders that are currently untreatable or poorly treatable, new mechanism of action, oral bioavailability and/or reduced side effects.

SUMMARY OF THE INVENTION

This invention meets the above-mentioned needs by providing certain pyrazinyl and pyridazinyl derivatives that inhibit the activity of CRAC ion channels and inhibit the production of IL-2, IL-4, IL-5, IL-13, GM-CSF, TNF-α, and IFNγ. These compounds are particularly useful for immunosuppression and/or to treat or prevent inflammatory conditions, allergic disorders and immune disorders.

In one embodiment, the invention relates to compounds of formula (I):

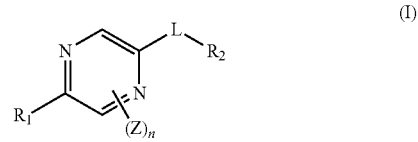

or a pharmaceutically acceptable salt, solvate, clathrate, or prodrug thereof, wherein:

L is a linker selected from the group consisting of —NRCH₂—, —CH₂NR—, —C(O)—, —NR—C(O)—, —C(O)—NR—, —C(S)—, —NR—C(S)—, —C(S)—NR—;

each Z is independently selected from the group consisting of a lower alkyl, a lower haloalkyl, a halo, a lower alkoxy, a lower alkyl sufanyl, cyano, nitro, or lower haloalkoxy;

R, for each occurrence is independently selected from —H, an alkyl, —C(O)R₅, or —C(O)OR₅;

R₁ is an optionally substituted aryl or an optionally substituted heteroaryl;

R$_2$ is an optionally substituted cycloalkyl, an optionally substituted cycloalkenyl, an optionally substituted aryl, or an optionally substituted heteroaryl;

R$_5$, for each occurrence, is independently, H, an alkyl, a cycloalkyl, a heterocyclyl, an aryl, a heteroaryl, an aralkyl, or a heteraralkyl; and n is 0, 1 or 2.

In another embodiment, the invention relates to compounds of formula (V):

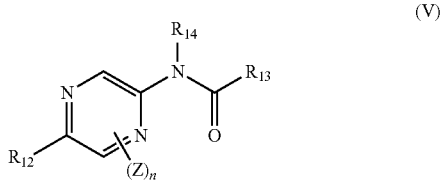

or a pharmaceutically acceptable salt, solvate, clathrate, or prodrug thereof, wherein:

R$_{12}$ is an aryl or a heteroaryl, wherein the aryl and heteroaryl are optionally substituted with one or more substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a halo, cyano, nitro, —OR$_{17}$, —SR$_{17}$, —S(O)$_p$R$_{17}$, —S(O)$_p$OR$_{17}$, —OS(O)$_p$R$_{17}$, —OS(O)$_p$OR$_{17}$, —NR$_{17}$S(O)$_p$R$_{17}$, —S(O)$_p$NR$_{15}$R$_{16}$, —NR$_{15}$R$_{16}$, —C(X$_3$)R$_{17}$, —C(X$_3$)OR$_{17}$, —C(X$_3$)SR$_{17}$, —C(X$_3$)NR$_{15}$R$_{16}$, —NR$_{17}$C(X$_3$)R$_{18}$, —NR$_{17}$C(X$_3$)OR$_{18}$, —NR$_{17}$C(X$_3$)SR$_{18}$, —NR$_{17}$C(X$_3$)NR$_{15}$R$_{16}$, —OC(X$_3$)R$_{17}$, —OC(X$_3$)OR$_{17}$, —OC(X$_3$)SR$_{17}$, —SC(X$_3$)OR$_{17}$, —SC(X$_3$)SR$_{17}$, —OC(X$_3$)NR$_{15}$R$_{16}$, —SC(X$_3$)NR$_{15}$R$_{16}$, —P(X$_4$)(X$_5$R$_{17}$)$_2$, —X$_5$P(X$_4$)(X$_5$R$_{17}$)$_2$, —P(X$_4$)(R$_{17}$)$_2$, —P(X$_4$)(R$_{17}$)(X$_5$R$_{17}$);

R$_{13}$ is a cycloalkyl, a cycloalkenyl, an aryl, or a heteroaryl, wherein the cycloalkyl, cycloalkenyl, aryl, or heteroaryl are optionally substituted with one or more substituents selected from the group consisting of an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted aralkyl, or an optionally substituted heteraralkyl, a halo, cyano, nitro, a haloalkyl, —OR$_{17}$, —SR$_{17}$, —S(O)$_p$R$_{17}$, —S(O)$_p$OR$_{17}$, —OS(O)$_p$R$_{17}$, —OS(O)$_p$OR$_{17}$, —S(O)$_p$NR$_{15}$R$_{16}$, —NR$_{15}$R$_{16}$, —C(X$_3$)R$_{17}$, —C(X$_3$)OR$_{17}$, —C(X$_3$)SR$_{17}$, —C(X$_3$)NR$_{15}$R$_{16}$, —NR$_{17}$C(X$_3$)R$_{18}$, —NR$_{17}$C(X$_3$)OR$_{18}$, —NR$_{17}$C(X$_3$)SR$_{18}$, —NR$_{17}$C(X$_3$)NR$_{15}$R$_{16}$, —OC(X$_3$)R$_{17}$, —OC(X$_3$)OR$_{17}$, —OC(X$_3$)SR$_{17}$, —SC(X$_3$)OR$_{17}$, —SC(X$_3$)SR$_{17}$, —OC(X$_3$)NR$_{15}$R$_{16}$, —SC(X$_3$)NR$_{15}$R$_{16}$, —P(X$_4$)(X$_5$R$_{17}$)$_2$, —X$_5$P(X$_4$)(X$_5$R$_{17}$)$_2$, —P(X$_4$)(R$_{17}$)$_2$, —P(X$_4$)(R$_{17}$)(X$_5$R$_{17}$);

R$_{14}$, for each occurrence is independently selected from —H, an alkyl, —C(O)R$_{20}$, or —C(O)OR$_{20}$;

R$_{15}$ and R$_{16}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{15}$ and R$_{16}$ taken together with the nitrogen to which they are attached are an optionally substituted heterocyclyl or optionally substituted heteroaryl;

R$_{17}$ and R$_{18}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{19}$, for each occurrence, is independently —H, a halo, an alkyl, —OR$_{17}$, —NR$_{15}$R$_{16}$, —C(O)R$_{17}$, —C(O)OR$_{17}$, or —C(O)NR$_{15}$R$_{16}$;

R$_{20}$, for each occurrence, is independently, H or an alkyl;

X$_3$ is =O, =S, or =N—R$_{19}$;

X$_4$ is =O or =S;

X$_5$ is —O— or —S—;

p is 1 or 2; and

Z and n are defined as for formula (I).

In another embodiment, the invention relates to compounds of formula (VI):

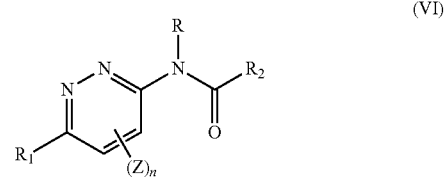

or a pharmaceutically acceptable salt, solvate, clathrate, or prodrug thereof, wherein:

R, R$_1$, R$_2$, Z and n are defined as for formula (I).

In another embodiment, the invention relates to compounds of formula (IX):

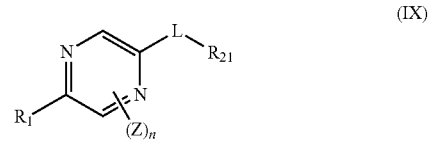

or a pharmaceutically acceptable salt, solvate, clathrate, or prodrug thereof, wherein:

R$_{21}$ is an alkyl which is optionally substituted with one or more substituents selected from the group consisting of an optionally substituted alkynyl, an optionally substituted cycloalkyl, an optionally substituted cycloalkenyl, an optionally substituted aryl, an optionally substituted heteroaryl, an optionally substituted aralkyl, an optionally substituted heteraralkyl, a halo, cyano, nitro, a haloalkyl, —OR$_{17}$, —SR$_{17}$, —S(O)$_p$R$_{17}$, —S(O)$_p$OR$_{17}$, —OS(O)$_p$R$_{17}$, —OS(O)$_p$OR$_{17}$, —S(O)$_p$NR$_{15}$R$_{16}$, —NR$_{15}$R$_{16}$, —C(X$_3$)R$_{17}$, —C(X$_3$)OR$_{17}$, —C(X$_3$)SR$_{17}$, —C(X$_3$)NR$_{15}$R$_{16}$, —NR$_{17}$C(X$_3$)R$_{18}$, —NR$_{17}$C(X$_3$)OR$_{18}$, —NR$_{17}$C(X$_3$)SR$_{18}$, —NR$_{17}$C(X$_3$)NR$_{15}$R$_{16}$, —OC(X$_3$)R$_{17}$, —OC(X$_3$)OR$_{17}$, —OC(X$_3$)SR$_{17}$, —SC(X$_3$)OR$_{17}$, —SC(X$_3$)SR$_{17}$, —OC(X$_3$)NR$_{15}$R$_{16}$, —SC $(X_3)NR_{15}R_{16}$, $-P(X_4)(X_5R_{17})_2$, $-X_5P(X_4)(X_5R_{17})_2$, $-P(X_4)(R_{17})_2$, $-P(X_4)(R_{17})(X_5R_{17})$;

$R_1$, Z and n are defined as for formula (I); and $R_{15}$, $R_{16}$, $R_{17}$, $R_{18}$, $X_3$, $X_4$, $X_5$, and p are defined as for formula (V).

In another embodiment, the invention relates to compounds of formula (XII):

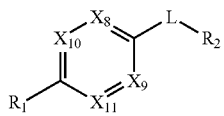

(XII)

or a pharmaceutically acceptable salt, solvate, clathrate, or prodrug thereof, wherein:

$X_8$ and $X_9$ are N and $X_{10}$ and $X_{11}$ are CH or CZ; or $X_{10}$ and $X_{11}$ are N and $X_8$ and $X_9$ are CH or CZ;

L, Z, $R_1$, and $R_2$ are defined as for formula (I).

A compound of the invention or a pharmaceutically acceptable salt, solvate, clathrate, or prodrug thereof is particularly useful inhibiting immune cell (e.g., T-cells and/or B-cells) activation (e.g., activation in response to an antigen). In particular, a compound of the invention or a pharmaceutically acceptable salt, solvate, clathrate, or prodrug thereof can inhibit the production of certain cytokines that regulate immune cell activation. For example, a compound of the invention or a pharmaceutically acceptable salt, solvate, clathrate, or prodrug thereof can inhibit the production of IL-2, IL-4, IL-5, IL-13, GM-CSF, TNF-α, INF-γ or combinations thereof. Moreover, a compound of the invention or a pharmaceutically acceptable salt, solvate, clathrate, or prodrug thereof can modulate the activity of one or more ion channel involved in activation of immune cells, such as CRAC ion channels.

In one embodiment, compounds of the invention or a pharmaceutically acceptable salt, solvate, clathrate, or prodrug thereof are particularly useful for inhibiting mast cell degranulation. Mast cell degranulation has been implicated in allergic reactions.

A compound of the invention or a pharmaceutically acceptable salt, solvate, clathrate, or prodrug thereof is particularly useful for immunosuppression or for treating or preventing inflammatory conditions, allergic disorders, and immune disorders.

The invention also encompasses pharmaceutical compositions comprising a compound of the invention or a pharmaceutically acceptable salt, solvate, clathrate, or prodrug thereof; and a pharmaceutically acceptable carrier or vehicle. These compositions may further comprise additional agents. These compositions are useful for immunosuppression and treating or preventing inflammatory conditions, allergic disorders and immune disorders.

The invention further encompasses methods for treating or preventing inflammatory conditions, allergic disorders, and immune disorders, comprising administering to a subject in need thereof an effective amount of a compound of the invention or a pharmaceutically acceptable salt, solvate, clathrate, or prodrug thereof, or a pharmaceutical composition comprising a compound of the invention or a pharmaceutically acceptable salt, solvate, clathrate, or prodrug thereof. These methods may also comprise administering to the subject an additional agent separately or in a combination composition with the compound of the invention or a pharmaceutically acceptable salt, solvate, clathrate, or prodrug thereof.

The invention further encompasses methods for suppressing the immune system of a subject, comprising administering to a subject in need thereof an effective amount of a compound of the invention or a pharmaceutically acceptable salt, solvate, clathrate, or prodrug thereof, or a pharmaceutical composition comprising a compound of the invention or a pharmaceutically acceptable salt, solvate, clathrate, or prodrug thereof. These methods may also comprise administering to the subject an additional agent separately or in a combination composition with the compound of the invention or a pharmaceutically acceptable salt, solvate, clathrate, or prodrug thereof.

The invention further encompasses methods for inhibiting immune cell activation, including inhibiting proliferation of T cells and/or B cells, in vivo or in vitro comprising administering to the cell an effective amount of a compound of the invention or a pharmaceutically acceptable salt, solvate, clathrate, or prodrug thereof or a pharmaceutical composition comprising a compound of the invention or a pharmaceutically acceptable salt, solvate, clathrate, or prodrug thereof.

The invention further encompasses methods for inhibiting cytokine production in a cell (e.g., IL-2, IL-4, IL-5, IL-13, GM-CSF, TNF-α, and/or INF-γ production) in vivo or in vitro comprising administering to a cell an effective amount of a compound of the invention or a pharmaceutically acceptable salt, solvate, clathrate, or prodrug thereof or a pharmaceutical composition comprising a compound of the invention or a pharmaceutically acceptable salt, solvate, clathrate, or prodrug thereof.

The invention further encompasses methods for modulating ion channel activity (e.g., CRAC) in vivo or in vitro comprising administering an effective amount of a compound of the invention or a pharmaceutically acceptable salt, solvate, clathrate, or prodrug thereof or a pharmaceutical composition comprising a compound of the invention or a pharmaceutically acceptable salt, solvate, clathrate, or prodrug thereof.

All of the methods of this invention may be practice with a compound of the invention alone, or in combination with other agents, such as other immunosuppressive agents, anti-inflammatory agents, agents for the treatment of allergic disorders or agents for the treatment of immune disorders.

DETAILED DESCRIPTION OF THE INVENTION

Definitions

Unless otherwise specified, the below terms used herein are defined as follows:

As used herein, the term an "aromatic ring" or "aryl" means a monocyclic or polycyclic-aromatic ring or ring radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl or alkyl substituted with one or more halo), hydroxy, alkoxy (preferably, lower alkoxy), alkylsulfanyl, cyano, halo, amino, and nitro. In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents. Examples of substituents include, but are not limited to, amino, alkylamino, alkoxy, alkylsulfanyl, oxo, halo, acyl, nitro, hydroxyl, cyano, aryl, alkylaryl, aryloxy, arylsulfanyl, arylamino, carbocyclyl, carbocyclyloxy, carbocyclylthio, carbocyclylamino, heterocyclyl, heterocyclyloxy, heterocyclylamino, heterocyclylthio, and the like. In addition, any carbon in the alkyl segment may be substituted with oxygen (=O), sulfur (=S), or nitrogen (=NR$^{22}$, wherein R$^{22}$ is —H, an alkyl, acetyl, or aralkyl). Lower alkyls are typically preferred for the compounds of this invention.

The term alkylene refers to an alkyl group or a cycloalkyl group that has two points of attachment to two moieties (e.g., {—CH$_2$—}, —{CH$_2$CH$_2$—},

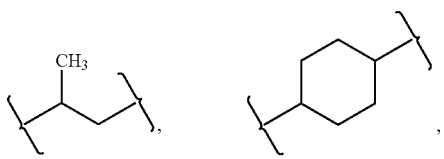

etc., wherein the brackets indicate the points of attachment). Alkylene groups may be substituted or unsubstituted with one or more substituents.

An aralkyl group refers to an aryl group that is attached to another moiety via an alkylene linker. Aralkyl groups can be substituted or unsubstituted with one or more substituents.

The term "alkoxy," as used herein, refers to an alkyl group which is linked to another moiety though an oxygen atom. Alkoxy groups can be substituted or unsubstituted with one or more substituents.

The term "alkylsulfanyl," as used herein, refers to an alkyl group which is linked to another moiety though a divalent sulfur atom. Alkylsulfanyl groups can be substituted or unsubstituted with one or more substituents.

The term "arylsulfanyl," as used herein, refers to an aryl group which is linked to another moiety though a divalent sulfur atom. Arylsulfanyl groups can be substituted or unsubstituted with one or more substituents.

The term "alkyl ester" as used herein, refers to a group represented by the formula —C(O)OR$_{32}$, wherein R$_{32}$ is an alkyl group. A lower alkyl ester is a group represented by the formula —C(O)OR$_{32}$, wherein R$_{32}$ is a lower alkyl group.

The term "heteroalkyl," as used herein, refers to an alkyl group which has one or more carbons in the alkyl chain replaced with an —O—, —S— or —NR$_{27}$—, wherein R$_{27}$ is H or a lower alkyl. Heteroalkyl groups can be substituted or unsubstituted with one or more substituents.

The term "alkylamino," as used herein, refers to an amino group in which one hydrogen atom attached to the nitrogen has been replaced by an alkyl group. The term "dialkylamino," as used herein, refers to an amino group in which two hydrogen atoms attached to the nitrogen have been replaced by alkyl groups, in which the alkyl groups can be the same or different. Alkylamino groups and dialkylamino groups can be substituted or unsubstituted with one or more substituents.

As used herein, the term "alkenyl" means a straight chain or branched, hydrocarbon radical typically having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups can be substituted or unsubstituted with one or more substituents.

As used herein, the term "alkynyl" means a straight chain or branched, hydrocarbonon radical typically having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl,-1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be substituted or unsubstituted with one or more substituents.

As used herein, the term "cycloalkyl" means a saturated, mono- or polycyclic alkyl radical typically having from 3 to 14 carbon atoms. Representative cycloalkyls include cyclopropyl, cyclobutyl, cyclopentyl, cyclohexyl, cycloheptyl, cyclooctyl, cyclononyl, cyclodecyl, adamantly, decahydronaphthyl, octahydropentalene, bicycle[1.1.1]pentanyl, and the like. Cycloalkyl groups can be substituted or unsubstituted with one or more substituents.

As used herein, the term "cycloalkenyl" means a cyclic non-aromatic alkenyl radical having at least one carbon-carbon double bond in the cyclic system and typically having from 5 to 14 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like. Cycloalkenyl groups can be substituted or unsubstituted with one or more substituents.

As used herein, the term "heterocycle" or "heterocyclyl" means a monocyclic or polycyclic heterocyclic ring (typically having 3- to 14-members) which is either a saturated ring or an unsaturated non-aromatic ring. A 3-membered heterocycle can contain up to 3 heteroatoms, and a 4- to 14-membered heterocycle can contain from 1 to about 8 heteroatoms. Each heteroatom is independently selected from nitrogen, which can be quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, 4H-pyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halo, an alkyl, a haloalkyl, or aryl). Only stable isomers of such substituted heterocyclic groups are contemplated in this definition.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquniolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, qunizaolinyl, purinyl, pyrrolo[2,3]pyrimidyl, pyrazolo[3,4]pyrimidyl or benzo(b)thienyl and the like. Heteroaryl groups may be optionally substituted with one or more substituents A heteroaralkyl group refers to a heteroaryl group that is attached to another moiety via an alkylene linker. Heteroaralkyl groups can be substituted or unsubstituted with one or more substituents.

As used herein, the term "halogen" or "halo" means —F, —Cl, —Br or —I.

As used herein, the term "haloalkyl" means an alkyl group in which one or more —H is replaced with a halo group. Examples of haloalkyl groups include —CF$_3$, —CHF$_2$, —CCl$_3$, —CH$_2$CH$_2$Br, —CH$_2$CH(CH$_2$CH$_2$Br)CH$_3$, —CHICH$_3$, and the like.

As used herein, the term "haloalkoxy" means an alkoxy group in which one or more —H is replaced with a halo group. Examples of haloalkoxy groups include —OCF$_3$ and —OCHF$_2$.

The terms "bioisostere" and "bioisosteric replacement" have the same meanings as those generally recognized in the art. Bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

As used herein, the terms "subject", "patient" and "animal", are used interchangeably and include, but are not limited to, a cow, monkey, horse, sheep, pig, mini pig, chicken, turkey, quail, cat, dog, mouse, rat, rabbit, guinea pig and human. The preferred subject, patient or animal is a human.

As used herein, the term "lower" refers to a group having up to four carbon atoms. For example, a "lower alkyl" refers to an alkyl radical having from 1 to 4 carbon atoms, and a "lower alkenyl" or "lower alkynyl" refers to an alkenyl or alkynyl radical having from 2 to 4 carbon atoms, respectively. A lower alkoxy or a lower alkylsulfanyl refers to an alkoxy or an alkylsulfanyl having from 1 to 4 carbon atoms. Lower substituents are typically preferred.

Where a particular substituent, such as an alkyl substituent, occurs multiple times in a given structure or moeity, the identity of the substitutent is independent in each case and may be the same as or different from other occurrences of that substituent in the structure or moiety. Furthermore, individual substituents in the specific embodiments and exemplary compounds of this invention are preferred in combination with other such substituents in the compounds of this invention, even if such individual substituents are not expressly noted as being preferred or not expressly shown in combination with other substituents.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Suitable substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkoxy, alkylsulfanyl, alkylamino, dialkylamino, alkylene, alkenyl, alkynyl, cycloalkyl, cycloalkenyl, heterocyclyl, aryl, aralkyl, heteroaryl, and heteroaralkyl include an alkyl, an alkoxy, an alkylsulfanyl, an alkylamino, a dialkylamino, an alkenyl, an alkynyl, a cycloalkyl, a cycloalkenyl, a heterocyclyl, an aryl, a heteroaryl, an aralkyl, a heteraralkyl, a haloalkyl, —C(O)NR$_{23}$R$_{24}$, —NR$_{25}$C(O)R$_{26}$, halo, —OR$_{25}$, cyano, nitro, haloalkoxy, —C(O)R$_{25}$, —NR$_{23}$R$_{24}$, —SR$_{25}$, —C(O)OR$_{25}$, —OC(O)R$_{25}$, —NR$_{25}$C(O)NR$_{23}$R$_{24}$, —OC(O)NR$_{23}$R$_{24}$, —NR$_{25}$C(O)OR$_{26}$, —S(O)R$_{25}$, or —S(O)$_p$NR$_{23}$R$_{24}$, wherein R$_{23}$ and R$_{24}$, for each occurrence are, independently, H, an alkyl, an alkenyl, an alkynyl, a cycloalkyl, a cycloalkenyl, a heterocyclyl, an aryl, a heteroaryl, an aralkyl, or a heteraralkyl; or R$_{23}$ and R$_{24}$ taken together with the nitrogen to which they are attached is a heterocyclyl or a heteroaryl; and R$_{25}$ and R$_{26}$ for each occurrence are, independently, H, an alkyl, an alkenyl, an alkynyl, a cycloalkyl, a cycloalkenyl, a heterocyclyl, an aryl, a heteroaryl, an aralkyl, or a heteraralkyl;

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, =S, =N—R$_{22}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds of the invention containing reactive functional groups (such as, without limitation, carboxy, hydroxy, and amino moieties) also include protected derivatives thereof. "Protected derivatives" are those compounds in which a reactive site or sites are blocked with one or more protecting groups. Suitable protecting groups for carboxy moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl, trimethyl silyl (TMS) and the like. Other suitable protecting groups are well known to those of ordinary skill in the art and include those found in T. W. Greene, Protecting Groups in Organic Synthesis, John Wiley & Sons, Inc. 1981, the entire teachings of which are incorporated herein by reference.

As used herein, the term "compound(s) of this invention" and similar terms refers to a compound of any one of formulas (I) through (XIV), or Table 1, or a pharmaceutically acceptable salt, solvate, clathrate, or prodrug thereof and also include protected derivatives thereof.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, but they may have activity in their unreacted forms. Examples of prodrugs contemplated in this invention include, but are not limited to, analogs or derivatives of compounds of any one of formulas (I) through (XIV), or Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of formulas (I) through (XIV), or of Table 1 that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed), the entire teachings of which are incorporated herein by reference.

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "pharmaceutically acceptable salt," is a salt formed from an acid and a basic group of one of the compounds of any one of formulas (I) through (XIV) or of Table 1. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of formulas (I) through (XIV) or Table 1 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound of any one of formulas (I) through (XIV) or Table 1 having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more solvent molecules to one or more molecules of a compound of any one of formulas (I) through (XIV) or Table 1. The term solvate includes hydrates (e.g., hemi-hydrate, mono-hydrate, dihydrate, trihydrate, tetrahydrate, and the like).

As used herein, the term "clathrate" means a compound of the present invention or a salt thereof in the form of a crystal lattice that contains spaces (e.g., channels) that have a guest molecule (e.g., a solvent or water) trapped within.

As used herein, the term "asthma" means a pulmonary disease, disorder or condition characterized by reversible airway obstruction, airway inflammation, and increased airway responsiveness to a variety of stimuli.

"Immunosuppression" refers to impairment of any component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200-210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals." In Principles and Methods of Toxicology: Fourth Edition (A. W. Hayes, Ed.), pp. 1415-1450, Taylor & Francis, Philadelphia, Pa.).

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that are substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the nervous system in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barré, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound or a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

The compounds of this invention can be used to prevent or to treat subjects with inflammatory disorders. As used herein, an "inflammatory disorder" means a disease, disorder or condition characterized by inflammation of body tissue or having an inflammatory component. These include local inflammatory responses and systemic inflammation. Examples of such inflammatory disorders include: transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma, and cancer. There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory disorder" herein refers to administering a compound or a composition of the invention to a subject, who has an inflammatory disorder, a symptom of such a disorder or a predisposition towards such a disorder, with the purpose to cure, relieve, alter, affect, or prevent the inflammatory disorder, the symptom of it, or the predisposition towards it.

An "effective amount" is the quantity of compound in which a beneficial outcome is achieved when the compound is administered to a subject or alternatively, the quantity of compound that possess a desired activity in-vivo or in-vitro. In the case of inflammatory disorders and autoimmune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory disorder, autoimmune disorder, allergic disorder, or the degree of immunosuppression sought. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 1 gram/mm$^2$.

The compounds of the invention may contain one or more chiral centers and/or double bonds and, therefore, may exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers and stereoisomers, that is, both the stereomerically pure form (e.g., geometrically pure, enantiomerically pure, or diastereomerically pure) and enantiomeric, diastereomeric, and geometric isomeric mixtures. In some cases, one enantiomer, diastereomer, or geometric isomer will possess superior activity or an improved toxicity or kinetic profile compared to others. In those cases, such enantiomers, diastereomers, and geometric isomers of a compound of this invention are preferred.

The term "inhibit production of IL-2" and like terms means inhibiting IL-2 synthesis (e.g. by inhibiting transcription (mRNA expression), or translation (protein expression)) and/or inhibiting IL-2 secretion in a cell that has the ability to produce and/or secrete IL-2 (e.g., T lymphocyte). Likewise, the term "inhibiting production of IL-4, IL-5, IL-13, GM-CSF, TNF-α or INF-γ means inhibiting the synthesis (e.g. by inhibiting transcription, or translation) and/or inhibiting the secretion in a cell that has the ability to produce and/or secrete these cytokines.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a composition that is "substantially free" of a compound means that the composition contains less than about 20% by weight, more preferably less than about 10% by weight, even more preferably less than about 5% by weight, and most preferably less than about 3% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of any one of formulas (I) through (XIV) or Table 1.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When administered to a patient, e.g., to a non-human animal for veterinary use or for improvement of livestock, or to a human for clinical use, the compounds of the invention are typically administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single compound of the invention by weight of the isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

Specific Embodiments

The invention relates to compounds and pharmaceutical compositions that are particularly useful for immunosuppression or to treat or prevent inflammatory conditions, immune disorders, and allergic disorders.

In one embodiment, the invention relates to compounds of formula (I):

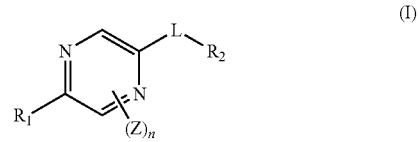

(I)

or a pharmaceutically acceptable salt, solvate, clathrate, or prodrug thereof, wherein:

L is a linker selected from the group consisting of —NRCH$_2$—, —CH$_2$NR—, —C(O)—, —NR—C(O)—, —C(O)—NR—, —C(S)—, —NR—C(S)—, —C(S)—NR—;

each Z is independently selected from the group consisting of a lower alkyl, a lower haloalkyl, a halo, a lower alkoxy, a lower alkyl sufanyl, cyano, nitro, or lower haloalkoxy;

R, for each occurrence is independently selected from —H, an alkyl, —C(O)R$_5$, or —C(O)OR$_5$;

R$_1$ is an optionally substituted aryl or an optionally substituted heteroaryl;

R$_2$ is an optionally substituted cycloalkyl, an optionally substituted cycloalkenyl, an optionally substituted aryl, or an optionally substituted heteroaryl;

R$_5$, for each occurrence, is independently, H, an alkyl, a cycloalkyl, a heterocyclyl, an aryl, a heteroaryl, an aralkyl, or a heteraralkyl; and n is 0, 1 or 2.

In another embodiment, the invention relates to compounds of formula (II):

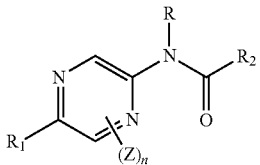

(II)

or a pharmaceutically acceptable salt, solvate, clathrate, or prodrug thereof, wherein R, R$_1$, R$_2$, Z and n are defined as for formula (I).

In another embodiment, the invention relates to compounds of formula (III):

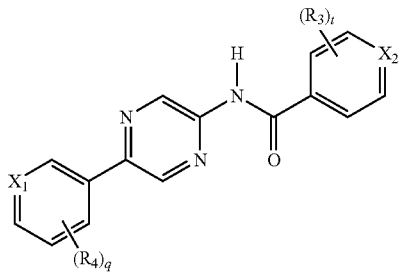

(III)

or a pharmaceutically acceptable salt, solvate, clathrate, or prodrug thereof, wherein:

X$_1$ is CH, CR$_4$, or N;

X$_2$ is CH, CR$_3$, or N;

R$_3$ and R$_4$, for each occurrence are, independently, a halo, cyano, nitro, an alkyl, a haloalkyl, an alkoxy, alkylsulfanyl, hydroxyl, a heteroaryl, —NH$_2$, alkylamino, dialkylamino, or —C(O)R$_6$;

R$_6$, for each occurrence, is independently, H, an alkyl, a cycloalkyl, a heterocyclyl, an aryl, a heteroaryl, an aralkyl, or a heteraralkyl, —OR$_7$, —SR$_7$, or —NR$_7$R$_7$;

R$_7$, for each occurrence, is independently, H, an alkyl, a heteroalkyl, a cycloalkyl, a heterocyclyl, an aryl, a heteroaryl, an aralkyl, or a heteraralkyl; and q and t, for each occurrence are, independently, 0 or an integer from 1 to 5.

In another embodiment, the invention relates to compounds of formula (IV):

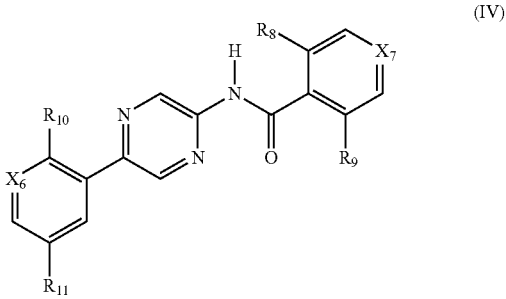

(IV)

or a pharmaceutically acceptable salt, solvate, clathrate, or prodrug thereof, wherein:

X$_6$ and X$_7$ are each, independently, CH or N;

R$_8$ and R$_9$ are each, independently, a halo, a lower alkyl, a lower alkoxy, a haloalky, or a lower haloalkoxyl; and R$_{10}$ and R$_{11}$, are each, independently, a halo, cyano, a lower alkyl, a lower haloalkyl, a lower alkoxy, a lower haloalkoxy, tetrazolyl, 1-alkyl-tetrazolyl, a lower alkylester, —C(O)NH$_2$, furanyl, oxazolyl, oxadiazolyl, 3-alkyloxadiazolyl, or tetrazolyl.

In another embodiment, the invention relates to compounds of formula (V):

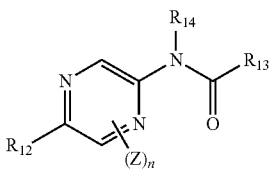

(V)

or a pharmaceutically acceptable salt, solvate, clathrate, or prodrug thereof, wherein:

R$_{12}$ is an aryl or a heteroaryl, wherein the aryl and heteroaryl are optionally substituted with one or more substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl, a halo, cyano, nitro, —OR$_{17}$, —SR$_{17}$, —S(O)$_p$R$_{17}$, —S(O)$_p$OR$_{17}$, —OS(O)$_p$R$_{17}$, —OS(O)$_p$OR$_{17}$, —NR$_{17}$S(O)$_p$R$_{17}$, —S(O)$_p$NR$_{15}$R$_{16}$, —NR$_{15}$R$_{16}$, —C(X$_3$)R$_{17}$, —C(X$_3$)OR$_{17}$, —C(X$_3$)SR$_{17}$, —C(X$_3$)NR$_{15}$R$_{16}$, —NR$_{17}$C(X$_3$)R$_{18}$, —NR$_{17}$C(X$_3$)OR$_{18}$, —NR$_{17}$C(X$_3$)SR$_{18}$, —NR$_{17}$C(X$_3$)NR$_{15}$R$_{16}$, —OC(X$_3$)R$_{17}$, —OC(X$_3$)OR$_{17}$, —OC(X$_3$)SR$_{17}$, —SC(X$_3$)OR$_{17}$, —SC(X$_3$)SR$_{17}$, —OC(X$_3$)NR$_{15}$R$_{16}$, —SC(X$_3$)NR$_{15}$R$_{16}$, —P(X$_4$)(X$_5$R$_{17}$)$_2$, —X$_5$P(X$_4$)(X$_5$R$_{17}$)$_2$, —P(X$_4$)(R$_{17}$)$_2$, —P(X$_4$)(R$_{17}$)(X$_5$R$_{17}$);

R$_{13}$ is a cycloalkyl, a cycloalkenyl, an aryl, or a heteroaryl, wherein the cycloalkyl, cycloalkenyl, aryl, or heteroaryl are optionally substituted with one or more substituents selected from the group consisting of an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted aralkyl, or an optionally substituted heteraralkyl, a halo, cyano, nitro, a haloalkyl, —OR$_{17}$, —SR$_{17}$, —S(O)$_p$R$_{17}$, —S(O)$_p$OR$_{17}$, —OS(O)$_p$R$_{17}$, —OS(O)$_p$OR$_{17}$, —S(O)$_p$NR$_{15}$R$_{16}$, —NR$_{15}$R$_{16}$, —C(X$_3$)R$_{17}$, —C(X$_3$)OR$_{17}$, —C(X$_3$)SR$_{17}$, —C(X$_3$)NR$_{15}$R$_{16}$, —NR$_{17}$C(X$_3$)R$_{18}$, —NR$_{17}$C(X$_3$)OR$_{18}$, —NR$_{17}$C(X$_3$)SR$_{18}$, —NR$_{17}$C(X$_3$)NR$_{15}$R$_{16}$, —OC(X$_3$)R$_{17}$, —OC(X$_3$)OR$_{17}$, —OC(X$_3$)SR$_{17}$, —SC(X$_3$)OR$_{17}$, —SC(X$_3$)SR$_{17}$, —OC(X$_3$)NR$_{15}$R$_{16}$, —SC(X$_3$)NR$_{15}$R$_{16}$, —P(X$_4$)(X$_5$R$_{17}$)$_2$, —X$_5$P(X$_4$)(X$_5$R$_{17}$)$_2$, —P(X$_4$)(R$_{17}$)$_2$, —P(X$_4$)(R$_{17}$)(X$_5$R$_{17}$);

R$_{14}$, for each occurrence is independently selected from —H, an alkyl, —C(O)R$_{20}$, or —C(O)OR$_{20}$;

R$_{15}$ and R$_{16}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{15}$ and R$_{16}$ taken together with the nitrogen to which they are attached are an optionally substituted heterocyclyl or optionally substituted heteroaryl;

R$_{17}$ and R$_{18}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{19}$, for each occurrence, is independently —H, a halo, an alkyl, —OR$_{17}$, —NR$_{15}$R$_{16}$, —C(O)R$_{17}$, —C(O)OR$_{17}$, or —C(O)NR$_{15}$R$_{16}$;

R$_{20}$, for each occurrence, is independently, H or an alkyl;

X$_3$ is =O, =S, or =N—R$_{19}$;

X$_4$ is =O or =S;

X$_5$ is —O— or —S—;

p is 1 or 2; and

Z and n are defined as for formula (I).

In another embodiment, the invention relates to compounds of formula (VI):

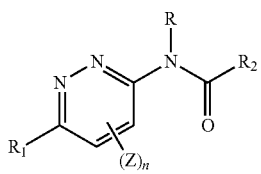

(VI)

or a pharmaceutically acceptable salt, solvate, clathrate, or prodrug thereof, wherein R, R$_1$, R$_2$, Z and n are defined as for formula (I).

In another embodiment, the invention relates to compounds of formula (VII):

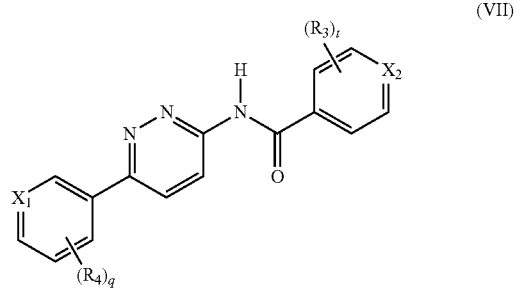

(VII)

or a pharmaceutically acceptable salt, solvate, clathrate, or prodrug thereof, wherein X$_1$, X$_2$, R$_3$, R$_4$, q and t are defined as for formula (III).

In another embodiment, the invention relates to compounds of formula VII):

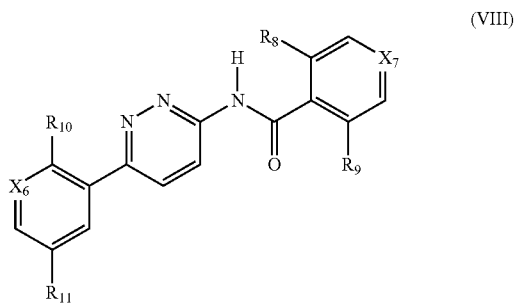

(VIII)

or a pharmaceutically acceptable salt, solvate, clathrate, or prodrug thereof, wherein X$_6$, X$_7$, R$_8$, R$_9$, R$_{10}$ and R$_{11}$ are defined as for formula (IV).

In another embodiment, the invention relates to compounds of formula (IX):

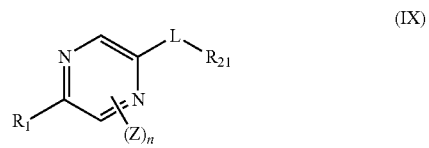

(IX)

or a pharmaceutically acceptable salt, solvate, clathrate, or prodrug thereof, wherein:

R$_{21}$ is an alkyl which is optionally substituted with one or more substituents selected from the group consisting of an optionally substituted alkynyl, an optionally substituted cycloalkyl, an optionally substituted cycloalkenyl, an optionally substituted aryl, an optionally substituted heteroaryl, an optionally substituted aralkyl, an optionally substituted heteraralkyl, a halo, cyano, nitro, a haloalkyl, —OR$_{17}$, —SR$_{17}$, —S(O)$_p$R$_{17}$, —S(O)$_p$OR$_{17}$, —OS(O)$_p$R$_{17}$, —OS(O)$_p$OR$_{17}$, —S(O)$_p$NR$_{15}$R$_{16}$, —NR$_{15}$R$_{16}$, —C(X$_3$)R$_{17}$, —C(X$_3$)OR$_{17}$, —C(X$_3$)SR$_{17}$, —C(X$_3$)NR$_{15}$R$_{16}$, —NR$_{17}$C(X$_3$)R$_{18}$, —NR$_{17}$C(X$_3$)OR$_{18}$, —NR$_{17}$C(X$_3$)SR$_{18}$, —NR$_{17}$C(X$_3$)NR$_{15}$R$_{16}$, —OC(X$_3$)R$_{17}$, —OC(X$_3$)OR$_{17}$, —OC(X$_3$)SR$_{17}$, —SC(X$_3$)OR$_{17}$, —SC(X$_3$)SR$_{17}$, —OC(X$_3$)NR$_{15}$R$_{16}$, —SC(X$_3$)NR$_{15}$R$_{16}$, —P(X$_4$)(X$_5$R$_{17}$)$_2$, —X$_5$P(X$_4$)(X$_5$R$_{17}$)$_2$, —P(X$_4$)(R$_{17}$)$_2$, —P(X$_4$)(R$_{17}$)(X$_5$R$_{17}$);

$R_1$, Z and n are defined as for formula (I); and $R_{15}$, $R_{16}$, $R_{17}$, $R_{18}$, $X_3$, $X_4$, $X_5$, and p are defined as for formula (V).

In another embodiment, the invention relates to compounds of formula (X):

(X)

or a pharmaceutically acceptable salt, solvate, clathrate, or prodrug thereof, wherein:

R, $R_1$, Z, and n are defined as for formula (I); and $R_{21}$ is defined as for formula (IX).

In another embodiment, the invention relates to compounds of formula (XI):

(XI)

or a pharmaceutically acceptable salt, solvate, clathrate, or prodrug thereof, wherein:

$X_6$, $R_{10}$ and $R_{11}$ are defined as for formula (IV); and $R_{21}$ is defined as for formula (IX).

In another embodiment, the invention relates to compounds of formula (XII):

(XII)

or a pharmaceutically acceptable salt, solvate, clathrate, or prodrug thereof, wherein:

$X_8$ and $X_9$ are N and $X_{10}$ and $X_{11}$ are CH or CZ; or $X_{10}$ and $X_{11}$ are N and $X_8$ and $X_9$ are CH or CZ;

L, Z, $R_1$, and $R_2$ are defined as for formula (I).

In another embodiment, the invention relates to compounds of formula (XIII):

(XIII)

or a pharmaceutically acceptable salt, solvate, clathrate, or prodrug thereof, wherein:

$X_8$, $X_9$, $X_{10}$ and $X_{11}$ are defined as for formula (XII); and

R, $R_1$, and $R_2$ are defined as for formula (I).

In another embodiment, the invention relates to compounds of formula (XIV):

(XIV)

or a pharmaceutically acceptable salt, solvate, clathrate, or prodrug thereof, wherein:

$X_8$, $X_9$, $X_{10}$ and $X_{11}$ are defined as for formula (XII);

$R_2$ are defined as for formula (I); and $X_6$, $R_{10}$ and $R_{11}$ are defined as for formula (IV).

In one embodiment, in the compounds represented by formula (I), (IX), or (XII), L is —NH—C(O)— or —C(O)—NH—.

In another embodiment, in the compounds represented by formula (I), (IX), or (XII), L is —NH—CH$_2$— or —CH$_2$—NH—.

In another embodiment, in the compounds represented by formula (I), (II), (V), (VI), (IX), or (X), n is 0.

In another embodiment, in the compounds represented by formula (I), (II), (V), (VI), (IX), or (X), n is 1. In one aspect of this embodiment, Z is a halo.

In another embodiment, in the compounds represented by formula (I), (II), (V), (VI), (IX), or (X), n is 2. In one aspect of this embodiment, Z, for each occurrence, is, independently, a halo.

In another embodiment, in the compounds represented by formula (I), (II), (VI), (IX), (X), (XII), or (XIII), R is H.

In another embodiment, in the compounds represented by formula (I), (II), (VI), (IX), (X), (XII), or (XIII), R is a lower alkyl, such as methyl.

In another embodiment, in the compounds represented by formula (I), (II), (VI), (IX), (X), (XII), or (XIII), $R_1$ is selected from the group consisting of an optionally substituted phenyl, an optionally substituted naphthyl, an optionally substituted anthracenyl, an optionally substituted pyridyl, an optionally substituted furyl, an optionally substituted thienyl, an optionally substituted pyrrolyl, an optionally substituted oxazolyl, an optionally substituted imidazolyl, an optionally substituted indolizinyl, an optionally substituted thiazolyl, an optionally substituted isoxazolyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted pyrazinyl, an optionally substituted quinolinyl, an optionally substituted isoquniolinyl, an optionally substituted indazolyl, an optionally substituted benzoxazolyl, an optionally substituted benzofuryl, an optionally substituted benzothiazolyl, an optionally substituted indolizinyl, an optionally substituted imidazopyridinyl, an optionally substituted isothiazolyl, an optionally substituted tetrazolyl, an optionally substituted benzoxazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidyl, an optionally substituted pyridopyrimidyl, an optionally substituted pyrazolo[3,4]pyrimidyl or an optionally substituted benzo(b)thienyl.

In another embodiment, in the compounds represented by formula (I), (II), (VI), (IX), (X), (XII), or (XIII), $R_1$ is an optionally substituted phenyl or an optionally substituted 5-membered heteroaryl. In one aspect of this embodiment, $R_1$ is an optionally substituted 5-membered heteroaryl. Examples of optionally substituted 5-membered heteroaryl groups include an optionally substituted furyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted pyrazolyl, an optionally substituted isothiazolyl, an optionally substituted pyrazinyl, an optionally substituted triazinyl, an optionally substituted triazolyl, an optionally substituted thiadiazolyl, and an optionally substituted tetrazolyl.

In another embodiment, in the compounds represented by formula (I), (II), (VI), (IX), (X), (XII), or (XIII), $R_1$ is an optionally substituted phenyl or an optionally substituted 6-membered heteroaryl. In one aspect of this embodiment, $R_1$ is an optionally substituted 6-membered heteroaryl. Examples of optionally substituted 6-membered heteroaryl groups include an optionally substituted pyridyl, an optionally substituted pyridazinyl, an optionally substituted pyrimidinyl, an optionally substituted pyrazinyl, or an optionally substituted triazinyl. In another aspect of this embodiment, $R_1$ is unsubstituted. In another aspect of this embodiment, $R_1$ is substituted with one substituent, for example, $R_1$ is substituted with a substituent that is ortho to its point of attachment to the pyrazine or pyridazine ring. In another aspect of this embodiment, $R_1$ is substituted with two substituent, for example $R_1$ is substituted with one substituent that is ortho to its point of attachment to the pyrazine or pyridazine ring, and another substituent that is para to the first substituent.

In another embodiment, in the compounds represented by formula (I), (II), (VI), (IX), (X), (XII), or (XIII), $R_1$ is an optionally substituted heteroaryl selected from the group consisting of an optionally substituted indolizinyl, an optionally substituted quinolinyl, an optionally substituted isoquniolinyl, an optionally substituted indazolyl, an optionally substituted benzoxazolyl, an optionally substituted benzofuryl, an optionally substituted benzothiazolyl, an optionally substituted indolizinyl, an optionally substituted imidazopyridinyl, an optionally substituted benzoxazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidyl, an optionally substituted pyridopyrimidyl, an optionally substituted pyrazolo[3,4]pyrimidyl or an optionally substituted benzo(b)thienyl.

In another embodiment, in the compounds represented by formula (I), (II), (VI), (IX), (X), (XII), or (XIII), $R_1$ is an optionally substituted phenyl, an optionally substituted tetrazolyl, or an optionally substituted pyridinyl.

In another embodiment, in the compounds represented by formula (I), (II), (VI), (IX), (X), (XII), or (XIII), $R_1$ is an optionally substituted phenyl or an optionally substituted pyridinyl.

In another embodiment, in the compounds represented by formula (I), (II), (VI), (IX), (X), (XII), or (XIII), $R_1$ is substituted with one or more substituents selected from the group consisting of an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted aralkyl, or an optionally substituted heteraralkyl, a halo, cyano, nitro, a haloalkyl, $-OR_{17}$, $-SR_{17}$, $-S(O)_pR_{17}$, $-S(O)_pOR_{17}$, $-OS(O)_pR_{17}$, $-OS(O)_pOR_{17}$, $-S(O)_pNR_{15}R_{16}$, $-NR_{15}R_{16}$, $-C(X_3)R_{17}$, $-C(X_3)OR_{17}$, $-C(X_3)SR_{17}$, $-C(X_3)NR_{15}R_{16}$, $-NR_{17}C(X_3)R_{18}$, $-NR_{17}C(X_3)OR_{18}$, $-NR_{17}C(X_3)SR_{18}$, $-NR_{17}C(X_3)NR_{15}R_{16}$, $-OC(X_3)R_{17}$, $-OC(X_3)OR_{17}$, $-OC(X_3)SR_{17}$, $-SC(X_3)OR_{17}$, $-SC(X_3)SR_{17}$, $-OC(X_3)NR_{15}R_{16}$, $-SC(X_3)NR_{15}R_{16}$, $-P(X_4)(X_5R_{17})_2$, $-X_5P(X_4)(X_5R_{17})_2$, $-P(X_4)(R_{17})_2$, $-P(X_4)(R_{17})(X_5R_{17})$; wherein $R_{15}$, $R_{16}$, $R_{17}$, $R_{18}$, $X_3$, $X_4$, $X_5$, and p are defined as above.

In another embodiment, in the compounds represented by formula (I), (II), (VI), (IX), (X), (XII), or (XIII), $R_1$ is substituted with one or more substituents selected from the group consisting of a lower alkyl, a halo, cyano, nitro, a lower haloalkyl, a lower alkoxy, a lower sulfanylalkyl, $-S(O)_pR_{31}$, $-S(O)_pNR_{29}R_{30}$, $-NR_{29}R_{30}$, $-C(O)R_{28}$, $-C(O)OR_{28}$, $-C(O)NR_{29}R_{30}$, $-NR_{29}C(O)R_{30}$, $-NR_{29}C(O)OR_{28}$, $-NR_{28}C(O)NR_{29}R_{30}$, $-OC(O)R_{28}$, $-OC(O)OR_{28}$, and $-OC(O)NR_{29}R_{30}$; wherein p is defined as above; $R_{28}$, $R_{29}$, $R_{30}$, for each occurrence are, independently, H or a lower alkyl; and $R_{31}$, for each occurrence, is independently a lower alkyl.

In another embodiment, in the compounds represented by formula (I), (II), (VI), (IX), (X), (XII), or (XIII), $R_1$ is substituted with one or more substituents selected from the group consisting of a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), $-C(O)H$, $-C(O)OR_{28}$, $-C(O)R_{28}$, and $-C(O)NR_{29}R_{30}$; wherein $R_{28}$, $R_{29}$, $R_{30}$, for each occurrence are, independently, H or a lower alkyl.

In another embodiment, in the compounds represented by formula (I), (II), (VI), (XII), (XIII), or (XIV), $R_2$ is an optionally substituted aryl or an optionally substituted heteroaryl.

In another embodiment, in the compounds represented by formula (I), (II), (VI), (XII), (XIII), or (XIV), $R_2$ is an optionally substituted phenyl or an optionally substituted 5-membered heteroaryl. In one aspect of this embodiment, $R_2$ is an optionally substituted 5-membered heteroaryl. Examples of optionally substituted 5-membered heteroaryl groups include an optionally substituted furyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted pyrazolyl, an optionally substituted isothiazolyl, an optionally substituted pyrazinyl, an optionally substituted triazinyl, an optionally substituted triazolyl, an optionally substituted thiadiazolyl, and an optionally substituted tetrazolyl.

In another embodiment, in the compounds represented by formula (I), (II), (VI), (XII), (XIII), or (XIV), $R_2$ is an optionally substituted phenyl or an optionally substituted 6-membered heteroaryl. In one aspect of this embodiment, $R_2$ is an optionally substituted 6-membered heteroaryl. Examples of optionally substituted 6-membered heteroaryl groups include an optionally substituted pyridyl, an optionally substituted pyridazinyl, an optionally substituted pyrimidinyl, an optionally substituted pyrazinyl, or an optionally substituted triazinyl. In another aspect of this embodiment, $R_2$ is unsubstituted. In another aspect of this embodiment, $R_2$ is substituted with one substituent, for example, $R_2$ is substituted with a substituent that is ortho to its point of attachment to L or —NR—C(O)—. In another aspect of this embodiment, $R_2$ is substituted with two substituent, for example, $R_2$ is substituted with two substituent that ar ortho to its point of attachment to L or —NR—C(O)—.

In another embodiment, in the compounds represented by formula (I), (II), (VI), (XII), (XIII), or (XIV), $R_2$ is an optionally substitituted heteroaryl selected from the group consisting of an optionally substituted indolizinyl, an optionally substituted quinolinyl, an optionally substituted isoquniolinyl, an optionally substituted indazolyl, an optionally substituted benzoxazolyl, an optionally substituted benzofuryl, an optionally substituted benzothiazolyl, an optionally substituted indolizinyl, an optionally substituted imidazopyridinyl, an optionally substituted benzoxazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidyl, an optionally substituted pyridopyrimidyl, an optionally substituted pyrazolo[3,4]pyrimidyl or an optionally substituted benzo(b)thienyl.

In another embodiment, in the compounds represented by formula (I), (II), (VI), (XII), (XIII), or (XIV), $R_2$ is an optionally substituted phenyl or an optionally substituted pyridinyl.

In another embodiment, in the compounds represented by formula (I), (II), (VI), (XII), (XIII), or (XIV), $R_2$ is an optionally substituted cycloalkyl or an optionally substituted cycloalkenyl.

In another embodiment, in the compounds represented by formula (I), (II), (VI), (XII), (XIII), or (XIV), $R_2$ is substituted with one or more substituents selected from the group consisting of an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted aralkyl, or an optionally substituted heteralkyl, a halo, cyano, nitro, a haloalkyl, —$OR_{17}$, —$SR_{17}$, —$S(O)_pR_{17}$, —$S(O)_pOR_{17}$, —$OS(O)_pR_{17}$, —$OS(O)_pOR_{17}$, —$S(O)_pNR_{15}R_{16}$, —$NR_{15}R_{16}$, —$C(X_3)R_{17}$, —$C(X_3)OR_{17}$, —$C(X_3)SR_{17}$, —$C(X_3)NR_{15}R_{16}$, —$NR_{17}C(X_3)R_{18}$, —$NR_{17}C(X_3)OR_{18}$, —$NR_{17}C(X_3)SR_{18}$, —$NR_{17}C(X_3)NR_{15}R_{16}$, —$OC(X_3)R_{17}$, —$OC(X_3)OR_{17}$, —$OC(X_3)SR_{17}$, —$SC(X_3)OR_{17}$, —$SC(X_3)SR_{17}$, —$OC(X_3)NR_{15}R_{16}$, —$SC(X_3)NR_{15}R_{16}$, —$P(X_4)(X_5R_{17})_2$, —$X_5P(X_4)(X_5R_{17})_2$, —$P(X_4)(R_{17})_2$, —$P(X_4)(R_{17})(X_5R_{17})$; wherein $R_{15}$, $R_{16}$, $R_{17}$, $R_{18}$, $X_3$, $X_4$, $X_5$, and p are defined as above.

In another embodiment, in the compounds represented by formula (I), (II), (VI), (XII), (XIII), or (XIV), $R_2$ is substituted with one or more substituents selected from the group consisting of a lower alkyl, a halo, cyano, nitro, a lower haloalkyl, a lower alkoxy, a lower sulfanylalkyl, —$S(O)_pR_{31}$, —$S(O)_pNR_{29}R_{30}$, —$NR_{29}R_{30}$, —$C(O)R_{28}$, —$C(O)OR_{28}$, —$C(O)NR_{29}R_{30}$, —$NR_{29}C(O)R_{30}$, —$NR_{29}C(O)OR_{28}$, —$NR_{28}C(O)NR_{29}R_{30}$, —$OC(O)R_{28}$, —$OC(O)OR_{28}$, and —$OC(O)NR_{29}R_{30}$; wherein p is defined as above; $R_{28}$, $R_{29}$, $R_{30}$, for each occurrence are, independently, H or a lower alkyl; and $R_{31}$, for each occurrence, is independently a lower alkyl.

In another embodiment, in the compounds represented by formula (I), (II), (VI), (XII), (XIII), or (XIV), $R_2$ is substituted with one or more substituents selected from the group consisting of a halo or a lower alkyl.

In another embodiment, in the compounds represented by formula (I), (II), (VI), (XII), (XIII), or (XIV), $R_2$ is 2,6-difluorophenyl, 3-fluoropyridin-4-yl, or 3-methyl-pyridin-4-yl.

In another embodiment, in the compounds represented by formula (V), $R_{14}$ is H.

In another embodiment, in the compounds represented by formula (V), $R_{14}$ is a lower alkyl, such as methyl.

In another embodiment, in the compounds represented by formula (V), $R_{12}$ is selected from the group consisting of an optionally substituted phenyl, an optionally substituted naphthyl, an optionally substituted anthracenyl, an optionally substituted pyridyl, an optionally substituted furyl, an optionally substituted thienyl, an optionally substituted pyrrolyl, an optionally substituted oxazolyl, an optionally substituted imidazolyl, an optionally substituted indolizinyl, an optionally substituted thiazolyl, an optionally substituted isoxazolyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted pyrazinyl, an optionally substituted quinolinyl, an optionally substituted isoquniolinyl, an optionally substituted indazolyl, an optionally substituted benzoxazolyl, an optionally substituted benzofuryl, an optionally substituted benzothiazolyl, an optionally substituted indolizinyl, an optionally substituted imidazopyridinyl, an optionally substituted isothiazolyl, an optionally substituted tetrazolyl, an optionally substituted benzoxazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidyl, an optionally substituted pyridopyrimidyl, an optionally substituted pyrazolo[3,4]pyrimidyl or an optionally substituted benzo(b)thienyl.

In another embodiment, in the compounds represented by formula (V), $R_{12}$ is an optionally substituted phenyl or an optionally substituted 5-membered heteroaryl. In one aspect of this embodiment, $R_{12}$ is an optionally substituted 5-membered heteroaryl. Examples of optionally substituted 5-membered heteroaryl groups include an optionally substituted furyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted pyrazolyl, an optionally substituted isothiazolyl, an optionally substituted pyrazinyl, an optionally substituted triazinyl, an optionally substituted triazolyl, an optionally substituted thiadiazolyl, and an optionally substituted tetrazolyl.

In another embodiment, in the compounds represented by formula (V), $R_{12}$ is an optionally substituted phenyl or an optionally substituted 6-membered heteroaryl. In one aspect of this embodiment, $R_{12}$ is an optionally substituted 6-membered heteroaryl. Examples of optionally substituted 6-membered heteroaryl groups include an optionally substituted pyridyl, an optionally substituted pyridazinyl, an optionally substituted pyrimidinyl, an optionally substituted pyrazinyl, or an optionally substituted triazinyl. In another aspect of this embodiment, $R_{12}$ is unsubstituted. In another aspect of this embodiment, $R_{12}$ is substituted with one substituent, for example, $R_{12}$ is substituted with a substituent that is ortho to its point of attachment to the pyrazine or pyridazine ring. In another aspect of this embodiment, $R_{12}$ is substituted with two substituent, for example $R_{12}$ is substituted with one substituent that is ortho to its point of attachment to the pyrazine or pyridazine ring, and another substituent that is para to the first substituent.

In another embodiment, in the compounds represented by formula (V), $R_{12}$ is an optionally substituted heteroaryl selected from the group consisting of an optionally substituted indolizinyl, an optionally substituted quinolinyl, an optionally substituted isoquniolinyl, an optionally substituted indazolyl, an optionally substituted benzoxazolyl, an optionally substituted benzofuryl, an optionally substituted benzothiazolyl, an optionally substituted indolizinyl, an optionally substituted imidazopyridinyl, an optionally substituted benzoxazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidyl, an optionally substituted pyridopyrimidyl, an optionally substituted pyrazolo[3,4]pyrimidyl or an optionally substituted benzo(b)thienyl.

In another embodiment, in the compounds represented by formula (V), $R_{12}$ is an optionally substituted phenyl, an optionally substituted tetrazolyl, or an optionally substituted pyridinyl.

In another embodiment, in the compounds represented by formula (V), $R_{12}$ is an optionally substituted phenyl or an optionally substituted pyridinyl.

In another embodiment, in the compounds represented by formula (I), (II), or (VI), $R_{12}$ is substituted with one or more substituents selected from the group consisting of a lower alkyl, a halo, cyano, nitro, a lower haloalkyl, a lower alkoxy, a lower sulfanylalkyl, —S(O)$_p$R$_{31}$, —S(O)$_p$NR$_{29}$R$_{30}$, —NR$_{29}$R$_{30}$, —C(O)R$_{28}$, —C(O)OR$_{28}$, —C(O)NR$_{29}$R$_{30}$, —NR$_{29}$C(O)R$_{30}$, —NR$_{29}$C(O)OR$_{28}$, —NR$_{28}$C(O)NR$_{29}$R$_{30}$, —OC(O)R$_{28}$, —OC(O)OR$_{28}$, and —OC(O)NR$_{29}$R$_{30}$; wherein p is defined as above; $R_{28}$, $R_{29}$, $R_{30}$, for each occurrence are, independently, H or a lower alkyl; and $R_{31}$, for each occurrence, is independently a lower alkyl.

In another embodiment, in the compounds represented by formula (V), $R_{12}$ is substituted with one or more substituents selected from the group consisting of a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl.

In another embodiment, in the compounds represented by formula (V), $R_{13}$ is an optionally substituted aryl or an optionally substituted heteroaryl.

In another embodiment, in the compounds represented by formula (V), $R_{13}$ is an optionally substituted phenyl or an optionally substituted 5-membered heteroaryl. In one aspect of this embodiment, $R_{13}$ is an optionally substituted 5-membered heteroaryl. Examples of optionally substituted 5-membered heteroaryl groups include an optionally substituted furyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted pyrazolyl, an optionally substituted isothiazolyl, an optionally substituted pyrazinyl, an optionally substituted triazinyl, an optionally substituted triazolyl, an optionally substituted thiadiazolyl, and an optionally substituted tetrazolyl.

In another embodiment, in the compounds represented by formula (V), $R_{13}$ is an optionally substituted phenyl or an optionally substituted 6-membered heteroaryl. In one aspect of this embodiment, $R_{13}$ is an optionally substituted 6-membered heteroaryl. Examples of optionally substituted 6-membered heteroaryl groups include an optionally substituted pyridyl, an optionally substituted pyridazinyl, an optionally substituted pyrimidinyl, an optionally substituted pyrazinyl, or an optionally substituted triazinyl. In another aspect of this embodiment, $R_{13}$ is unsubstituted. In another aspect of this embodiment, $R_{13}$ is substituted with one substituent, for example, $R_{13}$ is substituted with a substituent that is ortho to its point of attachment to L or —NR—C(O)—. In another aspect of this embodiment, $R_{13}$ is substituted with two substituent, for example, $R_{13}$ is substituted with two substituent that ar ortho to its point of attachment to L or —NR—C(O)—.

In another embodiment, in the compounds represented by formula (V), $R_{13}$ is an optionally substituted heteroaryl selected from the group consisting of an optionally substituted indolizinyl, an optionally substituted quinolinyl, an optionally substituted isoquniolinyl, an optionally substituted indazolyl, an optionally substituted benzoxazolyl, an optionally substituted benzofuryl, an optionally substituted benzothiazolyl, an optionally substituted indolizinyl, an optionally substituted imidazopyridinyl, an optionally substituted benzoxazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidyl, an optionally substituted pyridopyrimidyl, an optionally substituted pyrazolo[3,4]pyrimidyl or an optionally substituted benzo(b)thienyl.

In another embodiment, in the compounds represented by formula (V), $R_{13}$ is an optionally substituted phenyl or an optionally substituted pyridinyl.

In another embodiment, in the compounds represented by formula (V), $R_{13}$ is an optionally substituted cycloalkyl or an optionally substituted cycloalkenyl.

In another embodiment, in the compounds represented by formula (V), $R_{13}$ is substituted with one or more substituents selected from the group consisting of a lower alkyl, a halo, cyano, nitro, a lower haloalkyl, a lower alkoxy, a lower sulfanylalkyl, —S(O)$_p$R$_{31}$, —S(O)$_p$NR$_{29}$R$_{30}$, —NR$_{29}$R$_{30}$, —C(O)R$_{28}$, —C(O)OR$_{28}$, —C(O)NR$_{29}$R$_{30}$, —NR$_{29}$C(O) R$_{30}$, —NR$_{29}$C(O)OR$_{28}$, —NR$_{28}$C(O)NR$_{29}$R$_{30}$, —OC(O) R$_{28}$, —OC(O)OR$_{28}$, and —OC(O)NR$_{29}$R$_{30}$; wherein p is defined as above; $R_{28}$, $R_{29}$, $R_{30}$, for each occurrence are, independently, H or a lower alkyl; and $R_{31}$, for each occurrence, is independently a lower alkyl.

In another embodiment, in the compounds represented by formula (V), $R_{13}$ is substituted with one or more substituents selected from the group consisting of a halo or a lower alkyl.

In another embodiment, in the compounds represented by formula (V), $R_{13}$ is 2,6-difluorophenyl, 3-fluoropyridin-4-yl, or 3-methyl-pyridin-4-yl.

In another embodiment, in the compounds represented by formula (III) or (VII), $X_1$ and $X_2$ are CH.

In another embodiment, in the compounds represented by formula (III) or (VII), $X_1$ and $X_2$ are N.

In another embodiment, in the compounds represented by formula (III) or (VII), $X_1$ is CH and $X_2$ is N.

In another embodiment, in the compounds represented by formula (III) or (VII), $X_1$ is N and $X_2$ are CH.

In another embodiment, in the compounds represented by formula (III) or (VII), q is zero.

In another embodiment, in the compounds represented by formula (III) or (VII), q is 1.

In another embodiment, in the compounds represented by formula (III) or (VII), q is 2.

In another embodiment, in the compounds represented by formula (III) or (VII), t is zero.

In another embodiment, in the compounds represented by formula (III) or (VII), t is 1.

In another embodiment, in the compounds represented by formula (III) or (VII), t is 2.

In another embodiment, in the compounds represented by formula (III) or (VII), q is 1 and $R_4$ is a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl.

In another embodiment, in the compounds represented by formula (III) or (VII), q is 2 and $R_4$, for each occurrence, is independently, a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl.

In another embodiment, in the compounds represented by formula (III) or (VII), t is 1 and $R_3$ is a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl. In one aspect of this embodiment, $R_3$ is ortho to the point of attachment to the pyrazine or pyridazine ring.

In another embodiment, in the compounds represented by formula (III) or (VII), t is 1 and $R_3$ is a halo or a lower alkyl. In one aspect of this embodiment, $R_3$ is ortho to the point of attachment to the pyrazine or pyridazine ring.

In another embodiment, in the compounds represented by formula (III) or (VII), t is 2 and $R_3$, for each occurrence, is, independently, a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl. In one aspect of this embodiment, both $R_3$ groups are ortho to the point of attachment to the pyrazine or pyridazine ring.

In another embodiment, in the compounds represented by formula (III) or (VII), t is 2 and $R_3$, for each occurrence, is, independently, a halo or a lower alkyl. In one aspect of this embodiment, both $R_3$ groups are ortho to the point of attachment to the pyrazine or pyridazine ring.

In another embodiment, in the compounds represented by formula (III) or (VII), q is 1 and $R_4$ is a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl. In one aspect of this embodiment, $R_4$ is ortho to the point of attachment to the pyrazine or pyridazine ring.

In another embodiment, in the compounds represented by formula (III) or (VII), q is 2 and $R_4$, for each occurrence, is, independently, a halo, a lower alkyl, a lower haloalkyl, a lower alkoxy, a 5-membered heteroaryl (e.g., tetrazol-5-yl, 1-methyl-tetrazol-5-yl, furan-2-yl, furan-3-yl, oxazol-2-yl, and 3-methyl-[1,2,4]oxadiazol-5-yl), —C(O)H, —C(O)OR$_{28}$, —C(O)R$_{28}$, and —C(O)NR$_{29}$R$_{30}$; wherein $R_{28}$, $R_{29}$, $R_{30}$, for each occurrence are, independently, H or a lower alkyl. In one aspect of this embodiment, the two $R_4$ groups are para to each other.

In another embodiment, in the compounds represented by formula (IV) or (VIII), $X_6$ and $X_7$ are CH.

In another embodiment, in the compounds represented by formula (XI), or (XIV), $X_6$ is CH.

In another embodiment, in the compounds represented by formula (IV) or (VIII), $X_6$ and $X_7$ are N.

In another embodiment, in the compounds represented by formula (XI), or (XIV), $X_6$ is N.

In another embodiment, in the compounds represented by formula (IV) or (VIII), $X_6$ is CH and $X_7$ is N.

In another embodiment, in the compounds represented by formula (IV) or (VIII), $X_6$ is N and $X_7$ are CH.

In another embodiment, in the compounds represented by formula (IV) or (VIII), $R_8$ and $R_9$ are each, independently, a halo or a lower alkyl.

In another embodiment, in the compounds represented by formula (IV) or (VIII), $R_8$ and $R_9$ are each fluoro.

In another embodiment, in the compounds represented by formula (IV), (VIII), (XI), or (XIV), $R_{10}$ and $R_{11}$, are each, independently, a halo, cyano, —CH$_3$, —CH$_2$CH$_3$, —CH$_2$CH$_2$CH$_3$, —OCH$_3$, —CF$_3$, tetrazol-5-yl, 1-methyl-tetrazol-5-yl, —C(O)OCH$_3$, —C(O)OCH$_2$CH$_3$, —C(O)OCH$_2$CH$_2$CH$_3$, —C(O)NH$_2$, furan-2-yl, furan-3-yl, oxazol-2-yl, [1,2,4]oxadiazol-5-yl, 3-methyl-oxadiazol-5-yl, or tetrazol-5-yl.

In another embodiment, the invention relates to compounds selected from the group consisting of:
N-[5-(2-Chloro-5-trifluoromethyl-phenyl)-pyrazin-2-yl]-2,6-difluoro-benzamide;
N-[5-(2-Chloro-5-trifluoromethyl-phenyl)-pyrazin-2-yl]-3-fluoro-isonicotinamide;
N-[5-(2-Chloro-5-trifluoromethyl-phenyl)-pyrazin-2-yl]-3-methyl-isonicotinamide;
N-[5-(2-Chloro-5-trifluoromethyl-phenyl)-pyrazin-2-yl]-2,6-difluoro-benzamide hydrochloride;
2,6-Difluoro-N-{5-[2-methyl-5-(1-methyl-1H-tetrazol-5-yl)-phenyl]-pyrazin-2-yl}-benzamide;

3-[5-(2,6-Difluoro-benzoylamino)-pyrazin-2-yl]-4-methyl-benzoic acid methyl ester;
4-Methyl-3-{5-[(3-methyl-pyridine-4-carbonyl)-amino]-pyrazin-2-yl}-benzoic acid methyl ester;
3-[5-(2,6-Difluoro-benzoylamino)-pyrazin-2-yl]-4-methyl-benzoic acid propyl ester;
3-[5-(2,6-Difluoro-benzoylamino)-pyrazin-2-yl]-4-methyl-benzoic acid 2-methoxy-ethyl ester;
4-Chloro-3-[5-(2,6-difluoro-benzoylamino)-pyrazin-2-yl]-benzoic acid methyl ester;
4-Chloro-3-[5-(2,6-difluoro-benzoylamino)-pyrazin-2-yl]-benzoic acid ethyl ester;
4-Chloro-3-[5-(2,6-difluoro-benzoylamino)-pyrazin-2-yl]-benzoic acid 2-methoxy-ethyl ester;
2,6-Difluoro-N-[5-(5-furan-2-yl-2-methoxy-pyridin-3-yl)-pyrazin-2-yl]-benzamide;
2,6-Difluoro-N-[5-(5-furan-3-yl-2-methoxy-pyridin-3-yl)-pyrazin-2-yl]-benzamide;
N-[5-(5-Chloro-2-methoxy-pyridin-3-yl)-pyrazin-2-yl]-2,6-difluoro-benzamide;
N-[5-(5-Bromo-2-methoxy-pyridin-3-yl)-pyrazin-2-yl]-2,6-difluoro-benzamide;
N-[5-(2-Ethyl-5-trifluoromethyl-phenyl)-pyrazin-2-yl]-2,6-difluoro-benzamide;
3-[5-(2,6-Difluoro-benzoylamino)-pyrazin-2-yl]-4-methyl-benzamide;
4-[5-(2,6-Difluoro-benzoylamino)-pyrazin-2-yl]-3-methyl-benzoic acid methyl ester;
4-[5-(2,6-Difluoro-benzoylamino)-pyrazin-2-yl]-3-methyl-benzoic acid ethyl ester;
4-[5-(2,6-Difluoro-benzoylamino)-pyrazin-2-yl]-3-methyl-benzoic acid 2-methoxy-ethyl ester;
3-Chloro-4-[5-(2,6-difluoro-benzoylamino)-pyrazin-2-yl]-benzoic acid methyl ester;
3-Chloro-4-[5-(2,6-difluoro-benzoylamino)-pyrazin-2-yl]-benzoic acid ethyl ester;
3-Chloro-4-[5-(2,6-difluoro-benzoylamino)-pyrazin-2-yl]-benzoic acid 2-methoxy-ethyl ester;
3-Fluoro-N-[5-(5-furan-2-yl-2-methoxy-pyridin-3-yl)-pyrazin-2-yl]-isonicotinamide;
3-Fluoro-N-[5-(5-furan-3-yl-2-methoxy-pyridin-3-yl)-pyrazin-2-yl]-isonicotinamide;
N-[5-(5-Chloro-2-methoxy-pyridin-3-yl)-pyrazin-2-yl]-3-fluoro-isonicotinamide;
N-[5-(5-Bromo-2-methoxy-pyridin-3-yl)-pyrazin-2-yl]-3-fluoro-isonicotinamide;
3-Fluoro-N-[5-(2-methyl-5-trifluoromethyl-phenyl)-pyrazin-2-yl]-sonicotinamide;
N-[5-(5-Carbamoyl-2-methyl-phenyl)-pyrazin-2-yl]-3-fluoro-isonicotinamide;
N-[5-(5-Cyano-2-methyl-phenyl)-pyrazin-2-yl]-3-fluoro-isonicotinamide;
3-{5-[(3,5-Difluoro-pyridine-4-carbonyl)-amino]-pyrazin-2-yl}-4-methyl-enzoic acid methyl ester;
3-{5-[(3,5-Difluoro-pyridine-4-carbonyl)-amino]-pyrazin-2-yl}-4-methyl-benzoic acid ethyl ester;
3-{5-[(3,5-Difluoro-pyridine-4-carbonyl)-amino]-pyrazin-2-yl}-4-methyl-benzoic acid 2-methoxy-ethyl ester;
4-Chloro-3-{5-[(3,5-difluoro-pyridine-4-carbonyl)-amino]-pyrazin-2-yl}-benzoic acid methyl ester;
4-Chloro-3-{5-[(3,5-difluoro-pyridine-4-carbonyl)-amino]-pyrazin-2-yl}-benzoic acid ethyl ester;
4-Chloro-3-{5-[(3,5-difluoro-pyridine-4-carbonyl)-amino]-pyrazin-2-yl}-benzoic acid 2-methoxy-ethyl ester;
3,5-Difluoro-N-[5-(5-furan-2-yl-2-methoxy-pyridin-3-yl)-pyrazin-2-yl]-iso nicotinamide;
3,5-Difluoro-N-[5-(5-furan-3-yl-2-methoxy-pyridin-3-yl)-pyrazin-2-yl]-isonicotinamide;
N-[5-(5-Chloro-2-methoxy-pyridin-3-yl)-pyrazin-2-yl]-3,5-difluoro-isonicotinamide;
N-[5-(5-Bromo-2-methoxy-pyridin-3-yl)-pyrazin-2-yl]-3,5-difluoro-isonicotinamide;
N-[5-(2-Ethyl-5-trifluoromethyl-phenyl)-pyrazin-2-yl]-3,5-difluoro-isonicotinamide;
N-[5-(5-Carbamoyl-2-methyl-phenyl)-pyrazin-2-yl]-3,5-difluoro-isonicotinamide;
3,5-Difluoro-N-[5-(5-isocyano-2-methyl-phenyl)-pyrazin-2-yl]-isonicotinamide;
4-Methyl-3-{5-[(3-methyl-pyridine-4-carbonyl)-amino]-pyrazin-2-yl}-benzoic acid ethyl ester;
4-Methyl-3-{5-[(3-methyl-pyridine-4-carbonyl)-amino]-pyrazin-2-yl}-benzoic acid 2-methoxy-ethyl ester;
4-Chloro-3-{5-[(3-methyl-pyridine-4-carbonyl)-amino]-pyrazin-2-yl}-benzoic acid methyl ester;
4-Chloro-3-{5-[(3-methyl-pyridine-4-carbonyl)-amino]-pyrazin-2-yl}-benzoic acid ethyl ester;
4-Chloro-3-{5-[(3-methyl-pyridine-4-carbonyl)-amino]-pyrazin-2-yl}-benzoic acid 2-methoxy-ethyl ester;
N-[5-(2-Chloro-5-furan-2-yl-phenyl)-pyrazin-2-yl]-3-methyl-isonicotinamide;
N-[5-(2-Chloro-5-furan-3-yl-phenyl)-pyrazin-2-yl]-3-methyl-isonicotinamide;
N-[5-(5-Chloro-2-methoxy-pyridin-3-yl)-pyrazin-2-yl]-3-methyl-isonicotinamide;
N-[5-(5-Bromo-2-methoxy-pyridin-3-yl)-pyrazin-2-yl]-3-methyl-isonicotinamide;
N-[5-(2-Ethyl-5-trifluoromethyl-phenyl)-pyrazin-2-yl]-3-methyl-isonicotinamide;
N-[5-(5-Carbamoyl-2-methyl-phenyl)-pyrazin-2-yl]-3-methyl-isonicotinamide;
N-[5-(5-Cyano-2-methyl-phenyl)-pyrazin-2-yl]-3-methyl-isonicotinamide;
2,6-Difluoro-N-[5-(2-methyl-5-oxazol-2-yl-phenyl)-pyrazin-2-yl]-benzamide;
2,6-Difluoro-N-{5-[2-methyl-5-(3-methyl-[1,2,4]oxadiazol-5-yl)-phenyl]-pyrazin-2-yl}-benzamide;
2,6-Difluoro-N-{5-[2-methyl-5-(1H-tetrazol-5-yl)-phenyl]-pyrazin-2-yl}-benzamide;
3-Fluoro-N-[5-(2-methyl-5-oxazol-2-yl-phenyl)-pyrazin-2-yl]-isonicotinamide;
3-Methyl-N-[5-(2-methyl-5-oxazol-2-yl-phenyl)-pyrazin-2-yl]-isonicotinamide;
3,5-Difluoro-N-[5-(2-methyl-5-oxazol-2-yl-phenyl)-pyrazin-2-yl]-isonicotinamide;
4-Methyl-[1,2,3]thiadiazole-5-carboxylic acid [5-(2-methyl-5-oxazol-2-yl-phenyl)-pyrazin-2-yl]-amide;
3-Fluoro-N-[5-(2-methyl-5-thiazol-2-yl-phenyl)-pyrazin-2-yl]-isonicotinamide;
3-Methyl-N-[5-(2-methyl-5-thiazol-2-yl-phenyl)-pyrazin-2-yl]-isonicotinamide;
3,5-Difluoro-N-[5-(2-methyl-5-thiazol-2-yl-phenyl)-pyrazin-2-yl]-isonicotinamide;
4-Methyl-[1,2,3]thiadiazole-5-carboxylic acid [5-(2-methyl-5-thiazol-2-yl-phenyl)-pyrazin-2-yl]-amide;
N-[5-(2-Chloro-5-oxazol-2-yl-phenyl)-pyrazin-2-yl]-3-fluoro-isonicotinamide;
N-[5-(2-Chloro-5-oxazol-2-yl-phenyl)-pyrazin-2-yl]-3-methyl-isonicotinamide;
N-[5-(2-Chloro-5-oxazol-2-yl-phenyl)-pyrazin-2-yl]-3,5-difluoro-isonicotinamide;
4-Methyl-[1,2,3]thiadiazole-5-carboxylic acid [5-(2-chloro-5-oxazol-2-yl-phenyl)-pyrazin-2-yl]-amide;

3-Fluoro-N-[5-(2-methyl-5-[1,3,4]oxadiazol-2-yl-phenyl)-pyrazin-2-yl]-isonicotinamide;
3-Methyl-N-[5-(2-methyl-5-[1,3,4]oxadiazol-2-yl-phenyl)-pyrazin-2-yl]-isonicotinamide;
3,5-Difluoro-N-[5-(2-methyl-5-[1,3,4]oxadiazol-2-yl-phenyl)-pyrazin-2-yl]-isonicotinamide;
4-Methyl-[1,2,3]thiadiazole-5-carboxylic acid [5-(2-methyl-5-[1,3,4]oxadiazol-2-yl-phenyl)-pyrazin-2-yl]-amide;
3-Fluoro-N-[5-(2-methyl-5-[1,3,4]thiadiazol-2-yl-phenyl)-pyrazin-2-yl]-isonicotinamide;
3-Methyl-N-[5-(2-methyl-5-[1,3,4]thiadiazol-2-yl-phenyl)-pyrazin-2-yl]-isonicotinamide;
3,5-Difluoro-N-[5-(2-methyl-5-[1,3,4]thiadiazol-2-yl-phenyl)-pyrazin-2-yl]-isonicotinamide;
4-Methyl-[1,2,3]thiadiazole-5-carboxylic acid [5-(2-methyl-5-[1,3,4]thiadiazol-2-yl-phenyl)-pyrazin-2-yl]-amide;
N-[5-(2-Chloro-5-[1,3,4]oxadiazol-2-yl-phenyl)-pyrazin-2-yl]-3-fluoro-isonicotinamide;
N-[5-(2-Chloro-5-[1,3,4]oxadiazol-2-yl-phenyl)-pyrazin-2-yl]-3-methyl-isonicotinamide;
N-[5-(2-Chloro-5-[1,3,4]oxadiazol-2-yl-phenyl)-pyrazin-2-yl]-3,5-difluoro-isonicotinamide;
4-Methyl-[1,2,3]thiadiazole-5-carboxylic acid [5-(2-chloro-5-[1,3,4]oxadiazol-2-yl-phenyl)-pyrazin-2-yl]-amide;
3-Fluoro-N-[5-(2-methyl-5-oxazol-5-yl-phenyl)-pyrazin-2-yl]-isonicotinamide;
3-Methyl-N-[5-(2-methyl-5-oxazol-5-yl-phenyl)-pyrazin-2-yl]-isonicotinamide;
3,5-Difluoro-N-[5-(2-methyl-5-oxazol-5-yl-phenyl)-pyrazin-2-yl]-isonicotinamide;
4-Methyl-[1,2,3]thiadiazole-5-carboxylic acid [5-(2-methyl-5-oxazol-5-yl-phenyl)-pyrazin-2-yl]-amide;
3-Fluoro-N-[5-(2-methyl-5-thiazol-5-yl-phenyl)-pyrazin-2-yl]-isonicotinamide;
3-Methyl-N-[5-(2-methyl-5-thiazol-5-yl-phenyl)-pyrazin-2-yl]-isonicotinamide;
3,5-Difluoro-N-[5-(2-methyl-5-thiazol-5-yl-phenyl)-pyrazin-2-yl]-isonicotinamide;
4-Methyl-[1,2,3]thiadiazole-5-carboxylic acid [5-(2-methyl-5-thiazol-5-yl-phenyl)-pyrazin-2-yl]-amide;
N-[5-(2-Chloro-5-oxazol-5-yl-phenyl)-pyrazin-2-yl]-3-fluoro-isonicotinamide;
N-[5-(2-Chloro-5-oxazol-5-yl-phenyl)-pyrazin-2-yl]-3-methyl-isonicotinamide;
N-[5-(2-Chloro-5-oxazol-5-yl-phenyl)-pyrazin-2-yl]-3,5-difluoro-isonicotinamide;
4-Methyl-[1,2,3]thiadiazole-5-carboxylic acid [5-(2-chloro-5-oxazol-5-yl-phenyl)-pyrazin-2-yl]-amide;
3-Fluoro-N-[5-(5-isoxazol-5-yl-2-methyl-phenyl)-pyrazin-2-yl]-isonicotinamide;
N-[5-(5-Isoxazol-5-yl-2-methyl-phenyl)-pyrazin-2-yl]-3-methyl-isonicotinamide;
3,5-Difluoro-N-[5-(5-isoxazol-5-yl-2-methyl-phenyl)-pyrazin-2-yl]-isonicotinamide;
4-Methyl-[1,2,3]thiadiazole-5-carboxylic acid [5-(5-isoxazol-5-yl-2-methyl-phenyl)-pyrazin-2-yl]-amide;
3-Fluoro-N-[5-(5-isothiazol-5-yl-2-methyl-phenyl)-pyrazin-2-yl]-isonicotinamide;
N-[5-(5-Isothiazol-5-yl-2-methyl-phenyl)-pyrazin-2-yl]-3-methyl-isonicotinamide;
3,5-Difluoro-N-[5-(5-isothiazol-5-yl-2-methyl-phenyl)-pyrazin-2-yl]-isonicotinamide;
4-Methyl-[1,2,3]thiadiazole-5-carboxylic acid [5-(5-isothiazol-5-yl-2-methyl-phenyl)-pyrazin-2-yl]-amide;
N-[5-(2-Chloro-5-isoxazol-5-yl-phenyl)-pyrazin-2-yl]-3-fluoro-isonicotinamide;
N-[5-(2-Chloro-5-isoxazol-5-yl-phenyl)-pyrazin-2-yl]-3-methyl-isonicotinamide;
N-[5-(2-Chloro-5-isoxazol-5-yl-phenyl)-pyrazin-2-yl]-3,5-difluoro-isonicotinamide;
4-Methyl-[1,2,3]thiadiazole-5-carboxylic acid [5-(2-chloro-5-isoxazol-5-yl-phenyl)-pyrazin-2-yl]-amide;
3-{5-[(3-Fluoro-pyridine-4-carbonyl)-amino]-pyrazin-2-yl}-4-methyl-benzoic acid methyl ester;
N-[5-(2,5-Dimethoxy-phenyl)-pyrazin-2-yl]-2,6-difluoro-benzamide;
N-[5-(2-Chloro-5-trifluoromethyl-phenyl)-pyrazin-2-yl]-2-methyl-nicotinamide;
Cyclohexanecarboxylic acid [5-(2-chloro-5-trifluoromethyl-phenyl)-pyrazin-2-yl]-amide;
N-[5-(2,5-Dimethoxy-phenyl)-pyrazin-2-yl]-3-fluoro-isonicotinamide;
4-Methyl-[1,2,3]thiadiazole-5-carboxylic acid [5-(2-chloro-5-trifluoromethyl-phenyl)-pyrazin-2-yl]-amide;
N-[5-(2-Chloro-5-trifluoromethyl-phenyl)-pyrazin-2-yl]-3,5-difluoro-isonicotinamide;
N-[5-(2,5-Dimethoxy-phenyl)-pyrazin-2-yl]-3-methyl-isonicotinamide;
N-[5-(2,5-Dimethoxy-phenyl)-pyrazin-2-yl]-3,5-difluoro-isonicotinamide;
4-Methyl-[1,2,3]thiadiazole-5-carboxylic acid [5-(2,5-dimethoxy-phenyl)-pyrazin-2-yl]-amide;
Cyclohexanecarboxylic acid [5-(2,5-dimethoxy-phenyl)-pyrazin-2-yl]-amide;
Cyclohexanecarboxylic acid [5-(2-methyl-5-oxazol-2-yl-phenyl)-pyrazin-2-yl]-amide; and
pharmaceutically acceptable salts, solvates, clathrates, or prodrugs thereof.

In another embodiment, the invention relates to N-[6-(2-chloro-5-trifluoromethyl-phenyl)-pyridazin-3-yl]-2,6-difluoro-benzamide, and a pharmaceutically acceptable salt, solvate, clathrate, or prodrug thereof.

In another embodiment, the invention relates to N-[5-(2-Chloro-5-trifluoromethyl-phenyl)-pyrimidin-2-yl]-2,6-difluoro-benzamide, N-[2-(2-Chloro-5-trifluoromethyl-phenyl)-pyrimidin-5-yl]-2,6-difluoro-benzamide, and a pharmaceutically acceptable salt, solvate, clathrate, or prodrug thereof.

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values for variables (e.g., values shown in the exemplary compounds disclosed herein) in any chemical formula disclosed herein can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features, embodiments or substituents.

In another embodiment, the invention relates to pharmaceutical compositions that comprise a compound of any one of formulas (I) through (XIV), or Table 1, or a pharmaceutically acceptable salt, solvate, clathrate, or prodrug thereof, as an active ingredient, and a pharmaceutically acceptable carrier or vehicle. The compositions are useful for immunosuppression or to treat or prevent inflammatory conditions, allergic conditions and immune disorders.

In another embodiment, the invention relates to methods for immunosuppression or for treating or preventing inflammatory conditions, immune disorders, or allergic disorders in a patient in need thereof comprising administering an effective amount of a compound represented by any one of formulas (I) through (XIV), or Table 1, or a pharmaceutically acceptable salt, solvate, clathrate, or prodrug thereof.

In another embodiment, the invention relates to methods for immunosuppression or for treating or preventing inflammatory conditions, immune disorders, or allergic disorders in a patient in need thereof comprising administering an effective amount of a pharmaceutical composition that comprises a compound represented by any one of formulas (I) through (XIV), or Table 1, or a pharmaceutically acceptable salt, solvate, clathrate, or prodrug thereof.

In another embodiment, compounds of any one of formulas (I) through (XIV), or Table 1, or a pharmaceutically acceptable salt, solvate, clathrate, or prodrug thereof, are particularly useful inhibiting immune cell (e.g., T-cells and/or B-cells) activation (e.g., activation in response to an antigen) and/or T cell and/or B cell proliferation. Indicators of immune cell activation include secretion of IL-2 by T cells, proliferation of T cells and/or B cells, and the like. In one embodiment, immune cell activation and/or T cell and/or B cell proliferation is inhibited in a mammal (e.g., a human), by administering to the mammal (e.g., human) a compound of any one of formulas (I) through (XIV) or Table 1, or a pharmaceutically acceptable salt, solvate, clathrate, or prodrug thereof.

In another embodiment, compounds of any one of formula (I) through (XIV), or Table 1, or a pharmaceutically acceptable salt, solvate, clathrate, or prodrug thereof, can inhibit the production of certain cytokines that regulate immune cell activation. For example, compounds of any one of formulas (I) through (XIV), or Table 1, or a pharmaceutically acceptable salt, solvate, clathrate, or prodrug thereof, can inhibit the production of IL-2, IL-4, IL-5, IL-13, GM-CSF, IFN-γ, TNF-α and combinations thereof. In one embodiment, cytokine production is inhibited in a mammal (e.g., a human), by administering to the mammal (e.g., human) a compound of any one of formulas (I) through (XIV) or Table 1, or a pharmaceutically acceptable salt, solvate, clathrate, or prodrug thereof.

In another embodiment, compounds of any one of formulas (I) through (XIV), or Table 1, or a pharmaceutically acceptable salt, solvate, clathrate, or prodrug thereof, can modulate the activity of one or more ion channel, such as CRAC ion channels, involved in activation of immune cells. In one embodiment, a compound of any one of formulas (I) through (XIV) or Table 1 can inhibit the influx of calcium ions into an immune cell (e.g., T cells, B cells, and/or mast cells) by inhibiting the action of CRAC ion channels. In general, a decrease in $I_{CRAC}$ current upon contacting a cell with a compound is one indicator that the compound inhibitions CRAC ion channels. $I_{CRAC}$ current can be measured, for example, using a patch clamp technique, which is described in more detail in the examples below. In one embodiment, a compound of any one of formulas (I) through (XIV) or Table 1 modulates an ion channel in a mammal (e.g., a human). In one embodiment, the activity of one or more ion channels is inhibited in a mammal (e.g., a human), by administering to the mammal (e.g., human) a compound of any one of formulas (I) through (XIV) or Table 1, or a pharmaceutically acceptable salt, solvate, clathrate, or prodrug thereof.

In another embodiment, compounds of any one of formula (I) through (XIV), or Table 1, or a pharmaceutically acceptable salt, solvate, clathrate, or prodrug thereof, can inhibit degranulation of mast cell. Inhibition of mast cell degranulation can determined as described in the experimental section herein or by any method known to those skilled in the art. In one embodiment, mast cell degranulation is inhibited in a mammal (e.g., a human), by administering to the mammal (e.g., human) a compound of any one of formulas (I) through (XIV) or Table 1, or a pharmaceutically acceptable salt, solvate, clathrate, or prodrug thereof.

Exemplary Compounds of the Invention

Exemplary compounds of the invention are depicted in Table 1 below.

TABLE 1

| Compound No. | Structure | Chemical Name |
|---|---|---|
| 1 | 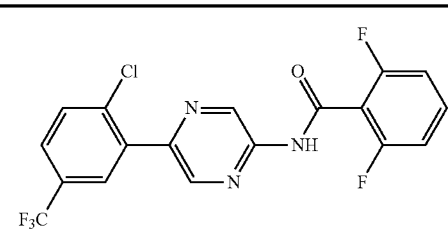 | N-[-(2-Chloro-5-trifluoromethyl-phenyl)-pyrazin-2-yl]-2,6-difluoro-benzamide |
| 2 | 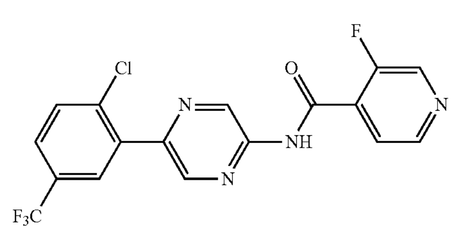 | N-[5-(2-Chloro-5-trifluoromethyl-phenyl)-pyrazin-2-yl]-3-fluoro-isonicotinamide |

TABLE 1-continued

| Compound No. | Structure | Chemical Name |
|---|---|---|
| 3 | 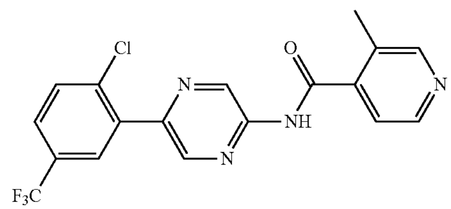 | N-[5-(2-Chloro-5-trifluoro-methyl-phenyl)-pyrazin-2-yl]-3-methyl-isonicotinamide |
| 4 | 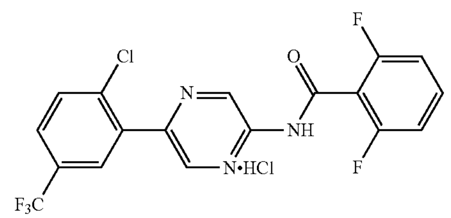 | N-[5-(2-Chloro-5-trifluoro-methyl-phenyl)-pyrazin-2-yl]-2,6-difluoro-benzamid hydrochloride |
| 5 | 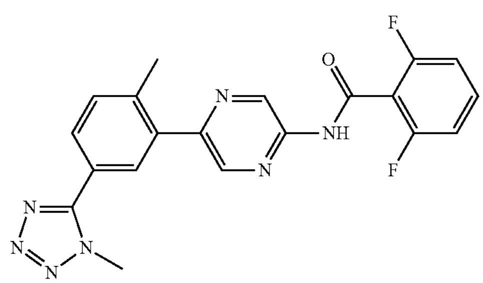 [SMILES: Cc1ccc(-c2nnnn2C)cc1-c1cnc(NC(=O)c2c(F)cccc2F)cn1] | 2,6-Difluoro-N-{5-[2-methyl-5-(1-methyl-1H-tetrazol-5-yl)-phenyl]-pyrazin-2-yl}-benzamide |
| 6 | 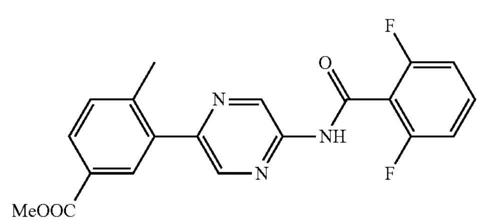 [SMILES: COC(=O)c1ccc(C)c(-c2cnc(NC(=O)c3c(F)cccc3F)cn2)c1] | 3-[5-(2,6-Difluoro-benzoyl-amino)-pyrazin-2-yl]-4-methyl-benzoic acid methyl ester |
| 7 | 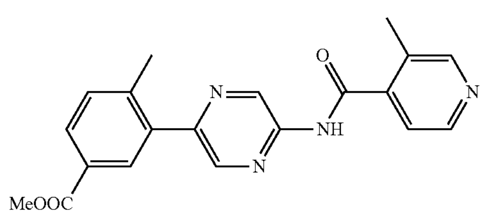 [SMILES: COC(=O)c1ccc(C)c(-c2cnc(NC(=O)c3ccncc3C)cn2)c1] | 4-Methyl-3-{5-[(3-methyl-pyridine-4-carbonyl)-amino]-pyrazin-2-yl}-benzoic acid methyl ester |
| 8 | 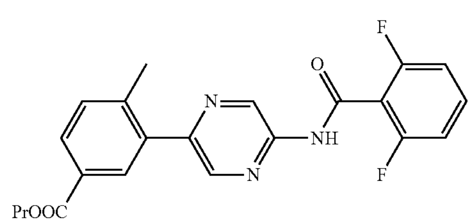 | 3-[5-(2,6-Difluoro-benzoyl-amino)-pyrazin-2-yl]-4-methyl-benzoic acid propyl ester |

TABLE 1-continued

| Compound No. | Structure | Chemical Name |
|---|---|---|
| 9 | 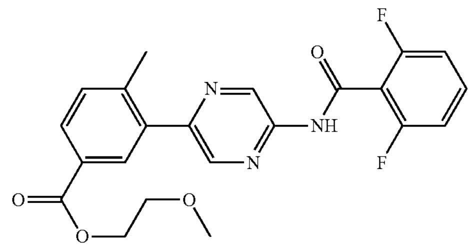 [SMILES: COCCOC(=O)c1ccc(C)c(-c2cnc(NC(=O)c3c(F)cccc3F)cn2)c1] | 3-[5-(2,6-Difluoro-benzoyl-amino)-pyrazin-2-yl]-4-methyl-benzoic acid 2-methoxy-ethyl ester |
| 10 | 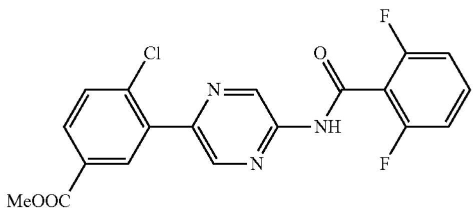 | 4-Chloro-3-[5-(2,6-difluoro-benzoylamino)-pyrazin-2-yl]-benzoic acid methyl ester |
| 11 | 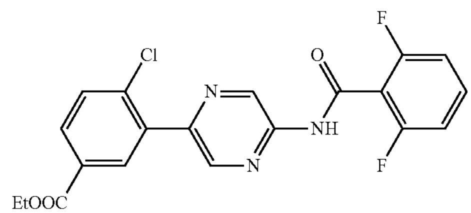 [SMILES: CCOC(=O)c1ccc(Cl)c(-c2cnc(NC(=O)c3c(F)cccc3F)cn2)c1] | 4-Chloro-3-[5-(2,6-difluoro-benzoylamino)-pyrazin-2-yl]-benzoic acid ethyl ester |
| 12 | 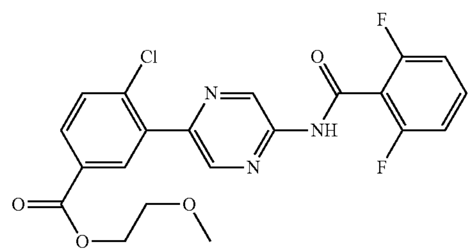 [SMILES: COCCOC(=O)c1ccc(Cl)c(-c2cnc(NC(=O)c3c(F)cccc3F)cn2)c1] | 4-Chloro-3-[5-(2,6-difluoro-benzoylamino)-pyrazin-2-yl]-benzoic acid 2-methoxy-ethyl ester |
| 13 | 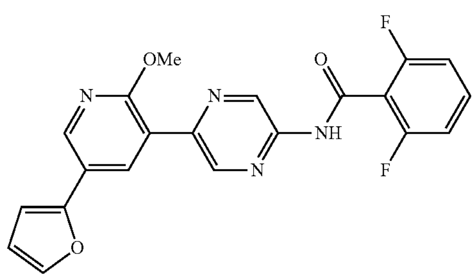 [SMILES: COc1ncc(-c2ccco2)cc1-c1cnc(NC(=O)c2c(F)cccc2F)cn1] | 2,6-Difluoro-N-[5-(5-furan-2-yl-2-methoxy-pyridin-3-yl)-pyrazin-2-yl]-benzamide |
| 14 | 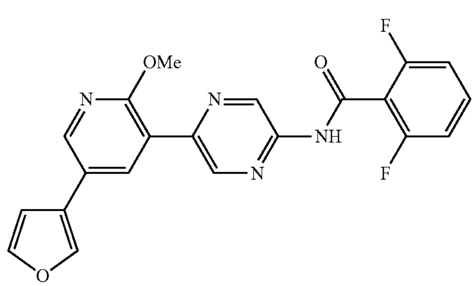 [SMILES: COc1ncc(-c2ccoc2)cc1-c1cnc(NC(=O)c2c(F)cccc2F)cn1] | 2,6-Difluoro-N-[5-(5-furan-3-yl-2-methoxy-pyridin-3-yl)-pyrazin-2-yl]-benzamide |

TABLE 1-continued

| Compound No. | Structure | Chemical Name |
|---|---|---|
| 15 | 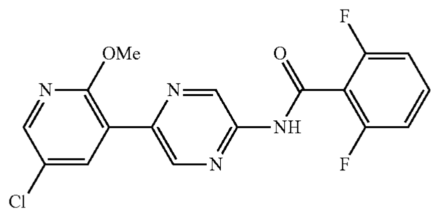 | N-[5-(5-Chloro-2-methoxy-pyridin-3-yl)-pyrazin-2-yl]-2,6-difluoro-benzamide |
| 16 | 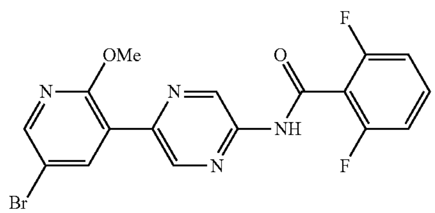 [SMILES: COc1ncc(Cl)cc1-c1cnc(NC(=O)c2c(F)cccc2F)cn1] | N-[5-(5-Bromo-2-methoxy-pyridin-3-yl)-pyrazin-2-yl]-2,6-difluoro-benzamide |
| 17 | 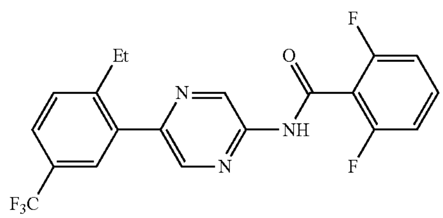 [SMILES: CCc1ccc(C(F)(F)F)cc1-c1cnc(NC(=O)c2c(F)cccc2F)cn1] | N-[5-(2-Ethyl-5-trifluoro-methyl-phenyl)-pyrazin-2-yl]-2,6-difluoro-benzamide |
| 18 | 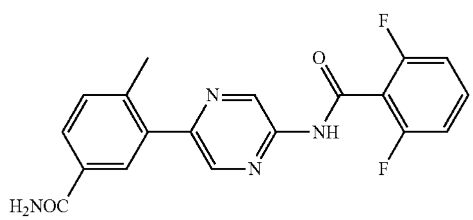 [SMILES: Cc1ccc(C(N)=O)cc1-c1cnc(NC(=O)c2c(F)cccc2F)cn1] | 3-[5-(2,6-Difluoro-benzoyl-amino)-pyrazin-2-yl]-4-methyl-benzamide |
| 19 | 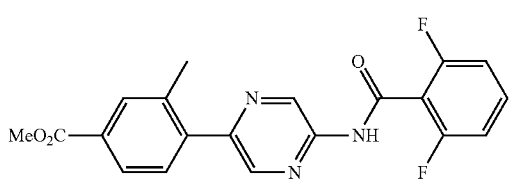 | 4-[5-(2,6-Difluoro-benzoyl-amino)-pyrazin-2-yl]-3-methyl-benzoic acid methyl ester |
| 20 | 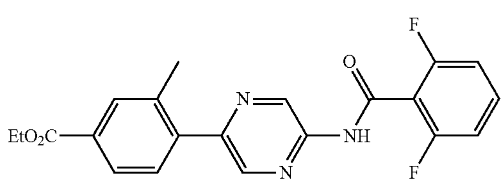 [SMILES: CCOC(=O)c1ccc(-c2cnc(NC(=O)c3c(F)cccc3F)cn2)c(C)c1] | 4-[5-(2,6-Difluoro-benzoyl-amino)-pyrazin-2-yl]-3-methyl-benzoic acid ethyl ester |
| 21 | 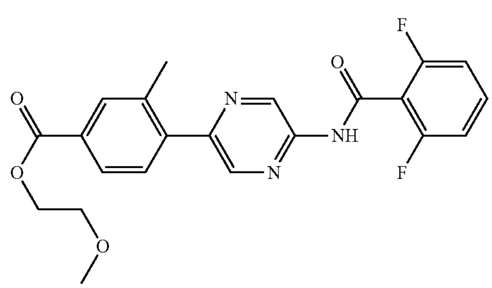 [SMILES: COCCOC(=O)c1ccc(-c2cnc(NC(=O)c3c(F)cccc3F)cn2)c(C)c1] | 4-[5-(2,6-Difluoro-benzoyl-amino)-pyrazin-2-yl]-3-methyl-benzoic acid 2-methoxy-ethyl ester |

TABLE 1-continued

| Compound No. | Structure | Chemical Name |
|---|---|---|
| 22 | 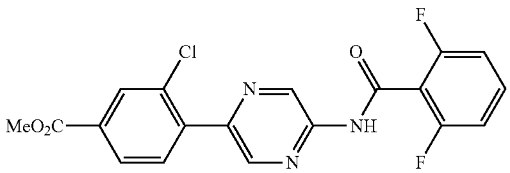 [SMILES: COC(=O)c1ccc(-c2cnc(NC(=O)c3c(F)cccc3F)cn2)c(Cl)c1] | 3-Chloro-4-[5-(2,6-difluoro-benzoylamino)-pyrazin-2-yl]-benzoic acid methyl ester |
| 23 | 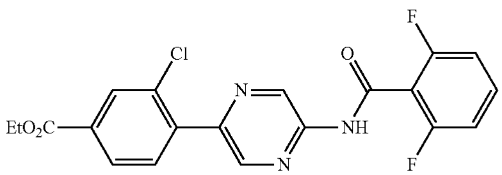 [SMILES: CCOC(=O)c1ccc(-c2cnc(NC(=O)c3c(F)cccc3F)cn2)c(Cl)c1] | 3-Chloro-4-[5-(2,6-difluoro-benzoylamino)-pyrazin-2-yl]-benzoic acid ethyl ester |
| 24 | 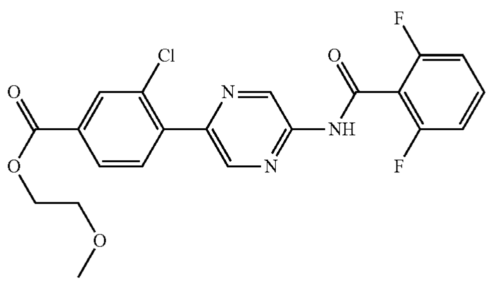 [SMILES: COCCOC(=O)c1ccc(-c2cnc(NC(=O)c3c(F)cccc3F)cn2)c(Cl)c1] | 3-Chloro-4-[5-(2,6-difluoro-benzoylamino)-pyrazin-2-yl]-benzoic acid 2-methoxy-ethyl ester |
| 25 | 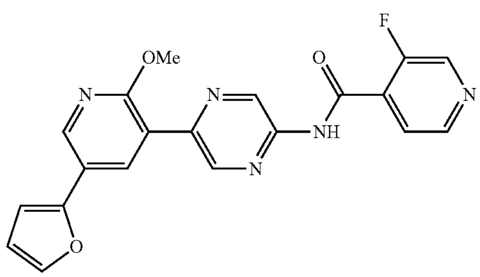 [SMILES: COc1ncc(-c2ccco2)cc1-c1cnc(NC(=O)c2ccncc2F)cn1] | 3-Fluoro-N-[5-(5-furan-2-yl-2-methoxy-pyridin-3-yl)-pyrazin-2-yl]-isonicotinamide |
| 26 | 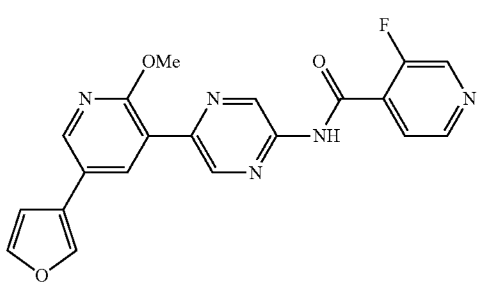 [SMILES: COc1ncc(-c2ccoc2)cc1-c1cnc(NC(=O)c2ccncc2F)cn1] | 3-Fluoro-N-[5-(5-furan-3-yl-2-methoxy-pyridin-3-yl)-pyrazin-2-yl]-isonicotinamide |
| 27 | 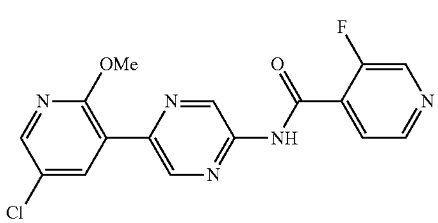 [SMILES: COc1ncc(Cl)cc1-c1cnc(NC(=O)c2ccncc2F)cn1] | N-[5-(5-Chloro-2-methoxy-pyridin-3-yl)-pyrazin-2-yl]-3-fluoro-isonicotinamide |

TABLE 1-continued

| Compound No. | Structure | Chemical Name |
|---|---|---|
| 28 | 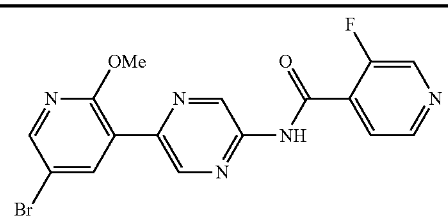 | N-[5-(5-Bromo-2-methoxy-pyridin-3-yl)-pyrazin-2-yl]-3-fluoro-isonicotinamide |
| 29 | 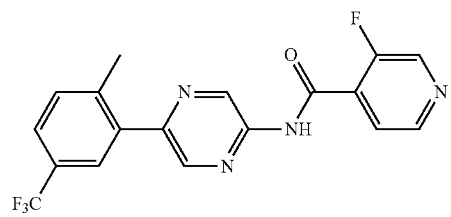 [SMILES: Cc1ccc(C(F)(F)F)cc1-c1cnc(NC(=O)c2ccncc2F)cn1] | 3-Fluoro-N-[5-(2-methyl-5-trifluoromethyl-phenyl)-pyrazin-2-yl]-isonicotinamide |
| 30 | 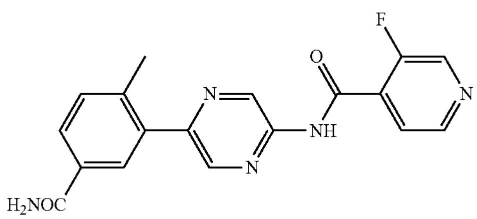 [SMILES: Cc1ccc(C(N)=O)cc1-c1cnc(NC(=O)c2ccncc2F)cn1] | N-[5-(5-Carbamoyl-2-methyl-phenyl)-pyrazin-2-yl]-3-fluoro-isonicotinamide |
| 31 | 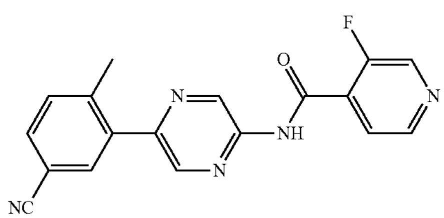 [SMILES: Cc1ccc(C#N)cc1-c1cnc(NC(=O)c2ccncc2F)cn1] | N-[5-(5-Cyano-2-methyl-phenyl)-pyrazin-2-yl]-3-fluoro-isonicotinamide |
| 32 | 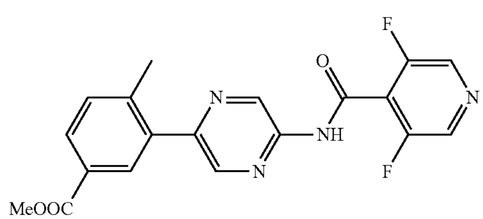 [SMILES: COC(=O)c1ccc(C)c(-c2cnc(NC(=O)c3c(F)cncc3F)cn2)c1] | 3-{5-[(3,5-Difluoro-pyridine-4-carbonyl)-amino]-pyrazin-2-yl}-4-methyl-benzoic acid methyl ester |
| 33 | 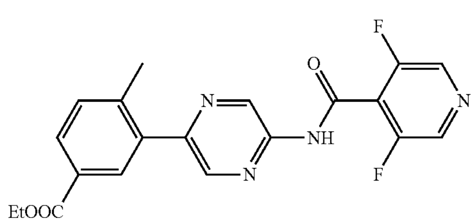 [SMILES: CCOC(=O)c1ccc(C)c(-c2cnc(NC(=O)c3c(F)cncc3F)cn2)c1] | 3-{5-[(3,5-Difluoro-pyridine-4-carbonyl)-amino]-pyrazin-2-yl}-4-methyl-benzoic acid ethyl ester |
| 34 | 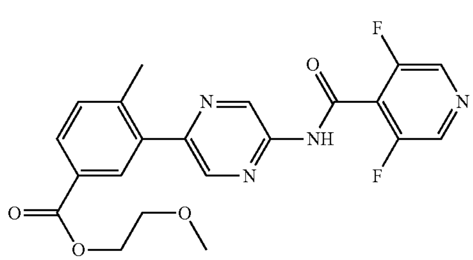 [SMILES: COCCOC(=O)c1ccc(C)c(-c2cnc(NC(=O)c3c(F)cncc3F)cn2)c1] | 3-{5-[(3,5-Difluoro-pyridine-4-carbonyl)-amino]-pyrazin-2-yl}-4-methyl-benzoic acid 2-methoxy-ethyl ester |

TABLE 1-continued

| Compound No. | Structure | Chemical Name |
|---|---|---|
| 35 | 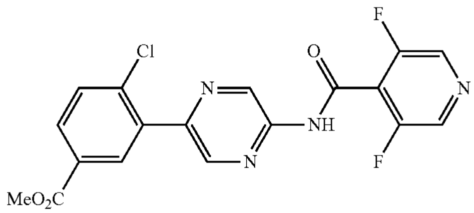 [SMILES: COC(=O)c1ccc(Cl)c(-c2cnc(NC(=O)c3c(F)cncc3F)cn2)c1] | 4-Chloro-3-{5-[(3,5-difluoro-pyridine-4-carbonyl)-amino]-pyrazin-2-yl}-benzoic acid methyl ester |
| 36 | 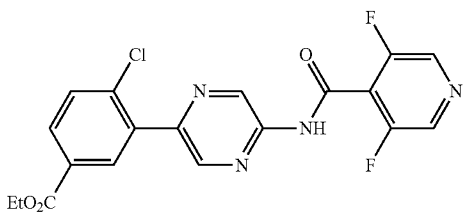 [SMILES: CCOC(=O)c1ccc(Cl)c(-c2cnc(NC(=O)c3c(F)cncc3F)cn2)c1] | 4-Chloro-3-{5-[(3,5-difluoro-pyridine-4-carbonyl)-amino]-pyrazin-2-yl}-benzoic acid ethyl ester |
| 37 | 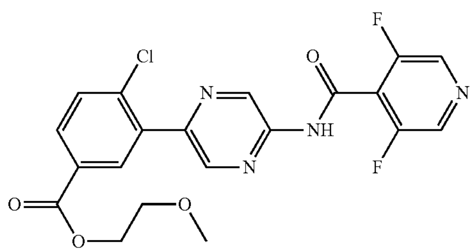 [SMILES: COCCOC(=O)c1ccc(Cl)c(-c2cnc(NC(=O)c3c(F)cncc3F)cn2)c1] | 4-Chloro-3-{5-[(3,5-difluoro-pyridine-4-carbonyl)-amino]-pyrazin-2-yl}-benzoic acid 2-methoxy-ethyl ester |
| 38 | 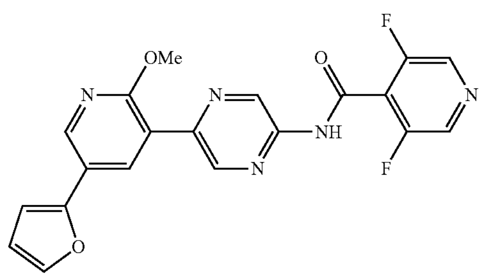 [SMILES: COc1ncc(-c2ccco2)cc1-c1cnc(NC(=O)c2c(F)cncc2F)cn1] | 3,5-Difluoro-N-[5-(5-furan-2-yl-2-methoxy-pyridin-3-yl)-pyrazin-2-yl]-isonicotinamide |
| 39 | 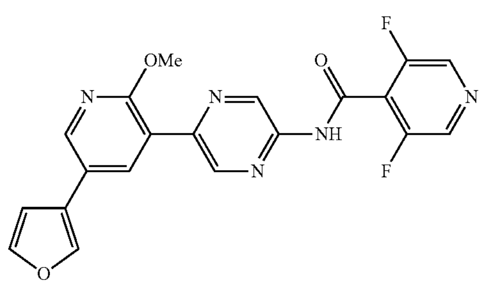 [SMILES: COc1ncc(-c2ccoc2)cc1-c1cnc(NC(=O)c2c(F)cncc2F)cn1] | 3,5-Difluoro-N-[5-(5-furan-3-yl-2-methoxy-pyridin-3-yl)-pyrazin-2-yl]-isonicotinamide |
| 40 | 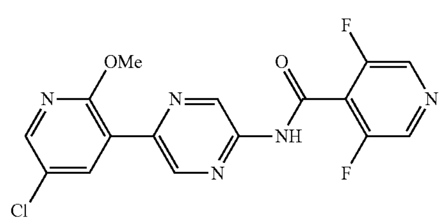 [SMILES: COc1ncc(Cl)cc1-c1cnc(NC(=O)c2c(F)cncc2F)cn1] | N-[5-(5-Chloro-2-methoxy-pyridin-3-yl)-pyrazin-2-yl]-3,5-difluoro-isonicotinamide |

TABLE 1-continued

| Compound No. | Structure | Chemical Name |
|---|---|---|
| 41 | 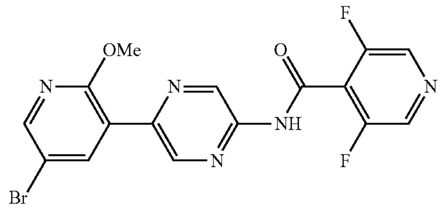 [SMILES: COc1ncc(Br)cc1-c1cnc(NC(=O)c2c(F)cncc2F)cn1] | N-[5-(5-Bromo-2-methoxy-pyridin-3-yl)-pyrazin-2-yl]-3,5-difluoro-isonicotinamide |
| 42 | 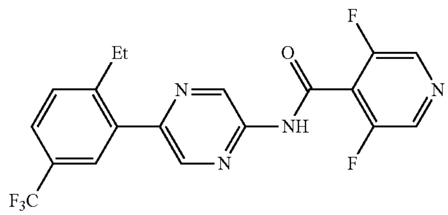 [SMILES: CCc1ccc(C(F)(F)F)cc1-c1cnc(NC(=O)c2c(F)cncc2F)cn1] | N-[5-(2-Ethyl-5-trifluoro-methyl-phenyl)-pyrazin-2-yl]-3,5-difluoro-isonicotinamide |
| 43 | 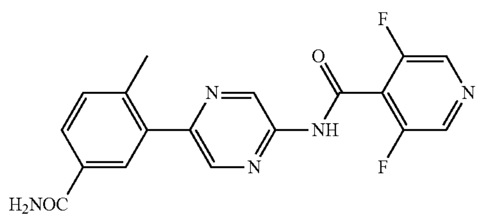 [SMILES: Cc1ccc(C(N)=O)cc1-c1cnc(NC(=O)c2c(F)cncc2F)cn1] | N-[5-(5-Carbamoyl-2-methyl-phenyl)-pyrazin-2-yl]-3,5-difluoro-isonicotinamide |
| 44 | 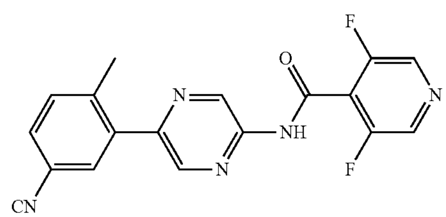 | 3,5-Difluoro-N-[5-(5-isocyano-2-methyl-phenyl)-pyrazin-2-yl]-isonicotinamide |
| 45 | 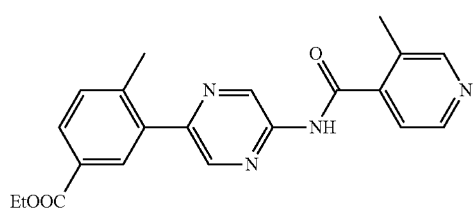 | 4-Methyl-3-{5-[(3-methyl-pyridine-4-carbonyl)-amino]-pyrazin-2-yl}-benzoic acid ethyl ester |
| 46 | 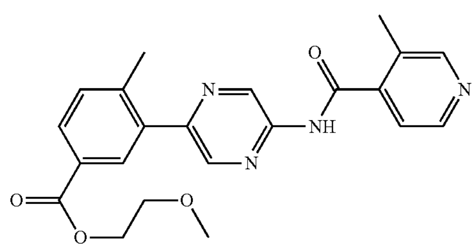 [SMILES: COCCOC(=O)c1ccc(C)c(-c2cnc(NC(=O)c3ccncc3C)cn2)c1] | 4-Methyl-3-{5-[(3-methyl-pyridine-4-carbonyl)-amino]-pyrazin-2-yl}-benzoic acid 2-methoxy-ethyl ester |
| 47 | 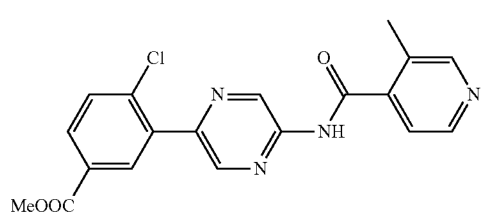 [SMILES: COC(=O)c1ccc(Cl)c(-c2cnc(NC(=O)c3ccncc3C)cn2)c1] | 4-Chloro-3-{5-[(3-methyl-pyridine-4-carbonyl)-amino]-pyrazin-2-yl}-benzoic acid methyl ester |

TABLE 1-continued

| Compound No. | Structure | Chemical Name |
|---|---|---|
| 48 | 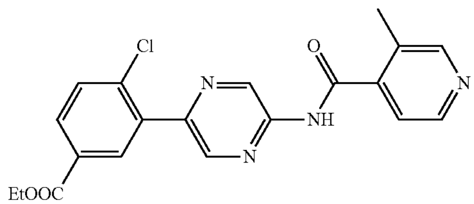 [SMILES: CCOC(=O)c1ccc(Cl)c(-c2cnc(NC(=O)c3ccncc3C)cn2)c1] | 4-Chloro-3-{5-[(3-methyl-pyridine-4-carbonyl)-amino]-pyrazin-2-yl}-benzoic acid ethyl ester |
| 49 | 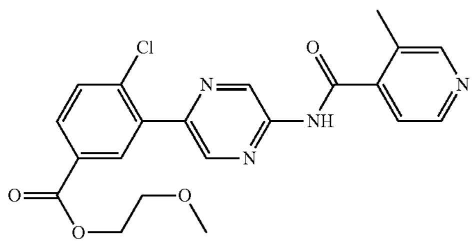 [SMILES: COCCOC(=O)c1ccc(Cl)c(-c2cnc(NC(=O)c3ccncc3C)cn2)c1] | 4-Chloro-3-{5-[(3-methyl-pyridine-4-carbonyl)-amino]-pyrazin-2-yl}-benzoic acid 2-methoxy-ethyl ester |
| 50 | 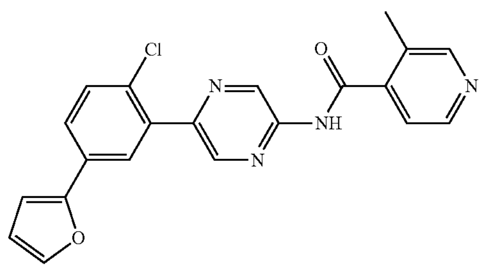 [SMILES: Cc1cnccc1C(=O)Nc1cnc(-c2cc(-c3ccco3)ccc2Cl)cn1] | N-[5-(2-Chloro-5-furan-2-yl-phenyl)-pyrazin-2-yl]-3-methyl-isonicotinamide |
| 51 | 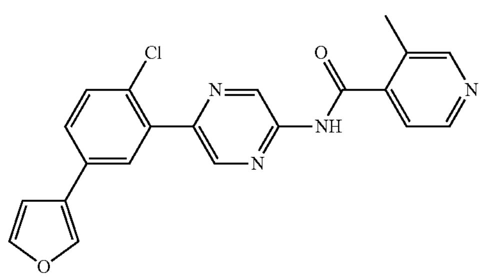 [SMILES: Cc1cnccc1C(=O)Nc1cnc(-c2cc(-c3ccoc3)ccc2Cl)cn1] | N-[5-(2-Chloro-5-furan-3-yl-phenyl)-pyrazin-2-yl]-3-methyl-isonicotinamide |
| 52 | 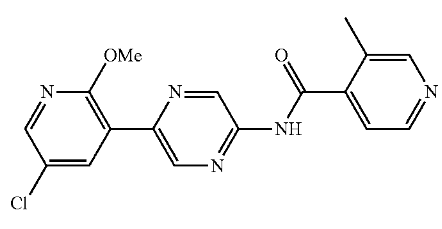 [SMILES: COc1ncc(Cl)cc1-c1cnc(NC(=O)c2ccncc2C)cn1] | N-[5-(5-Chloro-2-methoxy-pyridin-3-yl)-pyrazin-2-yl]-3-methyl-isonicotinamide |
| 53 | 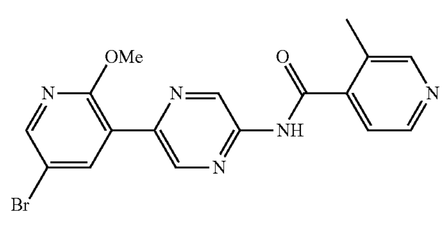 | N-[5-(5-Bromo-2-methoxy-pyridin-3-yl)-pyrazin-2-yl]-3-methyl-isonicotinamide |

TABLE 1-continued

| Compound No. | Structure | Chemical Name |
|---|---|---|
| 54 | 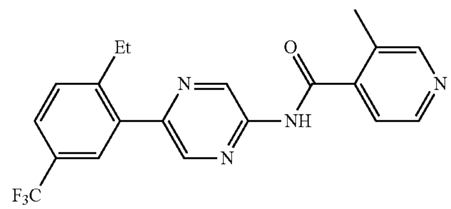 [SMILES: CCc1ccc(C(F)(F)F)cc1-c1cnc(NC(=O)c2ccncc2C)cn1] | N-[5-(2-Ethyl-5-trifluoro-methyl-phenyl)-pyrazin-2-yl]-3-methyl-isonicotinamide |
| 55 | 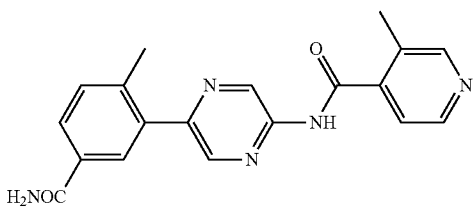 [SMILES: Cc1cnccc1C(=O)Nc1cnc(-c2cc(C(N)=O)ccc2C)cn1] | N-[5-(5-Carbamoyl-2-methyl-phenyl)-pyrazin-2-yl]-3-methyl-isonicotinamide |
| 56 | 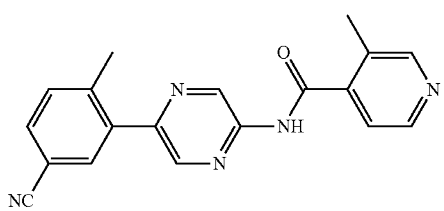 [SMILES: Cc1cnccc1C(=O)Nc1cnc(-c2cc(C#N)ccc2C)cn1] | N-[5-(5-Cyano-2-methyl-phenyl)-pyrazin-2-yl]-3-methyl-isonicotinamide |
| 57 | 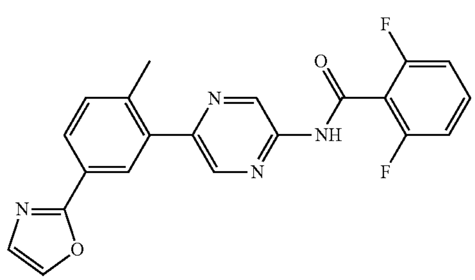 [SMILES: Cc1ccc(-c2ncco2)cc1-c1cnc(NC(=O)c2c(F)cccc2F)cn1] | 2,6-Difluoro-N-[5-(2-methyl-5-oxazol-2-yl-phenyl)-pyrazin-2-yl]-benzamide |
| 58 | 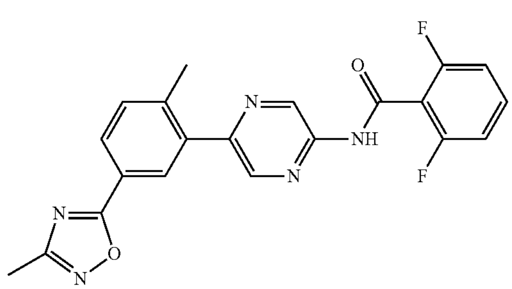 [SMILES: Cc1noc(-c2ccc(C)c(-c3cnc(NC(=O)c4c(F)cccc4F)cn3)c2)n1] | 2,6-Difluoro-N-{5-[2-methyl-5-(3-methyl-[1,2,4]oxadiazol-5-yl)-phenyl]-pyrazin-2-yl}-benzamide |
| 59 | 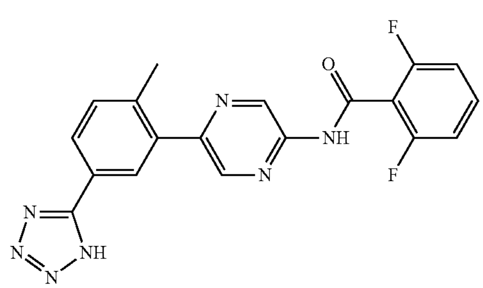 [SMILES: Cc1ccc(-c2nnn[nH]2)cc1-c1cnc(NC(=O)c2c(F)cccc2F)cn1] | 2,6-Difluoro-N-{5-[2-methyl-5-(1H-tetrazol-5-yl)-phenyl]-pyrazin-2-yl}-benzamide |

TABLE 1-continued

| Compound No. | Structure | Chemical Name |
| --- | --- | --- |
| 60 | 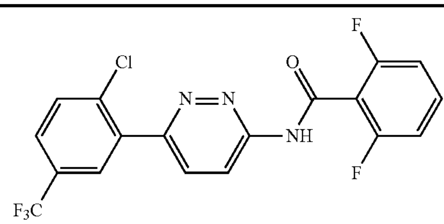 | N-[6-(2-Chloro-5-trifluoro-methyl-phenyl)-pyridazin-3-yl]-2,6-difluoro-benzamide |
| 61 | 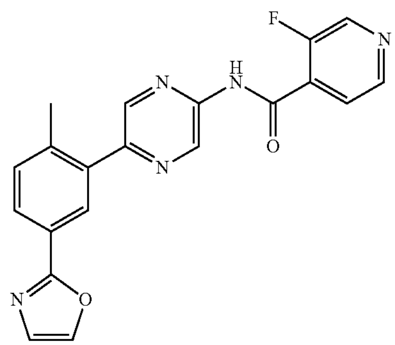 [SMILES: Cc1ccc(-c2ncco2)cc1-c1cnc(NC(=O)c2ccncc2F)cn1] | 3-Fluoro-N-[5-(2-methyl-5-oxazol-2-yl-phenyl)-pyrazin-2-yl]-isonicotinamide |
| 62 | 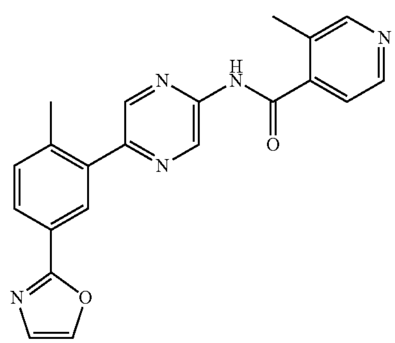 [SMILES: Cc1cnccc1C(=O)Nc1cnc(-c2cc(-c3ncco3)ccc2C)cn1] | 3-Methyl-N-[5-(2-methyl-5-oxazol-2-yl-phenyl)-pyrazin-2-yl]-isonicotinamide |
| 63 | 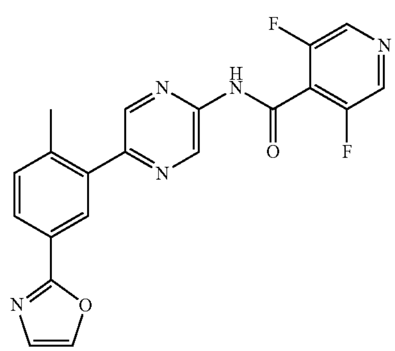 [SMILES: Cc1ccc(-c2ncco2)cc1-c1cnc(NC(=O)c2c(F)cncc2F)cn1] | 3,5-Difluoro-N-[5-(2-methyl-5-oxazol-2-yl-phenyl)-pyrazin-2-yl]-isonicotinamide |
| 64 | 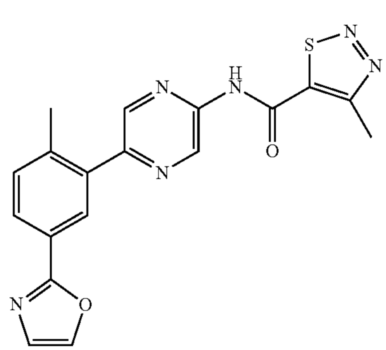 [SMILES: Cc1ccc(-c2ncco2)cc1-c1cnc(NC(=O)c2snnc2C)cn1] | 4-Methyl-[1,2,3]thiadiazole-5-carboxylic acid [5-(2-methyl-5-oxazol-2-yl-phenyl)-pyrazin-2-yl]-amide |

TABLE 1-continued

| Compound No. | Structure | Chemical Name |
|---|---|---|
| 65 | 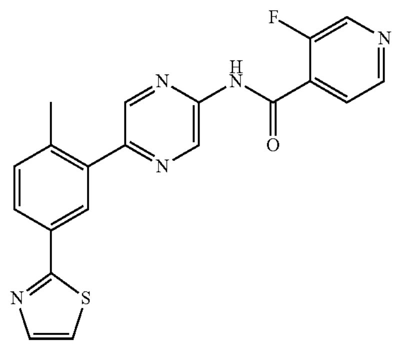 [SMILES: Cc1ccc(-c2nccs2)cc1-c1cnc(NC(=O)c2ccncc2F)cn1] | 3-Fluoro-N-[5-(2-methyl-5-thiazol-2-yl-phenyl)-pyrazin-2-yl]-isonicotinamide |
| 66 | 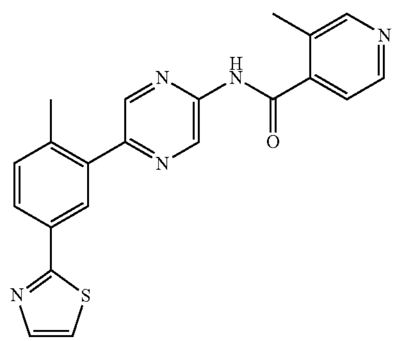 [SMILES: Cc1cnccc1C(=O)Nc1cnc(-c2cc(-c3nccs3)ccc2C)cn1] | 3-Methyl-N-[5-(2-methyl-5-thiazol-2-yl-phenyl)-pyrazin-2-yl]-isonicotinamide |
| 67 | 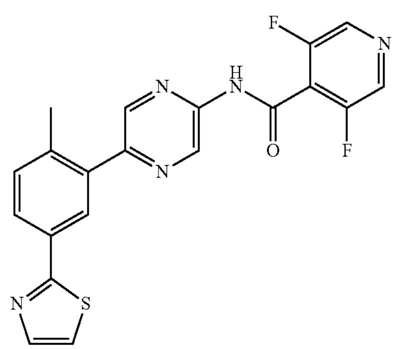 [SMILES: Cc1ccc(-c2nccs2)cc1-c1cnc(NC(=O)c2c(F)cncc2F)cn1] | 3,5-Difluoro-N-[5-(2-methyl-5-thiazol-2-yl-phenyl)-pyrazin-2-yl]-isonicotinamide |
| 68 | 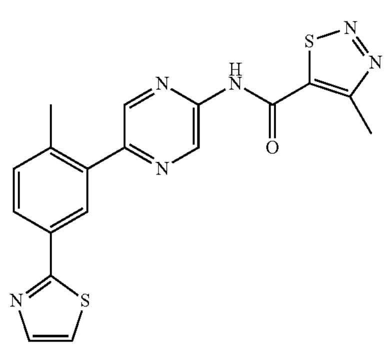 | 4-Methyl-[1,2,3]thiadiazole-5-carboxylic acid [5-(2-methyl-5-thiazol-2-yl-phenyl)-pyrazin-2-yl]-amide |

TABLE 1-continued

| Compound No. | Structure | Chemical Name |
|---|---|---|
| 69 | 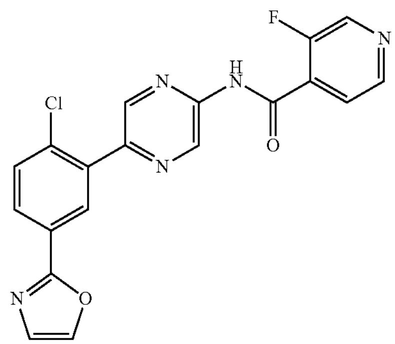 [SMILES: O=C(Nc1cnc(-c2cc(-c3ncco3)ccc2Cl)cn1)c1ccncc1F] | N-[5-(2-Chloro-5-oxazol-2-yl-phenyl)-pyrazin-2-yl]-3-fluoro-isonicotinamide |
| 70 | 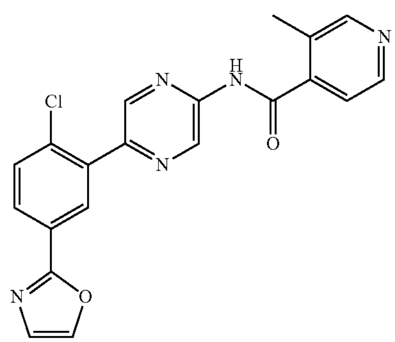 [SMILES: Cc1cnccc1C(=O)Nc1cnc(-c2cc(-c3ncco3)ccc2Cl)cn1] | N-[5-(2-Chloro-5-oxazol-2-yl-phenyl)-pyrazin-2-yl]-3-methyl-isonicotinamide |
| 71 | 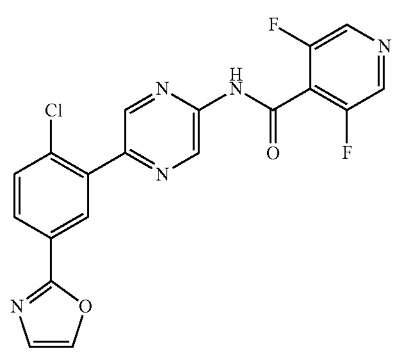 [SMILES: O=C(Nc1cnc(-c2cc(-c3ncco3)ccc2Cl)cn1)c1c(F)cncc1F] | N-[5-(2-Chloro-5-oxazol-2-yl-phenyl)-pyrazin-2-yl]-3,5-difluoro-isonicotinamide |
| 72 | 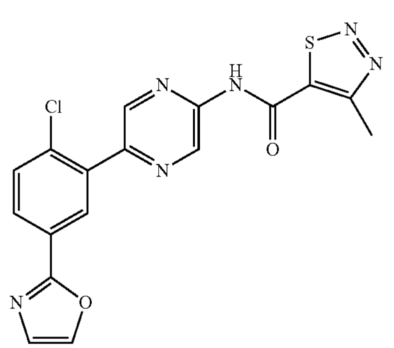 [SMILES: Cc1nnsc1C(=O)Nc1cnc(-c2cc(-c3ncco3)ccc2Cl)cn1] | 4-Methyl-[1,2,3]thiadiazole-5-carboxylic acid [5-(2-chloro-5-oxazol-2-yl-phenyl)-pyrazin-2-yl]-amide |

TABLE 1-continued

| Compound No. | Structure | Chemical Name |
|---|---|---|
| 73 | 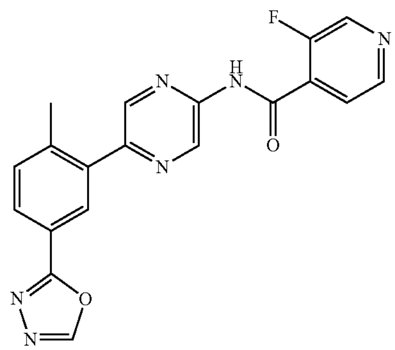 [SMILES: Cc1ccc(-c2nnco2)cc1-c1cnc(NC(=O)c2ccncc2F)cn1] | 3-Fluoro-N-[5-(2-methyl-5-[1,3,4]oxadiazol-2-yl-phenyl)-pyrazin-2-yl]-isonicotinamide |
| 74 | 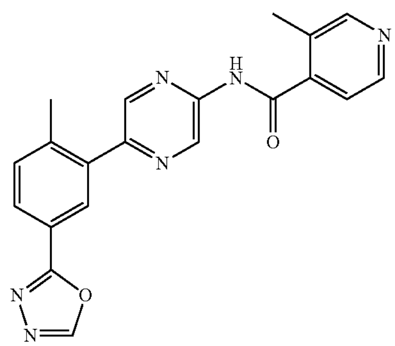 [SMILES: Cc1cnccc1C(=O)Nc1cnc(-c2cc(-c3nnco3)ccc2C)cn1] | 3-Methyl-N-[5-(2-methyl-5-[1,3,4]oxadiazol-2-yl-phenyl)-pyrazin-2-yl]-isonicotinamide |
| 75 | 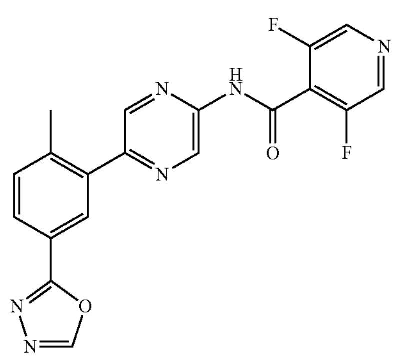 [SMILES: Cc1ccc(-c2nnco2)cc1-c1cnc(NC(=O)c2c(F)cncc2F)cn1] | 3,5-Difluoro-N-[5-(2-methyl-5-[1,3,4]oxadiazol-2-yl-phenyl)-pyrazin-2-yl]-isonicotinamide |
| 76 | 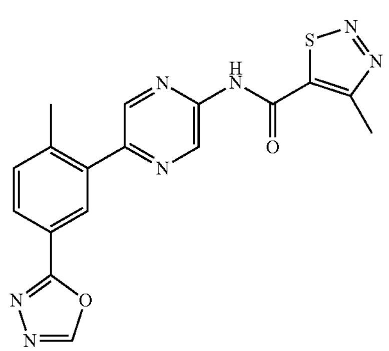 [SMILES: Cc1ccc(-c2nnco2)cc1-c1cnc(NC(=O)c2snnc2C)cn1] | 4-Methyl-[1,2,3]thiadiazole-5-carboxylic acid [5-(2-methyl-5-[1,3,4]oxadiazol-2-yl-phenyl)-pyrazin-2-yl]-amide |

TABLE 1-continued
| Compound No. | Structure | Chemical Name |
|---|---|---|
| 77 | 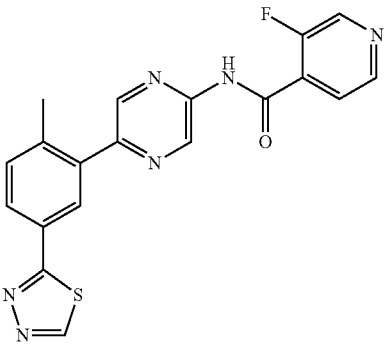 | 3-Fluoro-N-[5-(2-methyl-5-[1,3,4]thiadiazol-2-yl-phenyl)-pyrazin-2-yl]-isonicotinamide |
| 78 | 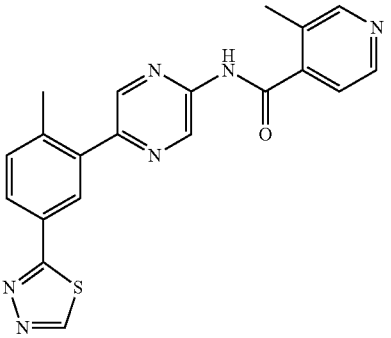 | 3-Methyl-N-[5-(2-methyl-5-[1,3,4]thiadiazol-2-yl-phenyl)-pyrazin-2-yl]-isonicotinamide |
| 79 | 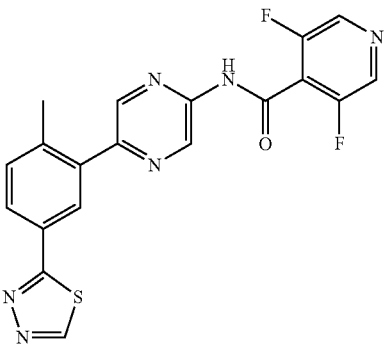 [SMILES: Cc1ccc(-c2nncs2)cc1-c1cnc(NC(=O)c2c(F)cncc2F)cn1] | 3,5-Difluoro-N-[5-(2-methyl-5-[1,3,4]thiadiazol-2-yl-phenyl)-pyrazin-2-yl]-isonicotinamide |
| 80 | 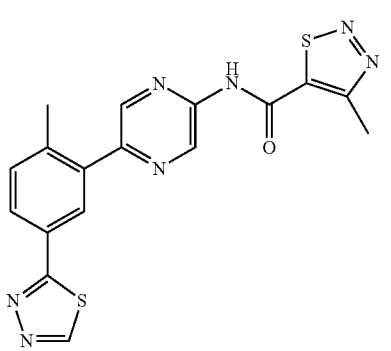 [SMILES: Cc1ccc(-c2nncs2)cc1-c1cnc(NC(=O)c2snnc2C)cn1] | 4-Methyl-[1,2,3]thiadiazole-5-carboxylic acid [5-(2-methyl-5-[1,3,4]thiadiazol-2-yl-phenyl)-pyrazin-2-yl]-amide |

TABLE 1-continued

| Compound No. | Structure | Chemical Name |
| --- | --- | --- |
| 81 | 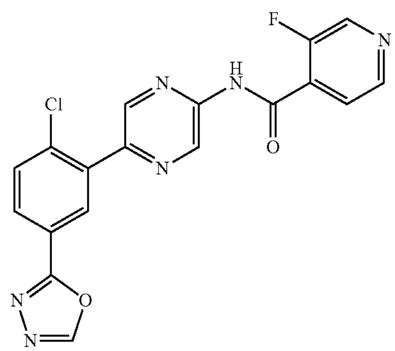 [SMILES: O=C(Nc1cnc(-c2cc(-c3nnco3)ccc2Cl)cn1)c1ccncc1F] | N-[5-(2-Chloro-5-[1,3,4]oxadiazol-2-yl-phenyl)-pyrazin-2-yl]-3-fluoro-isonicotinamide |
| 82 | 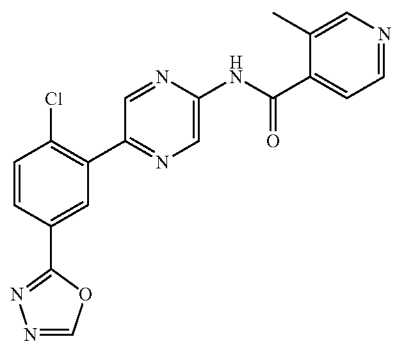 [SMILES: Cc1cnccc1C(=O)Nc1cnc(-c2cc(-c3nnco3)ccc2Cl)cn1] | N-[5-(2-Chloro-5-[1,3,4]oxadiazol-2-yl-phenyl)-pyrazin-2-yl]-3-methyl-isonicotinamide |
| 83 | 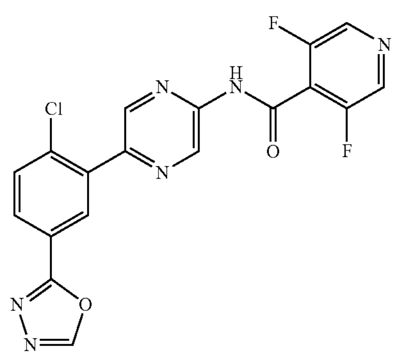 [SMILES: O=C(Nc1cnc(-c2cc(-c3nnco3)ccc2Cl)cn1)c1c(F)cncc1F] | N-[5-(2-Chloro-5-[1,3,4]oxadiazol-2-yl-phenyl)-pyrazin-2-yl]-3,5-difluoro-isonicotinamide |
| 84 | 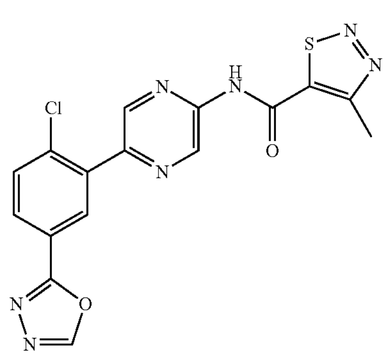 [SMILES: Cc1nnsc1C(=O)Nc1cnc(-c2cc(-c3nnco3)ccc2Cl)cn1] | 4-Methyl-[1,2,3]thiadiazole-5-carboxylic acid [5-(2-chloro-5-[1,3,4]oxadiazol-2-yl-phenyl)-pyrazin-2-yl]-amide |

TABLE 1-continued

| Compound No. | Structure | Chemical Name |
|---|---|---|
| 85 | 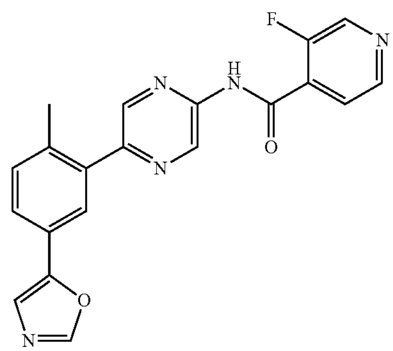 [SMILES: Cc1ccc(-c2cnco2)cc1-c1cnc(NC(=O)c2ccncc2F)cn1] | 3-Fluoro-N-[5-(2-methyl-5-oxazol-5-yl-phenyl)-pyrazin-2-yl]-isonicotinamide |
| 86 | 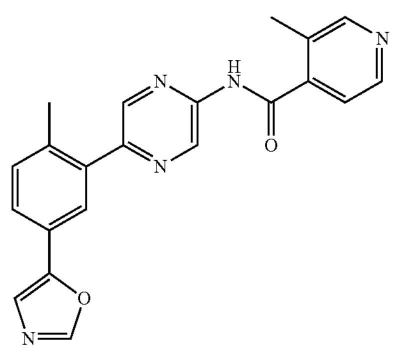 [SMILES: Cc1cnccc1C(=O)Nc1cnc(-c2cc(-c3cnco3)ccc2C)cn1] | 3-Methyl-N-[5-(2-methyl-5-oxazol-5-yl-phenyl)-pyrazin-2-yl]-isonicotinamide |
| 87 | 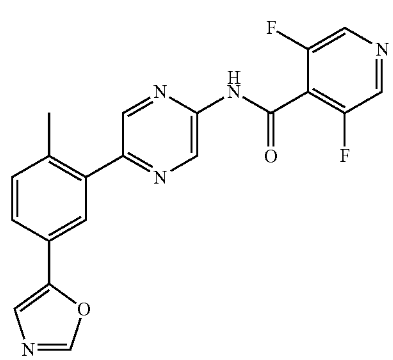 [SMILES: Cc1ccc(-c2cnco2)cc1-c1cnc(NC(=O)c2c(F)cncc2F)cn1] | 3,5-Difluoro-N-[5-(2-methyl-5-oxazol-5-yl-phenyl)-pyrazin-2-yl]-isonicotinamide |
| 88 | 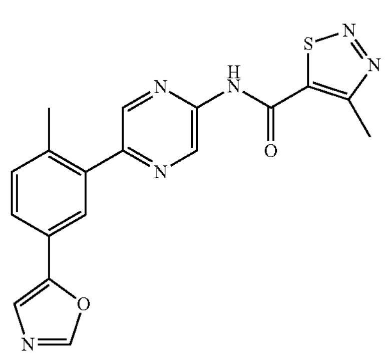 [SMILES: Cc1ccc(-c2cnco2)cc1-c1cnc(NC(=O)c2snnc2C)cn1] | 4-Methyl-[1,2,3]thiadiazole-5-carboxylic acid [5-(2-methyl-5-oxazol-5-yl-phenyl)-pyrazin-2-yl]-amide |

TABLE 1-continued

| Compound No. | Structure | Chemical Name |
|---|---|---|
| 89 | 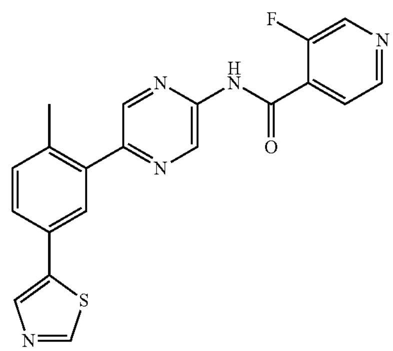 [SMILES: Cc1ccc(-c2cncs2)cc1-c1cnc(NC(=O)c2ccncc2F)cn1] | 3-Fluoro-N-[5-(2-methyl-5-thiazol-5-yl-phenyl)-pyrazin-2-yl]-isonicotinamide |
| 90 | 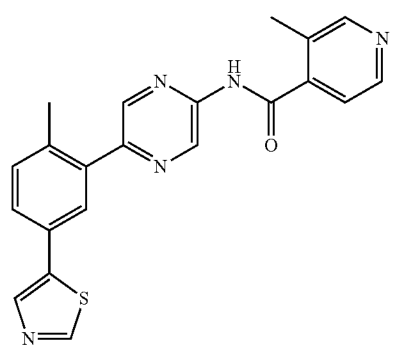 [SMILES: Cc1cnccc1C(=O)Nc1cnc(-c2cc(-c3cncs3)ccc2C)cn1] | 3-Methyl-N-[5-(2-methyl-5-thiazol-5-yl-phenyl)-pyrazin-2-yl]-isonicotinamide |
| 91 | 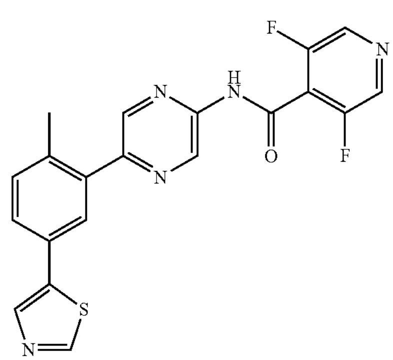 [SMILES: Cc1ccc(-c2cncs2)cc1-c1cnc(NC(=O)c2c(F)cncc2F)cn1] | 3,5-Difluoro-N-[5-(2-methyl-5-thiazol-5-yl-phenyl)-pyrazin-2-yl]-isonicotinamide |
| 92 | 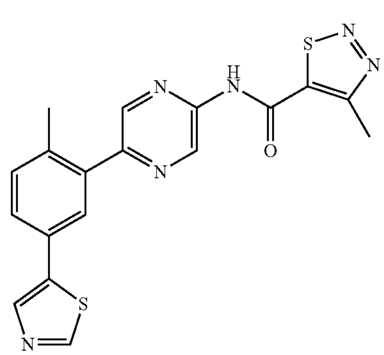 [SMILES: Cc1ccc(-c2cncs2)cc1-c1cnc(NC(=O)c2snnc2C)cn1] | 4-Methyl-[1,2,3]thiadiazole-5-carboxylic acid [5-(2-methyl-5-thiazol-5-yl-phenyl)-pyrazin-2-yl]-amide |

TABLE 1-continued

| Compound No. | Structure | Chemical Name |
|---|---|---|
| 93 | 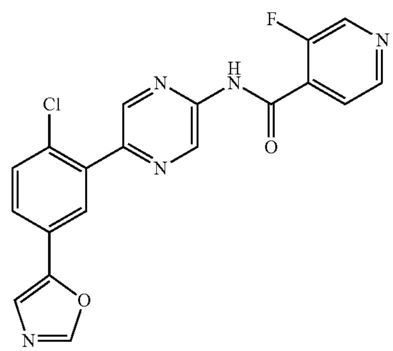 [SMILES: O=C(Nc1cnc(-c2cc(-c3cnco3)ccc2Cl)cn1)c1ccncc1F] | N-[5-(2-Chloro-5-oxazol-5-yl-phenyl)-pyrazin-2-yl]-3-fluoro-isonicotinamide |
| 94 | 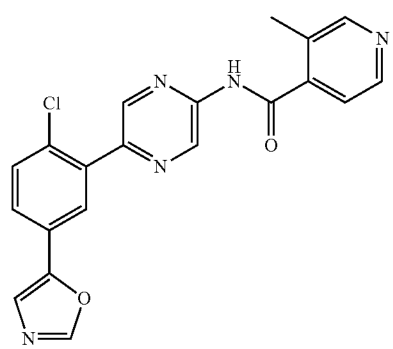 [SMILES: Cc1cnccc1C(=O)Nc1cnc(-c2cc(-c3cnco3)ccc2Cl)cn1] | N-[5-(2-Chloro-5-oxazol-5-yl-phenyl)-pyrazin-2-yl]-3-methyl-isonicotinamide |
| 95 | 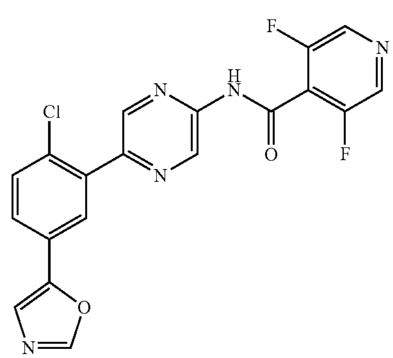 [SMILES: O=C(Nc1cnc(-c2cc(-c3cnco3)ccc2Cl)cn1)c1c(F)cncc1F] | N-[5-(2-Chloro-5-oxazol-5-yl-phenyl)-pyrazin-2-yl]-3,5-difluoro-isonicotinamide |
| 96 | 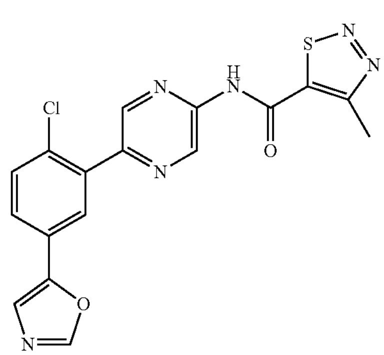 [SMILES: Cc1nnsc1C(=O)Nc1cnc(-c2cc(-c3cnco3)ccc2Cl)cn1] | 4-Methyl-[1,2,3]thiadiazole-5-carboxylic acid [5-(2-chloro-5-oxazol-5-yl-phenyl)-pyrazin-2-yl]-amide |

TABLE 1-continued

| Compound No. | Structure | Chemical Name |
|---|---|---|
| 97 | 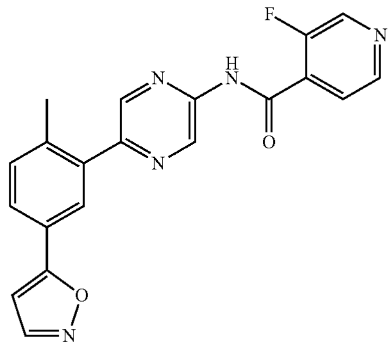 [SMILES: Cc1ccc(-c2ccno2)cc1-c1cnc(NC(=O)c2ccncc2F)cn1] | 3-Fluoro-N-[5-(5-isoxazol-5-yl-2-methyl-phenyl)-pyrazin-2-yl]-isonicotinamide |
| 98 | 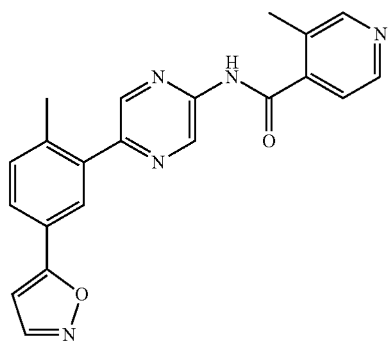 [SMILES: Cc1cnccc1C(=O)Nc1cnc(-c2cc(-c3ccno3)ccc2C)cn1] | N-[5-(5-Isoxazol-5-yl-2-methyl-phenyl)-pyrazin-2-yl]-3-methyl-isonicotinamide |
| 99 | 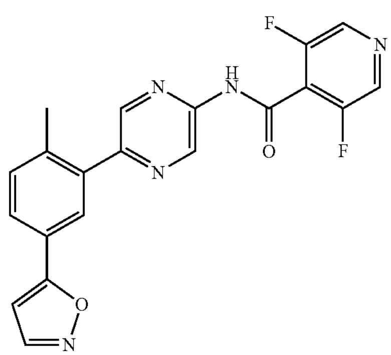 [SMILES: Cc1ccc(-c2ccno2)cc1-c1cnc(NC(=O)c2c(F)cncc2F)cn1] | 3,5-Difluoro-N-[5-(5-isoxazol-5-yl-2-methyl-phenyl)-pyrazin-2-yl]-isonicotinamide |
| 100 | 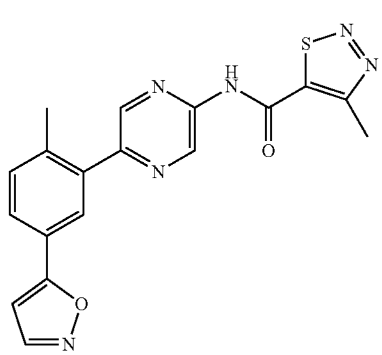 [SMILES: Cc1ccc(-c2ccno2)cc1-c1cnc(NC(=O)c2snnc2C)cn1] | 4-Methyl-[1,2,3]thiadiazole-5-carboxylic acid [5-(5-isoxazol-5-yl-2-methyl-phenyl)-pyrazin-2-yl]-amide |

TABLE 1-continued

| Compound No. | Structure | Chemical Name |
|---|---|---|
| 101 | 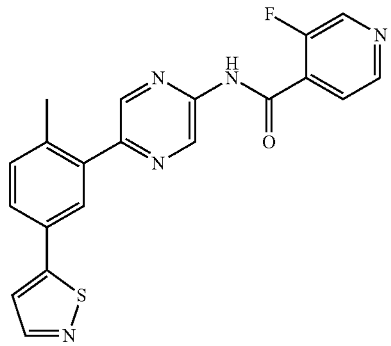 [SMILES: Cc1ccc(-c2ccns2)cc1-c1cnc(NC(=O)c2ccncc2F)cn1] | 3-Fluoro-N-[5-(5-isothiazol-5-yl-2-methyl-phenyl)-pyrazin-2-yl]-isonicotinamide |
| 102 | 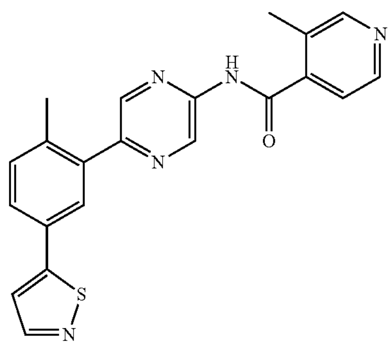 [SMILES: Cc1cnccc1C(=O)Nc1cnc(-c2cc(-c3ccns3)ccc2C)cn1] | N-[5-(5-Isothiazol-5-yl-2-methyl-phenyl)-pyrazin-2-yl]-3-methyl-isonicotinamide |
| 103 | 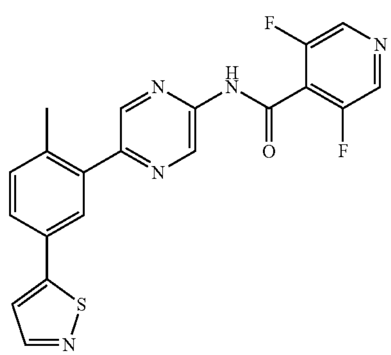 [SMILES: Cc1ccc(-c2ccns2)cc1-c1cnc(NC(=O)c2c(F)cncc2F)cn1] | 3,5-Difluoro-N-[5-(5-isothiazol-5-yl-2-methyl-phenyl)-pyrazin-2-yl]-isonicotinamide |
| 104 | 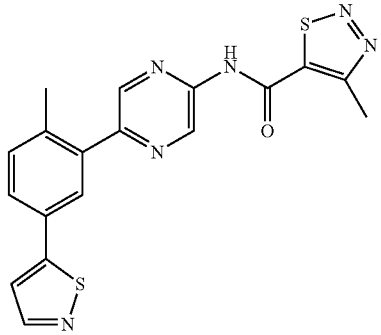 [SMILES: Cc1ccc(-c2ccns2)cc1-c1cnc(NC(=O)c2snnc2C)cn1] | 4-Methyl-[1,2,3]thiadiazole-5-carboxylic acid [5-(5-isothiazol-5-yl-2-methyl-phenyl)-pyrazin-2-yl]-amide |

TABLE 1-continued

| Compound No. | Structure | Chemical Name |
|---|---|---|
| 105 | 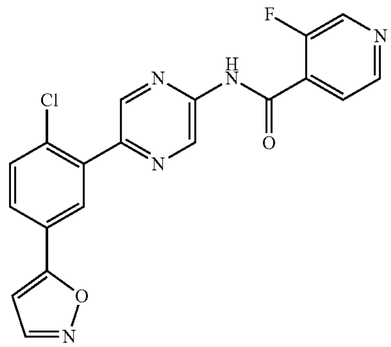 [SMILES: O=C(Nc1cnc(-c2cc(-c3ccno3)ccc2Cl)cn1)c1ccncc1F] | N-[5-(2-Chloro-5-isoxazol-5-yl-phenyl)-pyrazin-2-yl]-3-fluoro-isonicotinamide |
| 106 | 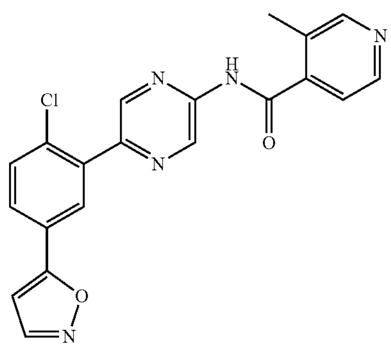 [SMILES: Cc1cnccc1C(=O)Nc1cnc(-c2cc(-c3ccno3)ccc2Cl)cn1] | N-[5-(2-Chloro-5-isoxazol-5-yl-phenyl)-pyrazin-2-yl]-3-methyl-isonicotinamide |
| 107 | 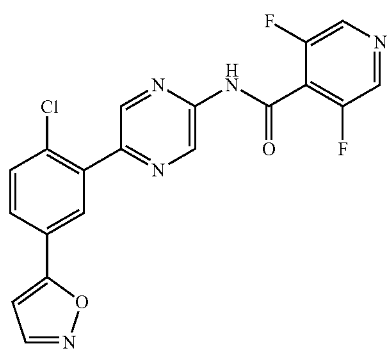 [SMILES: O=C(Nc1cnc(-c2cc(-c3ccno3)ccc2Cl)cn1)c1c(F)cncc1F] | N-[5-(2-Chloro-5-isoxazol-5-yl-phenyl)-pyrazin-2-yl]-3,5-difluoro-isonicotinamide |
| 108 | 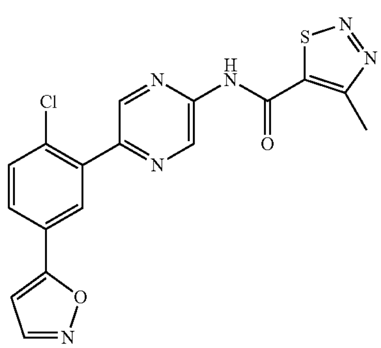 [SMILES: Cc1nnsc1C(=O)Nc1cnc(-c2cc(-c3ccno3)ccc2Cl)cn1] | 4-Methyl-[1,2,3]thiadiazole-5-carboxylic acid [5-(2-chloro-5-isoxazol-5-yl-phenyl)-pyrazin-2-yl]-amide |
| 109 | 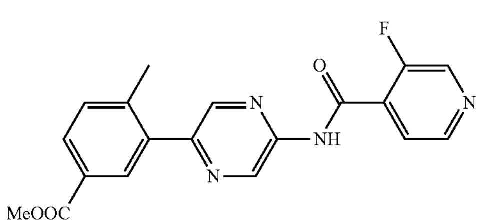 [SMILES: COC(=O)c1ccc(C)c(-c2cnc(NC(=O)c3ccncc3F)cn2)c1] | 3-{5-[(3-Fluoro-pyridine-4-carbonyl)-amino]-pyrazin-2-yl}-4-methyl-benzoic acid methyl ester |

TABLE 1-continued

| Compound No. | Chemical Name |
|---|---|
| 110 | N-[5-(2,5-Dimethoxy-phenyl)-pyrazin-2-yl]-2,6-difluoro-benzamide |
| 111 | N-[5-(2-Chloro-5-trifluoromethyl-phenyl)-pyrazin-2-yl]-2-methyl-nicotinamide |
| 112 | Cyclohexanecarboxylic acid [5-(2-chloro-5-trifluoromethyl-phenyl)-pyrazin-2-yl]-amide |
| 113 | N-[5-(2,5-Dimethoxy-phenyl)-pyrazin-2-yl]-3-fluoro-isonicotinamide |
| 114 | 4-Methyl-[1,2,3]thiadiazole-5-carboxylic acid [5-(2-chloro-5-trifluoromethyl-phenyl)-pyrazin-2-yl]-amide |
| 115 | N-[5-(2-Chloro-5-trifluoromethyl-phenyl)-pyrazin-2-yl]-3,5-difluoro-isonicotinamide |
| 116 | N-[5-(2-Chloro-5-trifluoromethyl-phenyl)-pyrimidin-2-yl]-2,6-difluoro-benzamide |

TABLE 1-continued

| Compound No. | Structure | Chemical Name |
|---|---|---|
| 117 | 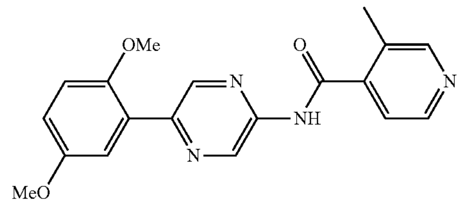 [SMILES: COc1ccc(OC)c(-c2cnc(NC(=O)c3ccncc3C)cn2)c1] | N-[5-(2,5-Dimethoxy-phenyl)-pyrazin-2-yl]-3-methyl-isonicotinamide |
| 118 | 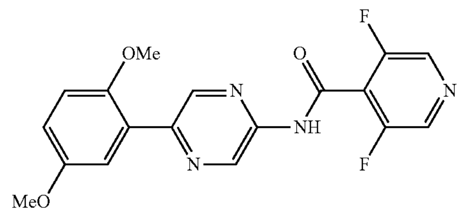 [SMILES: COc1ccc(OC)c(-c2cnc(NC(=O)c3c(F)cncc3F)cn2)c1] | N-[5-(2,5-Dimethoxy-phenyl)-pyrazin-2-yl]-3,5-difluoro-isonicotinamide |
| 119 | 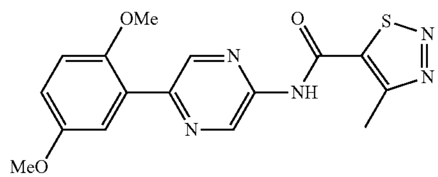 [SMILES: COc1ccc(OC)c(-c2cnc(NC(=O)c3snnc3C)cn2)c1] | 4-Methyl-[1,2,3]thiadiazole-5-carboxylic acid [5-(2,5-dimethoxy-phenyl)-pyrazin-2-yl]-amide |
| 120 | 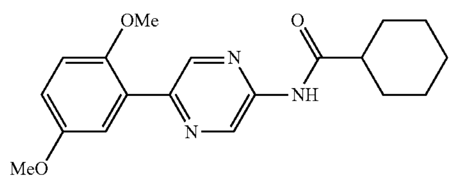 [SMILES: COc1ccc(OC)c(-c2cnc(NC(=O)C3CCCCC3)cn2)c1] | Cyclohexanecarboxylic acid [5-(2,5-dimethoxy-phenyl)-pyrazin-2-yl]-amide |
| 121 | 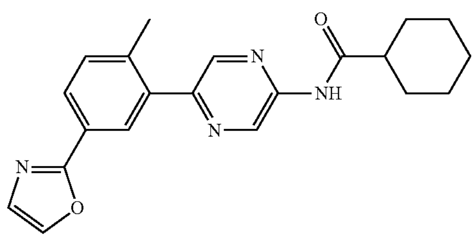 [SMILES: Cc1ccc(-c2ncco2)cc1-c1cnc(NC(=O)C2CCCCC2)cn1] | Cyclohexanecarboxylic acid [5-(2-methyl-5-oxazol-2-yl-phenyl)-pyrazin-2-yl]-amide |
| 122 | 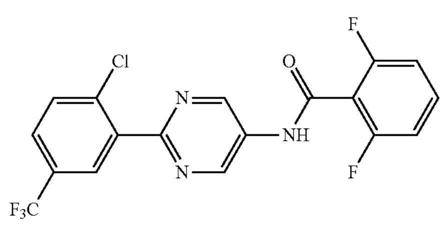 [SMILES: O=C(Nc1cnc(-c2cc(C(F)(F)F)ccc2Cl)nc1)c1c(F)cccc1F] | N-[2-(2-Chloro-5-trifluoromethyl-phenyl)-pyrimidin-5-yl]-2,6-difluoro-benzamide |

Mechanism of Action

Activation of T-lymphocytes in response to an antigen is dependent on calcium ion oscillations. Calcium ion oscillations in T-lymphocytes are triggered through stimulation of the T-cell antigen receptor, and involve calcium ion influx through the stored-operated $Ca^{2+}$-release-activated $Ca^{2+}$ (CRAC) channel. In addition, antigen induced degranulation of mast cells has also been shown to be initiated by calcium ion in flux. Although the molecular structure of the CRAC ion channel has not been identified, a detailed electrophysiological profile of the channel exist. Thus, inhibition of CRAC ion channels can be measured by measuring inhibition of the $I_{CRAC}$ current. Calcium ion oscillations in T-cells have been implicated in the activation of several transcription factors (e.g., NFAT, Oct/Oap and NFκB) which are critical for T-cell activation (Lewis, *Biochemical Society Transactions* (2003), 31:925-929, the entire teachings of which are incorporated herein by reference). Without wishing to be bound by any theory, it is believed that because the compounds of the invention inhibit the activity of CRAC ion channels, they inhibit immune cell activation.

Methods of Treatment and Prevention

In accordance with the invention, an effective amount of a compound of any one of formulas (I) through (XIV) or Table 1, or a pharmaceutically acceptable salt, solvate, clathrate, and prodrug thereof, or a pharmaceutical composition comprising a compound of any one of formulas (I) through (XIV) or Table 1, or a pharmaceutically acceptable salt, solvate, clathrate, and prodrug thereof, is administered to a patient in need of immunosuppression or in need of treatment or prevention of an inflammatory condition, an immune disorder, or an allergic disorder. Such patients may be treatment naïve or may experience partial or no response to conventional therapies.

Responsiveness to immunosuppression or of a particular inflammatory condition, immune disorder, or allergic disorder in a subject can be measured directly (e.g., measuring blood levels of inflammatory cytokines (such as IL-2, IL-4, IL-5, IL-13, GM-CSF, TNF-α, IFN-γ and the like) after administration of a compound of this invention), or can be inferred based on an understanding of disease etiology and progression. The compounds of any one of formulas (I) through (XIV), or Table 1, or pharmaceutically acceptable salts, solvates, clathrates, and prodrugs thereof can be assayed in vitro or in vivo, for the desired therapeutic or prophylactic activity, prior to use in humans. For example, known animal models of inflammatory conditions, immune disorders, or allergic disorders can be used to demonstrate the safety and efficacy of compounds of this invention.

Preparation of Compounds of the Invention

In general, the pyrazine compounds of the invention that have amide linkers are prepared by contacting a 2-halo-5-amino-pyrazine (XV) with an acid chloride (XVI) in the presence of a base to form intermediate compound (XVII) having an amide linkage (see Scheme I).

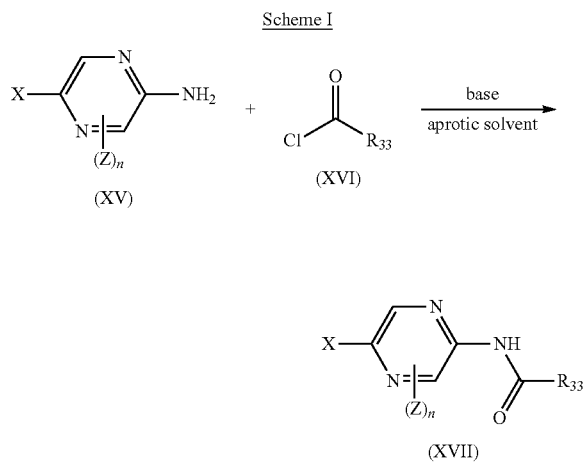

X is a halo.
$R_{33}$ is $R_2$, $R_{13}$ or $R_{21}$.

Intermediate (XVII) is then reacted with a boric acid derivative (XVIII) in the presence of Pd(PPh$_3$)$_4$ and a base to form pyrazine compounds of the invention having amide linkers (XIX) (see Scheme II).

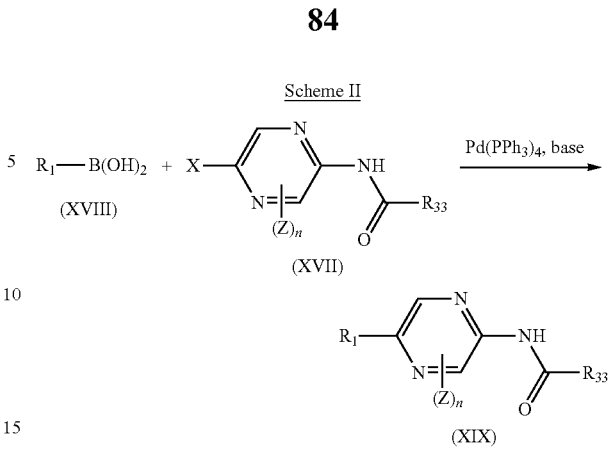

Pyrazine compounds having an amide linker in which the amine group is attached to $R_{33}$ and the carbonyl group is attached to the pyrazine ring can be prepared by reacting 2-halo-pyrazine-5-carbonyl chloride (XX) with an amine (XXI) in the presence of a base to form intermediate compound (XXII) (see Scheme III).

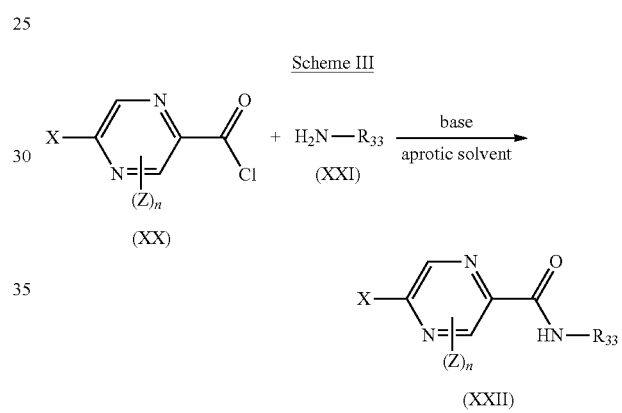

Intermediate (XXII) is then reacted with a boric acid derivative (XVIII) in the presence of Pd(PPh$_3$)$_4$ and a base (as in Scheme II) to form pyrazine compounds of the invention.

Compounds of the invention in which L is —NHC(S)— or —C(S)NH— can be prepared by treating compounds having an amide linker with Lawesson's reagent.

Compounds having —CH$_2$—NH— or —NH—CH$_2$— linkers can be prepared by contacting compounds having —NHC(S)— or —C(S)NH— linkers with Raney Ni. Alternatively, compounds of the invention having a —CH$_2$—NH— or —NH—CH$_2$— linker can be prepared by reducing a compound having a —C(O)—NH— or —NH—C(O)— linker, respectively, with, for example, sodium borohydride (see U.S. patent application Ser. No. 10/897,681, filed on Jul. 22, 2004, the entire teachings of which are incorporated herein by reference).

Compounds of the invention having —C(O)— linkers can be prepared by a Friedel-Craft acylation reaction by reacting a pyrazine derivative (XXIII) with an acid chloride (XXIV) in the presence of AlCl$_3$ to form an intermediate (XXV) which can then be reacted with an [1,3,2]dioxaborolan-2-yl-aryl or -heteroaryl (XXVI) in the presence of a palladium catalyst and a base to form a compound of the invention having a carbonyl linker (XXVII) (see Scheme IV).

Scheme IV

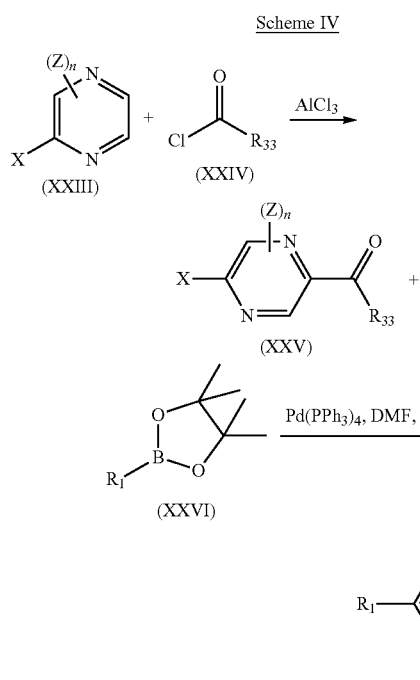

Compounds of the invention that have —C(S)— can be prepared from compounds that have carbonyl linkers by treating them with Lawesson's reagent or $P_2S_5$ in pyridine.

Pyridazine compounds of the invention can be prepared in analogous fashion to that described for pyrazine compounds in Schemes I, II, III and IV.

Pyrimidine compounds of the invention can be prepared by coupling a boric acid derivative (XVIII) with a 2-amino-5-halo-pyrimidine (XXVIII) in the presence of a Pd(PhCN)$_2$Cl$_2$, 1,4-bis(diphenylphosphino)butane (dppb) and a base to an amino-pyrimidine intermediate (XXIX). The amino-pyrimidine intermediate (XXIX) is then reacted with an acid chloride in pyridine to form a pyrimidine compound of the invention (see Scheme V).

Scheme V

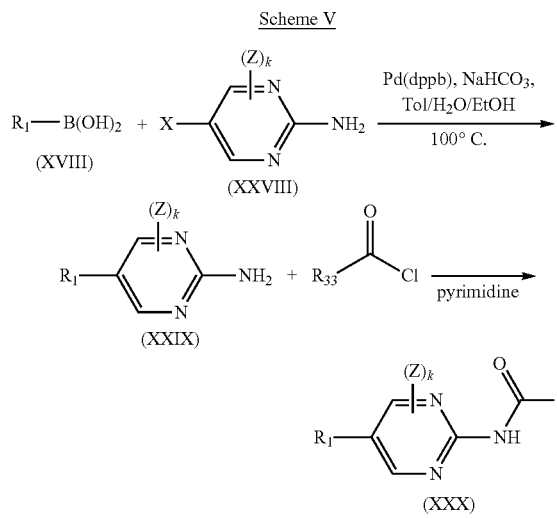

k is 0, 1 or 2

Alternatively, pyrimidine compounds of the invention can be prepared by coupling a boric acid derivative (XVIII) with a 5-nitro-2-halo-pyrimidine (XXXI) in the presence of Pd(PPh$_2$)$_4$ and a base to form a nitro-pyrimidine intermediate (XXXII). The nitro group of the nitro-pyrimidine intermediate (XXXII) can be reduced by treating it with SnCl$_2$ to form an amino-pyrimidine intermediate (XXXIII). The amino-pyrimidine intermediate (XXXIII) can then be coupled to a carboxylic acid derivative in the presence of 1-(3-dimethylaminopropyl)-3-ethylcarbodiimide (EDC) to form a pyrimidine compound of the invention (XXXV) (see Scheme VI).

Scheme VI

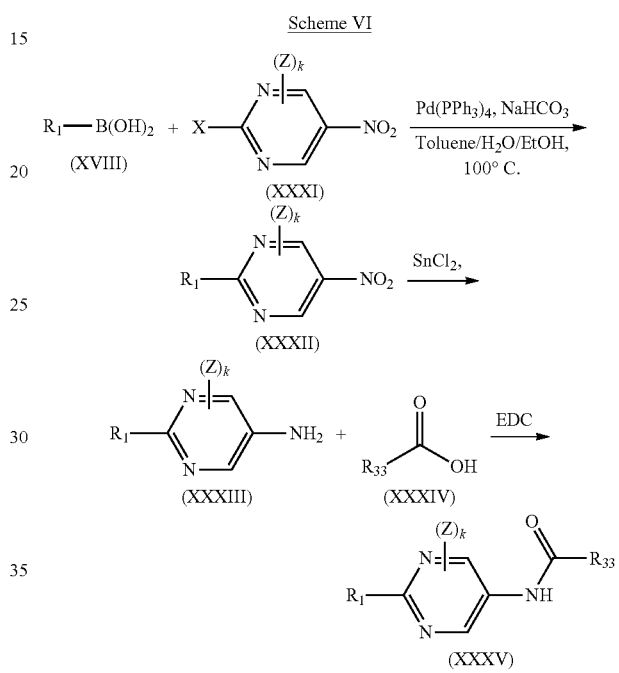

Pharmaceutical Compositions and Dosage Forms

Pharmaceutical compositions and dosage forms of the invention comprise one or more active ingredients in relative amounts and formulated in such a way that a given pharmaceutical composition or dosage form can be used for immunosuppression or to treat or prevent inflammatory conditions, immune disorders, and allergic disorders. Preferred pharmaceutical compositions and dosage forms comprise a compound of any one of formulas (I) through (XIV), or Table 1, or a pharmaceutically acceptable prodrug, salt, solvate, or clathrate thereof, optionally in combination with one or more additional active agents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of any one of formulas (I) through (XIV), or Table 1, or a pharmaceutically acceptable salt, solvate, clathrate, or prodrug thereof in an amount of from about 1 mg to about 1000 mg, preferably in an amount of from about 50 mg to about 500 mg, and most preferably in an amount of from about 75 mg to about 350 mg. The typical total daily dosage of a compound of any one of formulas (I) through (XIV), or Table 1, or a pharmaceutically acceptable salt, solvate, clathrate, or prodrug thereof can range from about 1 mg to about 5000 mg per day, preferably in an amount from about 50 mg to about 1500 mg per day, more preferably from about 75 mg to about 1000 mg per day. It is within the skill of the art to determine the appropriate dose and dosage form for a given patient.

Oral Dosage Forms

Pharmaceutical compositions of the invention that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formula (I) through (XIV), or Table 1, or a pharmaceutically acceptable salt, solvate, hydrate, clathrate, or prodrug thereof, in spheroids which further comprise microcrystalline cellulose and, optionally, hydroxypropylmethyl-cellulose coated with a mixture of ethyl cellulose and hydroxypropylmethylcellulose. Such extended release formulations can be prepared according to U.S. Pat. No. 6,274,171, the entire teachings of which are incorporated herein by reference.

A specific controlled-release formulation of this invention comprises from about 6% to about 40% a compound of any one of formulas (I) through (XIV), or Table 1 by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Combination Therapy

The methods for immunosuppression or for treating or preventing inflammatory conditions, allergic disorders, and immune disorders in a patient in need thereof can further comprise administering to the patient being administered a compound of this invention, an effective amount of one or more other active agents. Such active agents may include those used conventionally for immunosuppression or for inflammatory conditions, allergic disorders, or immune disorders. These other active agents may also be those that provide other benefits when administered in combination with the compounds of this invention. For example, other therapeutic agents may include, without limitation, steroids, non-steroidal anti-inflammatory agents, antihistamines, analgesics, immunosuppressive agents and suitable mixtures thereof. In such combination therapy treatment, both the compounds of this invention and the other drug agent(s) are administered to a subject (e.g., humans, male or female) by conventional methods. The agents may be administered in a single dosage form or in separate dosage forms. Effective amounts of the other therapeutic agents and dosage forms are well known to those skilled in the art. It is well within the skilled artisan's purview to determine the other therapeutic agent's optimal effective-amount range.

In one embodiment of the invention where another therapeutic agent is administered to a subject, the effective amount of the compound of this invention is less than its effective amount when the other therapeutic agent is not administered. In another embodiment, the effective amount of the conventional agent is less than its effective amount when the compound of this invention is not administered. In this way, undesired side effects associated with high doses of either agent may be minimized. Other potential advantages (including without limitation improved dosing regimens and/or reduced drug cost) will be apparent to those of skill in the art.

In one embodiment relating to autoimmune, allergic and inflammatory conditions, the other therapeutic agent may be a steroid or a non-steroidal anti-inflammatory agent. Particularly useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in *Goodman & Gilman's The Pharmacological Basis of Therapeutics* 617-57 (Perry B. Molinhoff and Raymond W. Ruddon eds., $9^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Of particular relevance to allergic disorders, the other therapeutic agent may be an anthihistamine. Useful antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For a more detailed description of antihihistamines, see Goodman & Gilman's The Pharmacological Basis of Therapeutics (2001) 651-57, $10^{th}$ ed).

Immunosuppressive agents include glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, buslfan, and cyclophosphamide), folic acid antagonsists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

The foregoing and other useful combination therapies will be understood and appreciated by those of skill in the art. Potential advantages of such combination therapies include a different efficacy profile, the ability to use less of each of the individual active ingredients to minimize toxic side effects, synergistic improvements in efficacy, improved ease of administration or use and/or reduced overall expense of compound preparation or formulation.

Other Embodiments

The compounds of this invention may be used as research tools (for example, as a positive control for evaluating other potential CRAC inhibitors, or IL-2, IL-4, IL-5, IL-13, GM-CSF, TNF-$\alpha$, and/or INF-$\gamma$ inhibitors). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Experimental Rationale

Without wishing to be bound by theory, it is believed that the compounds of this invention inhibit CRAC ion channels, thereby inhibiting production of IL-2 and other key cytokines involved with inflammatory, allergic and immune responses. The examples that follow demonstrate these properties.

Materials and General Methods

Reagents and solvents used below can be obtained from commercial sources such as Aldrich Chemical Co. (Milwaukee, Wis., USA). $^1$H-NMR and $^{13}$C-NMR spectra were recorded on a Varian 300 MHz NMR spectrometer. Significant peaks are tabulated in the order: $\delta$ (ppm): chemical shift, multiplicity (s, singlet; d, doublet; t, triplet; q, quartet; m, multiplet; br s, broad singlet), coupling constant(s) in Hertz (Hz) and number of protons.

Patch clamp experiments were performed in the tight-seal whole-cell configuration at 21-25° C. High resolution current recordings were acquired by a computer-based patch clamp amplifier system (EPC-9, HEKA, Lambrecht, Germany). Patch pipettes had resistances between 2-4 MO after filling with the standard intracellular solution. Immediately following establishment of the whole-cell configuration, voltage ramps of 50-200 ms duration spanning the voltage range of −100 to +100 mV were delivered at a rate of 0.5 Hz over a period of 300-400 seconds. All voltages were corrected for a liquid junction potential of 10 mV between external and internal solutions when using glutamate as the intracellular anion. Currents were filtered at 2.9 kHz and digitized at 10 μs intervals. Capacitive currents and series resistance were determined and corrected before each voltage ramp using the automatic capacitance compensation of the EPC-9. The low resolution temporal development of membrane currents was assessed by extracting the current amplitude at −80 mV or +80 mV from individual ramp current records.

Example 1

Synthesis of Representative Exemplary Compounds of this Invention

In general, the compounds of the invention can be synthesized using methods analogous to those described in U.S.

patent application Ser. No. 10/897,681 and U.S. Provisional Patent Application Ser. No. 60/611,913, the entire teachings of these patent applications are incorporated herein by reference.

Compound 1: N-[5-(2-Chloro-5-trifluoromethyl-phenyl)-pyrazin-2-yl]-2,6-difluoro-benzamide

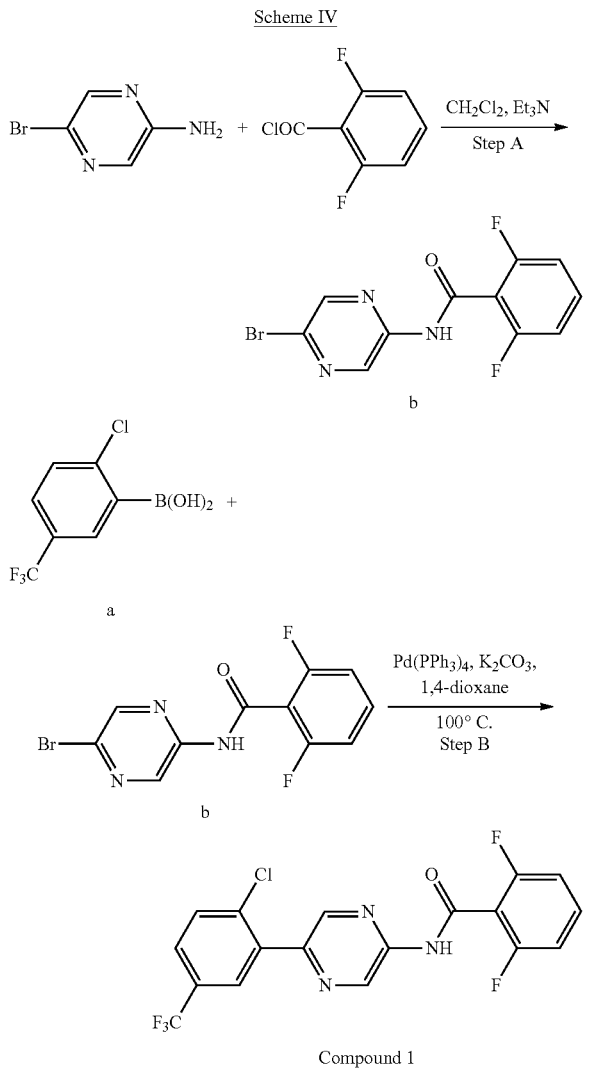

Step A: To a stirred solution of 2-bromo-5-amino-pyrazine (24 mmol), triethyl amine (TEA) (5 mL) in dry dichloromethane (DCM) (50 mL) at 00° C. was added 2,6-difluoro-benzoyl chloride (3.0 mL, 24 mmol) dropwise. The mixture was allowed to warm to room temperature over 2 h before it was washed with water (2×100 mL) and dried. Removal of solvents gave N-(5-bromo-pyrazin-2-yl)-2,6-difluorobenzamide (b) as white solid.

A mixture of 2-chloro-5-trifluoromethyl-benzeneboronic acid (a, 5 mmol), N-(5-bromo-pyrazin-2-yl)-2,6-difluoro-benzamide (b, 5 mmol), palladium catalyst (0.30 mmol), potassium carbonate (1 g) in dry 1,4-dioxane (20 mL) was heated at 100° C. for 24 h. The mixture was taken up with ethyl acetate (EtOAc) (100 mL), washed with water (2×100 mL) and dried over $Na_2SO_4$. The oil obtained on concentration was purified by flash chromatography followed by recrystallization to give Compound 1 as a yellowish solid (0.19 g).

$^1$H-NMR (CDCl$_3$) δ9.81 (s, 1H), 9.3 (br, 1H), 8.5 (d, 1H, J=2), 7.91 (s, 1H), 7.6 (d, 2H, J=2), 7.4 (m, 1H), 7.0 (t, 2H, J=8) ppm; ESMS calcd for $C_{18}H_9ClF_5N_3O$: 413.0. found: 413.9 (M+H$^+$).

Compound 2: N-[5-(2-Chloro-5-trifluoromethyl-phenyl)-pyrazin-2-yl]-3-fluoro-isonicotinamide Compound 2 was prepared in an analogous fashion to Compound 1 except that 3-fluoro-isonicotinoyl chloride was used instead of 2,6-difluoro-benzoyl chloride.

$^1$H-NMR (CDCl$_3$) δ 9.81 (s, 1H), 9.1 (br, 1H), 8.6-8.8 (m, 3H), 8.1 (t, 1H, J=6), 7.98 (s, 1H), 7.66 (s, 2H), 7.26 (s, 1H) ppm; ESMS calcd for $C_{17}H_9ClF_4N_4O$: 396.0. found: 397.0 (M+H$^+$).

Compound 3: N-[5-(2-Chloro-5-trifluoromethyl-phenyl)-pyrazin-2-yl]-3-methyl-isonicotinamide Compound 3 was prepared in an analogous fashion to Compound 1 except that 3-methyl-isonicotinoyl chloride was used instead of 2,6-difluoro-benzoyl chloride.

$^1$H-NMR (CDCl$_3$) 9.8 (d, 1H, J=3), 8.7 (d, 1H, J=3), 8.6 (m, 2H), 8.43 (s, 1H), 7.96 (s, 1H), 7.6 (d, 2H, J=5), 7.4 (d, 1H, J=5), 7.2 (d, 1H, J=5), 2.55 (s, 3H) ppm; ESMS calcd for $C_{18}H_{12}ClF_3N_4O$: 392.1. found: 393.0 (M+H$^+$).

Compound 4: N-[5-(2-Chloro-5-trifluoromethyl-phenyl)-pyrazin-2-yl]-2,6-difluoro-benzamide hydrochloride Compound 4 was prepared by suspending Compound 1 in methanol and bubbling HCl gas through the suspension until all solids went into solution. The solvent was then removed to give Compound 4, the HCl salt of Compound 1.

$^1$H-NMR (DMSO-d$_6$) δ 11.91 (s, 1H), 9.6 (br, 1H), 8.9 (d, 1H, J=2), 8.05 (s, 1H), 7.91 (s, 2H), 7.6 (m, 1H), 7.3 (t, 2H, J=8), 3.8 (br, 1H), ppm; ESMS calcd for $C_{18}H_{10}Cl_2F_5N_3O$: 449.0. found: 413.9 (M–Cl$^-$).

Compound 60: N-[6-(2-Chloro-5-trifluoromethyl-phenyl)-pyridazin-3-yl]-2,6-difluoro-benzamide Compound 60 was prepared in an analogous fashion to Compound 1 except that 3-bromo-6-amino-pyridazine was used instead of 2-bromo-5-amino-pyrazine.

$^1$H-NMR (CDCl$_3$) δ 9.5 (br, 1H), 8.7 (d, 1H, J=9), 8.0 (t, 1H, J=9), 8.0 (br, 1H), 7.7 (d, 2H, J=2), 7.4 (m, 1H), 7.0 (t, 2H, J=8) ppm; ESMS calcd for $C_{18}H_9ClF_5N_3O$: 413.0. found: 414.0 (M+H$^+$).

The compounds listed below were prepared by a method analogous to that described for Compound 1, 2, 3, 4, and 60

Compound 6: 3-[5-(2,6-Difluoro-benzoylamino)-pyrazin-2-yl]-4-methyl-benzoic acid methyl ester $^1$H-NMR (CDCl$_3$) 9.77 (s, 1H), 8.4 (m, 2H), 8.11 (s, 1H), 8.0 (d, 1H, J=8), 7.5 (m, 1H), 7.4 (d, 1H, J=8), 7.1 (t, 2H, J=8), 3.93 (s, 3H), 2.48 (s, 3H) ppm; ESMS calcd for $C_{20}H_{15}F_2N_3O_3$: 383.1. found: 384.0 (M+H$^+$).

Compound 32: 3-{5-[(3,5-Difluoro-pyridine-4-carbonyl)-amino]-pyrazin-2-yl}-4-methyl-benzoic acid methyl ester $^1$H-NMR (CDCl$_3$) δ9.8 (br, 1H), 8.6 (m, 2H), 8.48 (s, 2H), 8.10 (s, 1H), 8.0 (d, 1H, J=8), 7.4 (d, 1H, J=8), 3.92 (s, 3H), 2.47 (s, 3H) ppm; ESMS calcd for C$_{19}$H$_{14}$F$_2$N$_4$O$_3$: 384.1. found: 385.0 (M+H$^+$).

Compound 57: 2,6-Difluoro-N-[5-(2-methyl-5-oxazol-2-yl-phenyl)-pyrazin-2-yl]-benzamide $^1$H-NMR (CDCl$_3$) δ9.79 (s, 1H), 8.87 (s, 1H), 8.4 (d, 1H, J=2), 8.1 (d, 1H, J=2), 8.0 (d, 1H, J=8), 7.72 (s, 1H), 7.5 (m, 2H), 7.3 (d, 1H, J=8), 7.1 (t, 2H, J=8), 2.47 (s, 3H) ppm; ESMS calcd for C$_{21}$H$_{14}$F$_2$N$_4$O$_2$: 392.1. found: 393.1 (M+H$^+$).

Compound 61: 3-Fluoro-N-[5-(2-methyl-5-oxazol-2-yl-phenyl)-pyrazin-2-yl]-isonicotinamide $^1$H-NMR (CDCl$_3$) δ9.78 (s, 1H), 8.86 (s, 1H), 8.6 (m, 2H), 8.42 (s, 1H), 8.14 (s, 1H), 8.0 (d, 1H, J=8), 7.70 (s, 1H), 7.4 (m, 2H), 7.20 (s, 1H), 2.52 (s, 3H), 2.43 (s, 3H) ppm; ESMS calcd for C$_{20}$H$_{14}$FN$_5$O$_2$: 375.1. found: 376.1 (M+H$^+$).

Compound 62: 3-Methyl-N-[5-(2-methyl-5-oxazol-2-yl-phenyl)-pyrazin-2-yl]-isonicotinamide $^1$H-NMR (CDCl$_3$) δ9.78 (s, 1H), 8.86 (s, 1H), 8.6 (m, 2H), 8.42 (s, 1H), 8.14 (s, 1H), 8.0 (d, 1H, J=8), 7.70 (s, 1H), 7.4 (m, 2H), 7.20 (s, 1H), 2.52 (s, 3H), 2.43 (s, 3H) ppm; ESMS calcd for C$_{21}$H$_{17}$N$_5$O$_2$: 371.1. found: 372.1 (M+H$^+$).

Compound 63: 3,5-Difluoro-N-[5-(2-methyl-5-oxazol-2-yl-phenyl)-pyrazin-2-yl]-isonicotinamide $^1$H-NMR (CDCl$_3$) δ9.73 (s, 1H), 9.11 (br, 1H), 8.5 (m, 3H), 8.17 (s, 1H), 8.0 (d, 1H, J=8), 7.70 (s, 1H), 7.4 (d, 1H, J=8), 7.18 (s, 1H), 2.48 (s, 3H) ppm; ESMS calcd for C$_{20}$H$_{13}$F$_2$N$_5$O$_2$: 393.1. found: 394.1 (M+H$^+$).

Compound 64: 4-Methyl-[1,2,3]thiadiazole-5-carboxylic acid [5-(2-methyl-5-oxazol-2-yl-phenyl)-pyrazin-2-yl]-amide $^1$H-NMR (CDCl$_3$) δ9.69 (s, 1H), 8.52 (s, 1H), 8.4 (br, 1H), 8.14 (s, 1H), 8.0 (d, 1H, J=8), 7.73 (s, 1H), 7.4 (d, 1H, J=8), 7.2 (m, 1H), 3.06 (s, 3H), 2.48 (s, 3H) ppm; ESMS calcd for C$_{18}$H$_{14}$N$_6$O$_2$S: 378.1. found: 379.1 (M+H$^+$).

Compound 109: 3-{5-[(3-Fluoro-pyridine-4-carbonyl)-amino]-pyrazin-2-yl}-4-methyl-benzoic acid methyl ester $^1$H-NMR (CDCl$_3$) δ9.77 (s, 1H), 9.0 (br, 1H), 8.7 (m, 2H), 8.50 (s, 1H), 8.1 (m, 3H), 7.4 (d, 1H, J=8), 3.93 (s, 3H), 2.49 (s, 3H) ppm; ESMS calcd for C$_{19}$H$_{15}$FN$_4$O$_3$: 366.1. found: 367.1 (M+H$^+$).

Compound 110: N-[5-(2,5-Dimethoxy-phenyl)-pyrazin-2-yl]-2,6-difluoro-benzamide $^1$H-NMR (CDCl$_3$) δ9.78 (s, 1H), 9.2 (br, 1H), 8.67 (s, 1H), 7.4 (m, 2H), 7.0 (m, 4H), 3.83 (s, 6H) ppm; ESMS calcd for C$_{19}$H$_{15}$F$_2$N$_3$O$_3$: 371.1. found: 372.1 (M+H$^+$).

Compound 111: N-[5-(2-Chloro-5-trifluoromethyl-phenyl)-pyrazin-2-yl]-2-methyl-nicotinamide $^1$H-NMR (CDCl$_3$) δ9.81 (s, 1H), 8.7 (m, 2H), 8.3 (br, 1H), 7.96 (s, 1H), 7.9 (d, 1H, J=8), 7.65 (s, 2H), 7.3 (m, 1H), 2.81 (s, 3H) ppm; ESMS calcd for C$_{18}$H$_{12}$ClF$_3$N$_4$O: 392.1. found: 393.0 (M+H$^+$).

Compound 112: Cyclohexanecarboxylic acid [5-(2-chloro-5-trifluoromethyl-phenyl)-pyrazin-2-yl]-amide $^1$H-NMR (CDCl$_3$) δ9.68 (s, 1H), 8.67 (s, 1H), 7.9 (m, 2H), 7.63 (s, 2H), 2.4 (m, 1H), 2.0 (m, 2H), 1.2-1.9 (m, 8H) ppm; ESMS calcd for C$_{18}$H$_{17}$ClF$_3$N$_3$O: 383.1. found: 384.1 (M+H$^+$).

Compound 113: N-[5-(2,5-Dimethoxy-phenyl)-pyrazin-2-yl]-3-fluoro-isonicotinamide $^1$H-NMR (CDCl$_3$) δ9.73 (s, 1H), 9.0 (br, 1H), 8.99 (s, 1H), 8.7 (m, 2H), 8.0 (m, 1H), 7.51 (s, 1H), 7.0 (m, 2H), 3.86 (s, 6H) ppm; ESMS calcd for C$_{18}$H$_{15}$FN$_4$O$_3$: 354.1. found: 355.1 (M+H$^+$).

Compound 114: 4-Methyl-[1,2,3]thiadiazole-5-carboxylic acid [5-(2-chloro-5-trifluoromethyl-phenyl)-pyrazin-2-yl]-amide $^1$H-NMR (CDCl$_3$) δ9.73 (s, 1H), 8.75 (s, 1H), 8.6 (br, 1H), 7.96 (s, 1H), 7.66 (s, 2H), 3.05 (s, 3H) ppm; ESMS calcd for C$_{15}$H$_9$ClF$_3$N$_5$OS: 399.0. found: 400.0 (M+H$^+$).

Compound 115: N-[5-(2-Chloro-5-trifluoromethyl-phenyl)-pyrazin-2-yl]-3,5-difluoro-isonicotinamide $^1$H-NMR (CDCl$_3$) δ9.78 (s, 1H), 8.76 (s, 1H), 8.58 (s, 2H), 8.5 (br, 1H), 7.96 (s, 1H), 7.66 (s, 2H) ppm; ESMS calcd for C$_{17}$H$_8$ClF$_5$N$_4$O: 414.0. found: 415.0 (M+H$^+$).

Compound 117: N-[5-(2,5-Dimethoxy-phenyl)-pyrazin-2-yl]-3-methyl-isonicotinamide $^1$H-NMR (CDCl$_3$) δ9.71 (s, 1H), 8.92 (s, 1H), 8.6 (m, 2H), 8.2 (br, 1H), 7.5 (m, 2H), 7.0 (m, 2H), 3.87 (s, 6H), 2.55 (s, 3H) ppm; ESMS calcd for C$_{19}$H$_{18}$N$_4$O$_3$: 350.1. found: 351.1 (M+H$^+$).

Compound 118: N-[5-(2,5-Dimethoxy-phenyl)-pyrazin-2-yl]-3,5-difluoro-isonicotinamide $^1$H-NMR (CDCl$_3$) δ9.70 (s, 1H), 9.0 (br, 1H), 8.89 (s, 1H), 8.51 (s, 2H), 7.49 (s, 1H), 6.96 (s, 2H), 3.85 (s, 6H) ppm; ESMS calcd for C$_{18}$H$_{14}$F$_2$N$_4$O$_3$: 372.1. found: 373.1 (M+H$^+$).

Compound 119: 4-Methyl-[1,2,3]thiadiazole-5-carboxylic acid [5-(2,5-dimethoxy-phenyl)-pyrazin-2-yl]-amide $^1$H-NMR (CDCl$_3$) δ9.65 (s, 1H), 8.96 (s, 1H), 8.8 (br, 1H), 7.5 (d, 1H, J=2), 7.4 (d, 1H, J=2), 7.26 (s, 1H), 6.8 (m, 2H), 6.37 (s, 1H), 3.85 (s, 6H), 3.03 (s, 3H) ppm; ESMS calcd for $C_{16}H_{15}N_5O_3S$: 357.1. found: 358.1 (M+H$^+$).

Compound 120: Cyclohexanecarboxylic acid [5-(2,5-dimethoxy-phenyl)-pyrazin-2-yl]-amide $^1$H-NMR (CDCl$_3$) δ 8.92 (s, 1H), 8.86 (s, 1H), 8.0 (br, 1H), 7.46 (s, 1H), 6.95 (s, 2H), 3.84 (s, 6H), 2.4 (m, 1H), 1.4-2.1 (m, 10H) ppm; ESMS calcd for $C_{19}H_{23}N_3O_3$: 341.2. found: 342.1 (M+H$^+$).

Compound 121: Cyclohexanecarboxylic acid [5-(2-methyl-5-oxazol-2-yl-phenyl)-pyrazin-2-yl]-amide $^1$H-NMR (CDCl$_3$) δ 9.64 (d, 1H, J=2), 8.42 (d, 1H, J=2), 8.1 (d, 1H, J=2), 8.0 (dd, 1H, $J_1$=8, $J_2$=2), 7.9 (br, 1H), 7.71 (s, 1H), 7.4 (d, 1H, J=8), 7.2 (m, 2H). 2.43 (s, 3H), 2.4 (m, 1H), 1.4-2.1 (m, 10H) ppm; ESMS calcd for $C_{21}H_{22}N_4O_2$: 362.2. found: 363.2 (M+H$^+$).

Compound 116: N-[5-(2-Chloro-5-trifluoromethyl-phenyl)-pyrimidin-2-yl]-2,6-difluoro-benzamide The above aminopyrimidine e (0.26 g, 0.9 mmol) was dissolved in dichloromethane (DCM) (5 mL) and pyridine (0.1 mL) and 2,6-difluorobenzoyl chloride (0.9 mmol) was added. The reaction was stirred for 24 h. Removal of solvent and column purification gave N-[5-(2-chloro-5-trifluoromethyl-phenyl)-pyrimidin-2-yl]-2,6-difluoro-benzamide (Compound 116, 10 mg) as white solid.

$^1$H-NMR (CDCl$_3$) δ 8.9 (br, 1H), 8.70 (s, 2H), 7.7 (m, 2H), 7.57 (s, 1H), 7.4 (m, 1H), 7.0 (t, 2H, J=8) ppm; ESMS calcd for $C_{18}H_9ClF_5N_3O$: 413.0. found: 414.0 (M+H$^+$).

Compound 122: N-[2-(2-Chloro-5-trifluoromethyl-phenyl)-pyrimidin-5-yl]-2,6-difluoro-benzamide

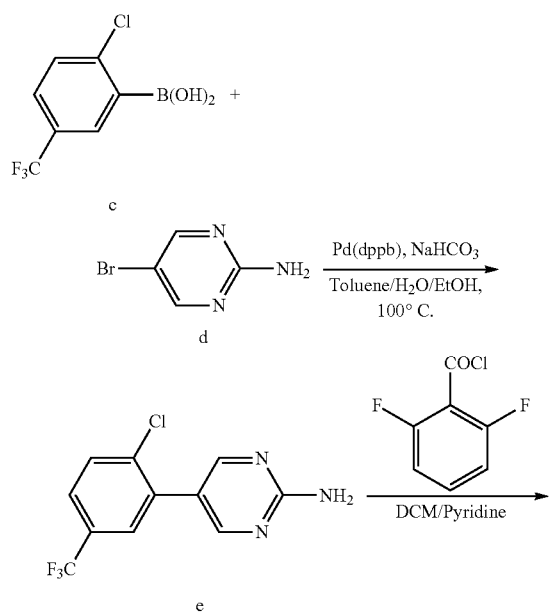

Compound 116

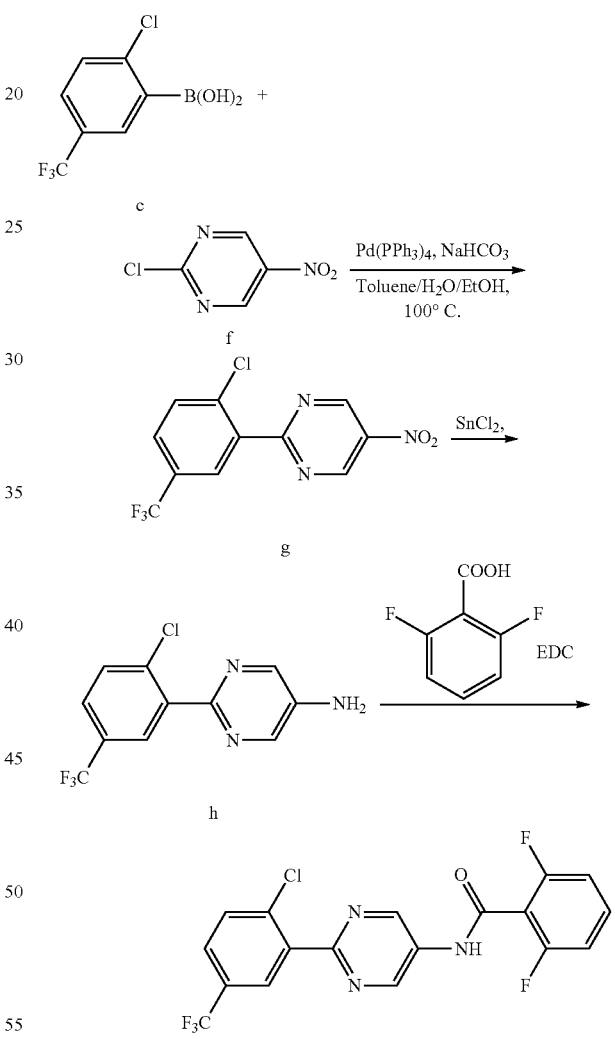

Compound 122

A mixture of 2-chloro-5-trifluoromethyl-benzeneboronic acid (c, 1.5 mmol), 5-bromo-pyrimidin-2-ylamine (d, 1.5 mmol), Pd(PhCN)$_2$Cl$_2$ (0.10 mmol), DPPB (0.10 mmol), sodium bicarbonate (2 mmol) in a mixture of toluene (20 mL), water (5 mL), ethanol (2 mL) was heated at 100° C. for 24 h. The mixture was taken up with ethyl acetate (EtOAc) (100 mL), washed with water (2×100 mL) and dried (Na$_2$SO$_4$). The oil obtained on concentration was purified by flash chromatography to give e as a white solid (0.26 g).

A mixture of 2-chloro-5-trifluoromethyl-benzeneboronic acid (c, 200 mg), 2-chloro-5-nitro-pyrimidine (f, 100 mg), Pd(PPh$_3$)$_4$ (0.05 mmol), sodium bicarbonate (2 mmol) in a mixture of toluene (20 mL), water (5 mL), ethanol (2 mL) was heated at 80° C. for 24 h. The mixture was taken up with EtOAc (100 mL), washed with water (2×100 mL) and dried (Na$_2$SO$_4$). The oil obtained on concentration was passed through a layer of silica gel to get compound g as a crude mixture.

The above mixture was treated with SnCl₂ (200 mg) in ethanol (EtOH) (5 mL) for 16 h. The mixture was diluted with water (50 mL) and extracted with DCM (2×50 mL). The DCM layer was dried, evaporated and passed through silica gel to afford compound h as a crude mixture.

The above mixture was treated with 2,6-difluorobenzoic acid (100 mg) and EDC (150 mg) in DCM (5 mL) for 16 h. The mixture was washed with water and purified by column chromatography to give N-[2-(2-chloro-5-trifluoromethyl-phenyl)-pyrimidin-5-yl]-2,6-difluoro-benzamide as white solid (Compound 122, 10 mg).

$^1$H-NMR (CDCl$_3$) δ9.28 (s, 2H), 8.09 (s, 1H), 8.0 (br, 1H), 7.63 (s, 2H), 7.5 (m, 1H), 7.1 (t, 2H, J=8) ppm; ESMS calcd for $C_{18}H_9ClF_5N_3O$: 413.0. found: 414.0 (M+H$^+$).

Example 2

Inhibition of IL-2 Production

Jurkat cells were placed in a 96 well plate (0.5 million cells per well in 1% FBS medium) then a test compound of this invention was added at different concentrations. After 10 minutes, the cells were activated with PHA (final concentration 2.5 μg/mL) and incubated for 20 hours at 37° C. under CO$_2$. The final volume was 200 μL. Following incubation, the cells were centrifuged and the supernatants collected and stored at −70° C. prior to assaying for IL-2 production. A commercial ELISA kit (IL-2 Eli-pair, Diaclone Research, Besancon, France) was used to detect production of IL-2, from which dose response curves were obtained. The IC$_{50}$ value was calculated as the concentration at which 50% of maximum IL-2 production after stimulation was inhibited versus a non-stimulation control.

| Compound # | IC$_{50}$ |
| --- | --- |
| 1 | 2 nM |
| 2 | 115 nM |
| 4 | 6 nM |
| 60 | >1000 nM |
| 61 | 50.5 nM |
| 62 | 32.2 nM |
| 63 | 18.5 nM |
| 64 | 55.0 nM |
| 109 | 49.2 nM |
| 110 | 15.7 nM |
| 111 | 133.1 nM |
| 112 | 22.3 nM |
| 113 | 207.2 nM |
| 114 | 61.6 nM |
| 115 | 4.1 nM |
| 116 | 118.2 nM |
| 117 | 144.7 nM |
| 118 | 34.0 nM |
| 119 | 302.4 nM |
| 120 | 352.5 nM |
| 121 | 38.5 nM |
| 122 | 653.8 nM |

Inhibition of other cytokines, such as IL-4, IL-5, IL-13, GM-CSF, TNF-α, and INF-γ, can be tested in a similar manner using a commercially available ELISA kit for each cytokine.

Example 3

Patch Clamp Studies of Inhibition of I$_{CRAC}$ Current in RBL Cells, Jurkat Cells, and Primary T Cells In general, a whole cell patch clamp method was used to examine the effects of a compound of the invention on a channel that mediates I$_{crac}$. In such experiments, a baseline measurement was established for a patched cell. Then a compound to be tested was perfused (or puffed) to cells in the external solution and the effect of the compound on I$_{crac}$ was measured. A compound that modulates I$_{crac}$ (e.g., inhibits) is a compound that is useful in the invention for modulating CRAC ion channel activity.

1) RBL cells

Cells

Rat basophilic leukemia cells (RBL-2H3) were grown in DMEM media supplemented with 10% fetal bovine serum in an atmosphere of 95% air/5% CO$_2$. Cells were seeded on glass coverslips 1-3 days before use.

Recording Conditions

Membrane currents of individual cells were recorded using the whole-cell configuration of the patch clamp technique with an EPC10 (HEKA Electronik, Lambrecht, Germany). Electrodes (2-5 MO in resistance) were fashioned from borosilicate glass capillary tubes (Sutter Instruments, Novato, Ca). The recordings were done at room temperature.

Intracellular Pipette Solution

The intracellular pipette solution contained Cs-Glutamate 120 mM; CsCl 20 mM; CsBAPTA 10 mM; CsHEPES 10 mM; NaCl 8 mM; MgCl$_2$ 1 mM; IP3 0.02 mM; pH=7.4 adjusted with CsOH. The solution was kept on ice and shielded from light before the experiment was preformed.

Extracellular Solution

The extracellular solution contained NaCl 138 mM; NaHEPES, 10 mM; CsCl 10 mM; CaCl$_2$ 10 mM; Glucose 5.5 mM; KCl 5.4 mM; KH$_2$PO$_4$ 0.4 mM; Na$_2$HPO$_4$.H$_2$O 0.3 mM at pH=7.4 adjusted with NaOH.

Compound Treatment

Each compound was diluted from a 10 mM stock in series using DMSO. The final DMSO concentration was always kept at 0.1%.

Experimental Procedure

I$_{CRAC}$ currents were monitored every 2 seconds using a 50 msec protocol, where the voltage was ramped from −100 mV to +100 mV. The membrane potential was held at 0 mV between the test ramps. In a typical experiment, the peak inward currents would develop within 50-100 seconds. Once the I$_{CRAC}$ currents were stabilized, the cells were perfused with a test compound in the extracellular solution. At the end of an experiment, the remaining I$_{CRAC}$ currents were then challenged with a control compound (SKF96365, 10 μM) to ensure that the current could still be inhibited.

Data Analysis

The I$_{CRAC}$ current level was determined by measuring the inward current amplitude at −80 mV of the voltage ramp in an off-line analysis using MATLAB. The I$_{CRAC}$ current inhibition for each concentration was calculated using peak amplitude in the beginning of the experiment from the same cell. The IC$_{50}$ value and Hill coefficient for each compound was estimated by fitting all the individual data points to a single Hill equation.

Results

The table below shows the concentration of a compound of the invention which inhibits 50% of the I$_{CRAC}$ current in RBL cells. As can be seen from the data in the table, two representative compounds of the invention inhibit I$_{CRAC}$ current at concentration of 70 nM.

| Compound Number | IC$_{50}$ |
| --- | --- |
| 1 | 70 nM |
| 115 | 70 nM |
| SKF96365 | 4 μM |

2) Jurkat Cells

Cells

Jurkat T cells are grown on glass coverslips, transferred to the recording chamber and kept in a standard modified Ringer's solution of the following composition: NaCl-145 mM, KCl 2.8 mM, CsCl 10 mM, CaCl$_2$ 10 mM, MgCl$_2$ 2 mM, glucose 10 mM, HEPES-NaOH 10 mM, pH 7.2.

Extracellular Solution

The external solution contains 10 mM CaNaR, 11.5 mM glucose and a test compound at various concentrations.

Intracellular Pipette Solution

The standard intracellular pipette solution contains: Cs-glutamate 145 mM, NaCl 8 mM, MgCl$_2$ 1 mM, ATP 0.5 mM, GTP 0.3 mM, pH 7.2 adjusted with CsOH. The solution is supplemented with a mixture of 10 mM Cs-BAPTA and 4.3-5.3 mM CaCl$_2$ to buffer [Ca$^{2+}$]i to resting levels of 100-150 nM.

Patch-Clamp Recordings

Patch-clamp experiments are performed in the tight-seal whole-cell configuration at 21-25° C. High-resolution current recordings are acquired by a computer-based patch-clamp amplifier system (EPC-9, HEKA, Lambrecht, Germany). Sylgard®-coated patch pipettes typically have resistances between 2-4 MO after filling with the standard intracellular solution. Immediately following establishment of the whole-cell configuration, voltage ramps of 50 ms duration spanning the voltage range of −100 to +100 mV are delivered from a holding potential of 0 mV at a rate of 0.5 Hz over a period of 300 to 400 seconds. All voltages are corrected for a liquid junction potential of 10 mV between external and internal solutions. Currents are filtered at 2.3 kHz and digitized at 100 μs intervals. Capacitive currents and series resistance are determined and corrected before each voltage ramp using the automatic capacitance compensation of the EPC-9.

Data Analysis

The very first ramps before activation of I$_{CRAC}$ (usually 1 to 3) are digitally filtered at 2 kHz, pooled and used for leak-subtraction of all subsequent current records. The low-resolution temporal development of inward currents is extracted from the leak-corrected individual ramp current records by measuring the current amplitude at −80 mV or a voltage of choice.

Compounds of the invention are expected to inhibit I$_{CRAC}$ current in Jurkat cells.

3) Primary T Cells

Preparation of Primary T Cells

Primary T cells are obtained from human whole blood samples by adding 100 μL of RosetteSep® human T cell enrichment cocktail to 2 mL of whole blood. The mixture is incubated for 20 minutes at room temperature, then diluted with an equal volume of PBS containing 2% FBS. The mixture is layered on top of RosetteSep® DM-L density medium and then centrifuged for 20 minutes at 1200 g at room temperature. The enriched T cells are recovered from the plasma/density medium interface, then washed with PBS containing 2% FBS twice, and used in patch clamp experiments following the procedure described for RBL cells.

Compounds of the invention are expected to inhibit I$_{CRAC}$ current in human primary T cells.

Example 4

Inhibition of Multiple Cytokines in Primary Human PBMCs

Peripheral blood mononuclear cells (PBMCs) are stimulated with phytohemagglutinin (PHA) in the presence of varying concentrations of compounds of the invention or cyclosporine A (CsA), a known inhibitor of cytokine production. Cytokine production is measured using commercially available human ELISA assay kits (from Cell Science, Inc.) following the manufacturers instructions.

The compounds of the invention are potent inhibitors of IL-2, and are expected to be potent inhibitors of IL-4, IL-5, IL-13, GM-CSF, INF-γ and TNF-α in primary human PBM cells. In addition, compounds of the invention are not expected to inhibit the anti-inflammatory cytokine, IL-10.

Example 5

Compounds of the Invention are Potent Inhibitors of Degranulation in RBL Cells

Procedure:

The day before the assay is performed, RBL cells, that had been grown to confluence in a 96 well plate, are incubated at 37° C. for at least 2 hours. The medium is replaced in each well with 100 μL of fresh medium containing 2 μLg/mL of anti-DNP IgE.

On the following day, the cells are washed once with PRS (2.6 mM glucose and 0.1% BSA) and 160 μL of PRS was added to each well. A test compound is added to a well in a 20 μL solution at 10× of the desired concentration and incubated for 20 to 40 minutes at 37° C. 20 μL of 10× mouse anti-IgE (10 μL/mL) is added. SKF96365 is used as a positive control. Maximum degranulation typically occurs between 15 to 40 minutes after addition of anti-IgE.

Results:

Compounds of the invention are expected to inhibit degranulation of RBL cells.

Example 6

Compounds of the Invention are Potent Inhibitors of Chemotaxis in T Cells

T-Cell Isolation:

Twenty ml aliquots of heparinized whole blood (2 pig, 1 human) are subjected to density gradient centrifugation on Ficoll Hypaque. The buffy coat layers representing peripheral blood mononuclear cells (PBMCs) containing lymphocytes and monocytes are washed once, resuspended in 12 ml of incomplete RPMI 1640 and then placed in gelatin-coated T75 culture flasks for 1 hr at 37° C. The non-adherent cells, representing peripheral blood lymphocytes (PBLs) depleted of monocytes, are resuspended in complete RPMI media and placed in loosely packed activated nylon wool columns that had been equilibrated with warm media. After 1 hr at 37° C., the non-adherent T cell populations are eluted by washing of the columns with additional media. The T cell preparations are centrifuged, resuspended in 5 ml of incomplete RPMI, and counted using a hemocytometer.

Cell Migration Assay:

Aliquots of each T cell preparation are labeled with Calcien AM (TefLabs) and suspended at a concentration of 2.4×10$^6$/ ml in HEPES-buffered Hank's Balanced Salt Solution containing 1.83 mM CaCl$_2$ and 0.8 mM MgCl$_2$, pH 7.4 (HH- BSS). An equal volume of HHBSS containing 0, 20 nM, 200 nM or 2000 nM of compound 1 or 20 nM EDTA is then added and the cells are incubated for 30 min at 37° C. Fifty μl aliquots of the cell suspensions (60,000 cells) are placed on the membrane (pore size 5 m) of a Neuroprobe ChemoTx 96 well chemotaxis unit that had been affixed over wells containing 10 ng/ml MIP-1α in HHBSS. The T cells are allowed to migrate for 2 hr at 37° C., after which the apical surface of the membrane is wiped clean of cells. The chemotaxis units are then placed in a CytoFlour 4000 (PerSeptive BioSystems) and the fluorescence of each well is measured (excitation and emission wavelengths of 450 and 530 nm, respectively). The number of migrating cells in each well is determined from a standard curve generated from measuring the fluorescence of serial two-fold dilutions of the labeled cells placed in the lower wells of the chemotaxis unit prior to affixing the membrane.

Results:

Compounds of the invention are expected to be inhibitory to the chemotactic response of porcine T cells and in human T cells.

All publications, patent applications, patents, and other documents cited herein are incorporated by reference in their entirety. In case of conflict, the present specification, including definitions, will control. In addition, the materials, methods, and examples are illustrative only and not intended to be limiting in any way.

We claim:

1. A method of treating organ transplant rejection, psoriasis, atopic dermatitis, chronic autoimmune urticaria, rheumatoid arthritis, hemolytic anemia, ulcerative colitis, Crohn's disease, or uveitis in a subject in need thereof, comprising administering to the subject an effective amount of a compound represented by structural formula (V):

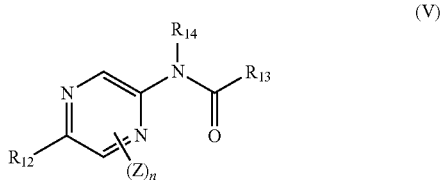

(V)

or a pharmaceutically acceptable salt thereof, wherein:
each Z is independently selected from the group consisting of a lower alkyl, a lower haloalkyl, a halo, a lower alkoxy, a lower alkyl sulfanyl, cyano, nitro, and lower haloalkoxy;
$R_{12}$ is an aryl or a heteroaryl, wherein the aryl and heteroaryl are optionally substituted with one or more substituents selected from the group consisting of alkyl, alkenyl, alkynyl, cycloalkyl, cycloalkenyl, heterocyclyl, aryl, heteroaryl, haloalkyl, aralkyl, heteraralkyl, a halo, cyano, nitro, —$OR_{17}$, —$SR_{17}$, —$S(O)_pR_{17}$, —$S(O)_pOR_{17}$, —$OS(O)_pR_{17}$, —$OS(O)_pOR_{17}$, —$NR_{17}S(O)_pR_{17}$, —$S(O)_pNR_{15}R_{16}$, —$NR_{15}R_{16}$, —$C(X_3)R_{17}$, —$C(X_3)OR_{17}$, —$C(X_3)SR_{17}$, —$C(X_3)NR_{15}R_{16}$, —$NR_{17}C(X_3)R_{18}$, —$NR_{17}C(X_3)OR_{18}$, —$NR_{17}C(X_3)SR_{18}$, —$NR_{17}C(X_3)NR_{15}R_{16}$, —$OC(X_3)R_{17}$, —$OC(X_3)OR_{17}$, —$OC(X_3)SR_{17}$, —$SC(X_3)OR_{17}$, —$SC(X_3)SR_{17}$, —$OC(X_3)NR_{15}R_{16}$, —$SC(X_3)NR_{15}R_{16}$, —$P(X_4)(X_5R_{17})_2$, —$X_5P(X_4)(X_5R_{17})_2$, —$P(X_4)(R_{17})_2$, and —$P(X_4)(R_{17})(X_5R_{17})$;
$R_{13}$ is a cycloalkyl, a cycloalkenyl, an aryl, or a heteroaryl, wherein the cycloalkyl, cycloalkenyl, aryl, or heteroaryl are optionally substituted with one or more substituents selected from the group consisting of a lower alkyl, a halo, cyano, nitro, a lower haloalkyl, a lower alkoxy, a lower sulfanylalkyl, —$S(O)_pR_{31}$, —$S(O)_pNR_{29}R_{30}$, —$NR_{29}R_{30}$, —$C(O)R_{28}$, —$C(O)OR_{28}$, —$C(O)NR_{29}R_{30}$, —$NR_{29}C(O)R_{30}$, —$NR_{29}C(O)OR_{28}$, —$NR_{28}C(O)NR_{29}R_{30}$, —$OC(O)R_{28}$, —$OC(O)OR_{28}$, and —$OC(O)NR_{29}R_{30}$; wherein $R_{28}$, $R_{29}$, $R_{30}$, for each occurrence are, independently, H or a lower alkyl; and $R_{31}$, for each occurrence, is independently a lower alkyl;
$R_{14}$, for each occurrence is independently —H, an alkyl, —$C(O)R_{20}$, or —$C(O)OR_{20}$;
$R_{15}$ and $R_{16}$, for each occurrence are, independently, H, alkyl, alkenyl, alkynyl, cycloalkyl, cycloalkenyl, heterocyclyl, aryl, heteroaryl, aralkyl, or heteraralkyl; or $R_{15}$ and $R_{16}$ are taken together with the nitrogen to which they are attached to form heterocyclyl or heteroaryl;
$R_{17}$ and $R_{18}$, for each occurrence are, independently, H, alkyl, alkenyl, alkynyl, cycloalkyl, cycloalkenyl, heterocyclyl, aryl, heteroaryl, aralkyl, or heteraralkyl;
$R_{19}$, for each occurrence, is independently —H, a halo, an alkyl, —$OR_{17}$, —$NR_{15}R_{16}$, —$C(O)R_{17}$, —$C(O)OR_{17}$, or —$C(O)NR_{15}R_{16}$;
$R_{20}$, for each occurrence, is independently, H or an alkyl;
$X_3$ is =O, =S, or =N—$R_{19}$;
$X_4$ is =O or =S;
$X_5$ is —O— or —S—;
n is 0, 1 or 2; and
p is 1 or 2.

2. The method of claim 1, wherein $R_{12}$ is selected from the group consisting of phenyl, naphthyl, anthracenyl, pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, thiadiazolyl, quinolinyl, isoquinolinyl, indazolyl, benzofuryl, imidazopyridinyl, tetrazolyl, benzoxazolyl, benzothiazolyl, benzothiadiazolyl, benzoxadiazolyl, indolyl, azaindolyl, quinazolinyl, purinyl, pyrrolo[2,3]pyrimidyl, pyridopyrimidyl, pyrazolo[3,4]pyrimidyl, and benzo(b)thienyl.

3. The method of claim 2, wherein $R_{12}$ is phenyl, tetrazolyl, or pyridinyl.

4. The method of claim 1, wherein $R_{13}$ is aryl or heteroaryl.

5. The method of claim 4, wherein $R_{13}$ is phenyl or pyridinyl.

6. The method of claim 5, wherein the compound is of formula (III):

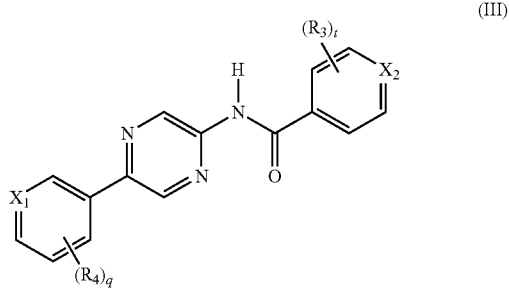

(III)

or a pharmaceutically acceptable salt thereof, wherein:
$X_1$ is CH, $CR_4$, or N;
$X_2$ is CH, $CR_3$, or N;
$R_3$, for each occurrence, is, independently, a halo, cyano, nitro, a lower alkyl, a lower haloalkyl, a lower alkoxy, a lower alkylsulfanyl, —NH$_2$, a lower alkylamino, a lower dialkylamino, or —C(O)R$_a$, where R$_a$ is H or lower alkyl;

R$_4$, for each occurrence, is, independently, a halo, cyano, nitro, an alkyl, an alkoxy, alkylsulfanyl, hydroxyl, a heteroaryl, —NH$_2$, alkylamino, dialkylamino, or —C(O)R$_6$;

R$_6$, for each occurrence, is independently, H, an alkyl, a cycloalkyl, a heterocyclyl, an aryl, a heteroaryl, an aralkyl, a heteraralkyl, —OR$_7$, —SR$_7$, or —NR$_7$R$_7$;

R$_7$, for each occurrence, is, independently, H, an alkyl, a cycloalkyl, a heterocyclyl, an aryl, a heteroaryl, an aralkyl, or a heteraralkyl; and q and t, for each occurrence are, independently, 0 or an integer from 1 to 4, inclusive.

7. The method of claim 6, wherein the compound is of formula (IV):

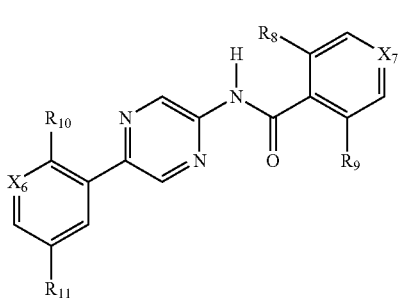

(IV)

or a pharmaceutically acceptable salt thereof, wherein:
X$_6$ and X$_7$ are each, independently, CH or N;
R$_8$ and R$_9$ are each, independently, a halo, a lower alkyl, a lower alkoxy, or a lower haloalkyl; and
R$_{10}$ and R$_{11}$, are each, independently, a halo, cyano, a lower alkyl, a lower alkoxy, a lower alkyl ester, —C(O)NH$_2$, furanyl, oxazolyl, oxadiazolyl, or tetrazolyl.

8. The method of claim 7, wherein R$_8$ and R$_9$ are fluoro.

9. The method of claim 1, wherein the compound is selected from the group consisting of:

N-[5-(2-Chloro-5-trifluoromethyl-phenyl)-pyrazin-2-yl]-2,6-difluoro-benzamide;
N-[5-(2-Chloro-5-trifluoromethyl-phenyl)-pyrazin-2-yl]-3-fluoro-isonicotinamide;
N-[5-(2-Chloro-5-trifluoromethyl-phenyl)-pyrazin-2-yl]-3-methyl-isonicotinamide;
N-[5-(2-Chloro-5-trifluoromethyl-phenyl)-pyrazin-2-yl]-2,6-difluoro-benzamide hydrochloride;
2,6-Difluoro-N-{5-[2-methyl-5-(1-methyl-1H-tetrazol-5-yl)-phenyl]-pyrazin-2-yl}-benzamide;
3-[5-(2,6-Difluoro-benzoylamino)-pyrazin-2-yl]-4-methyl-benzoic acid methyl ester;
4-Methyl-3-{5-[(3-methyl-pyridine-4-carbonyl)-amino]-pyrazin-2-yl}-benzoic acid methyl ester;
3-[5-(2,6-Difluoro-benzoylamino)-pyrazin-2-yl]-4-methyl-benzoic acid propyl ester;
3-[5-(2,6-Difluoro-benzoylamino)-pyrazin-2-yl]-4-methyl-benzoic acid 2-methoxy-ethyl ester;
4-Chloro-3-[5-(2,6-difluoro-benzoylamino)-pyrazin-2-yl]-benzoic acid methyl ester;
4-Chloro-3-[5-(2,6-difluoro-benzoylamino)-pyrazin-2-yl]-benzoic acid ethyl ester;
4-Chloro-3-[5-(2,6-difluoro-benzoylamino)-pyrazin-2-yl]-benzoic acid 2-methoxy-ethyl ester;
2,6-Difluoro-N-[5-(5-furan-2-yl-2-methoxy-pyridin-3-yl)-pyrazin-2-yl]-benzamide;
2,6-Difluoro-N-[5-(5-furan-3-yl-2-methoxy-pyridin-3-yl)-pyrazin-2-yl]-benzamide;
N-[5-(5-Chloro-2-methoxy-pyridin-3-yl)-pyrazin-2-yl]-2,6-difluoro-benzamide;
N-[5-(5-Bromo-2-methoxy-pyridin-3-yl)-pyrazin-2-yl]-2,6-difluoro-benzamide;
N-[5-(2-Ethyl-5-trifluoromethyl-phenyl)-pyrazin-2-yl]-2,6-difluoro-benzamide;
3-[5-(2,6-Difluoro-benzoylamino)-pyrazin-2-yl]-4-methyl-benzamide;
4-[5-(2,6-Difluoro-benzoylamino)-pyrazin-2-yl]-3-methyl-benzoic acid methyl ester;
4-[5-(2,6-Difluoro-benzoylamino)-pyrazin-2-yl]-3-methyl-benzoic acid ethyl ester;
4-[5-(2,6-Difluoro-benzoylamino)-pyrazin-2-yl]-3-methyl-benzoic acid 2-methoxy-ethyl ester;
3-Chloro-4-[5-(2,6-difluoro-benzoylamino)-pyrazin-2-yl]-benzoic acid methyl ester;
3-Chloro-4-[5-(2,6-difluoro-benzoylamino)-pyrazin-2-yl]-benzoic acid ethyl ester;
3-Chloro-4-[5-(2,6-difluoro-benzoylamino)-pyrazin-2-yl]-benzoic acid 2-methoxy-ethyl ester;
3-Fluoro-N-[5-(5-furan-2-yl-2-methoxy-pyridin-3-yl)-pyrazin-2-yl]-isonicotinamide;
3-Fluoro-N-[5-(5-furan-3-yl-2-methoxy-pyridin-3-yl)-pyrazin-2-yl]-isonicotinamide;
N-[5-(5-Chloro-2-methoxy-pyridin-3-yl)-pyrazin-2-yl]-3-fluoro-isonicotinamide;
N-[5-(5-Bromo-2-methoxy-pyridin-3-yl)-pyrazin-2-yl]-3-fluoro-isonicotinamide;
3-Fluoro-N-[5-(2-methyl-5-trifluoromethyl-phenyl)-pyrazin-2-yl]-isonicotinamide;
N-[5-(5-Carbamoyl-2-methyl-phenyl)-pyrazin-2-yl]-3-fluoro-isonicotinamide;
N-[5-(5-Cyano-2-methyl-phenyl)-pyrazin-2-yl]-3-fluoro-isonicotinamide;
3-{5-[(3,5-Difluoro-pyridine-4-carbonyl)-amino]-pyrazin-2-yl}-4-methyl-benzoic acid methyl ester;
3-{5-[(3,5-Difluoro-pyridine-4-carbonyl)-amino]-pyrazin-2-yl}-4-methyl-benzoic acid ethyl ester;
3-{5-[(3,5-Difluoro-pyridine-4-carbonyl)-amino]-pyrazin-2-yl}-4-methyl-benzoic acid 2-methoxy-ethyl ester;
4-Chloro-3-{5-[(3,5-difluoro-pyridine-4-carbonyl)-amino]-pyrazin-2-yl}-benzoic acid methyl ester;
4-Chloro-3-{5-[(3,5-difluoro-pyridine-4-carbonyl)-amino]-pyrazin-2-yl}-benzoic acid ethyl ester;
4-Chloro-3-{5-[(3,5-difluoro-pyridine-4-carbonyl)-amino]-pyrazin-2-yl}-benzoic acid 2-methoxy-ethyl ester;
3,5-Difluoro-N-[5-(5-furan-2-yl-2-methoxy-pyridin-3-yl)-pyrazin-2-yl]-isonicotinamide;
3,5-Difluoro-N-[5-(5-furan-3-yl-2-methoxy-pyridin-3-yl)-pyrazin-2-yl]-isonicotinamide;
N-[5-(5-Chloro-2-methoxy-pyridin-3-yl)-pyrazin-2-yl]-3,5-difluoro-isonicotinamide;
N-[5-(5-Bromo-2-methoxy-pyridin-3-yl)-pyrazin-2-yl]-3,5-difluoro-isonicotinamide;
N-[5-(2-Ethyl-5-trifluoromethyl-phenyl)-pyrazin-2-yl]-3,5-difluoro-isonicotinamide;
N-[5-(5-Carbamoyl-2-methyl-phenyl)-pyrazin-2-yl]-3,5-difluoro-isonicotinamide;
3,5-Difluoro-N-[5-(5-cyano-2-methyl-phenyl)-pyrazin-2-yl]-isonicotinamide;

4-Methyl-3-{5-[(3-methyl-pyridine-4-carbonyl)-amino]-pyrazin-2-yl}-benzoic acid ethyl ester;
4-Methyl-3-{5-[(3-methyl-pyridine-4-carbonyl)-amino]-pyrazin-2-yl}-benzoic acid 2-methoxy-ethyl ester;
4-Chloro-3-{5-[(3-methyl-pyridine-4-carbonyl)-amino]-pyrazin-2-yl}-benzoic acid methyl ester;
4-Chloro-3-{5-[(3-methyl-pyridine-4-carbonyl)-amino]-pyrazin-2-yl}-benzoic acid ethyl ester;
4-Chloro-3-{5-[(3-methyl-pyridine-4-carbonyl)-amino]-pyrazin-2-yl}-benzoic acid 2-methoxy-ethyl ester;
N-[5-(2-Chloro-5-furan-2-yl-phenyl)-pyrazin-2-yl]-3-methyl-isonicotinamide;
N-[5-(2-Chloro-5-furan-3-yl-phenyl)-pyrazin-2-yl]-3-methyl-isonicotinamide;
N-[5-(5-Chloro-2-methoxy-pyridin-3-yl)-pyrazin-2-yl]-3-methyl-isonicotinamide;
N-[5-(5-Bromo-2-methoxy-pyridin-3-yl)-pyrazin-2-yl]-3-methyl-isonicotinamide;
N-[5-(2-Ethyl-5-trifluoromethyl-phenyl)-pyrazin-2-yl]-3-methyl-isonicotinamide;
N-[5-(5-Carbamoyl-2-methyl-phenyl)-pyrazin-2-yl]-3-methyl-isonicotinamide;
N-[5-(5-Cyano-2-methyl-phenyl)-pyrazin-2-yl]-3-methyl-isonicotinamide;
2,6-Difluoro-N-[5-(2-methyl-5-oxazol-2-yl-phenyl)-pyrazin-2-yl]-benzamide;
2,6-Difluoro-N-{5-[2-methyl-5-(3-methyl-[1,2,4]oxadiazol-5-yl)-phenyl]-pyrazin-2-yl}-benzamide;
2,6-Difluoro-N-{5-[2-methyl-5-(1H-tetrazol-5-yl)-phenyl]-pyrazin-2-yl}-benzamide;
3-Fluoro-N-[5-(2-methyl-5-oxazol-2-yl-phenyl)-pyrazin-2-yl]-isonicotinamide;
3-Methyl-N-[5-(2-methyl-5-oxazol-2-yl-phenyl)-pyrazin-2-yl]-isonicotinamide;
3,5-Difluoro-N-[5-(2-methyl-5-oxazol-2-yl-phenyl)-pyrazin-2-yl]-isonicotinamide;
4-Methyl-[1,2,3]thiadiazole-5-carboxylic acid [5-(2-methyl-5-oxazol-2-yl-phenyl)-pyrazin-2-yl]-amide;
3-Fluoro-N-[5-(2-methyl-5-thiazol-2-yl-phenyl)-pyrazin-2-yl]-isonicotinamide;
3-Methyl-N-[5-(2-methyl-5-thiazol-2-yl-phenyl)-pyrazin-2-yl]-isonicotinamide;
3,5-Difluoro-N-[5-(2-methyl-5-thiazol-2-yl-phenyl)-pyrazin-2-yl]-isonicotinamide;
4-Methyl-[1,2,3]thiadiazole-5-carboxylic acid [5-(2-methyl-5-thiazol-2-yl-phenyl)-pyrazin-2-yl]-amide;
N-[5-(2-Chloro-5-oxazol-2-yl-phenyl)-pyrazin-2-yl]-3-fluoro-isonicotinamide;
N-[5-(2-Chloro-5-oxazol-2-yl-phenyl)-pyrazin-2-yl]-3-methyl-isonicotinamide;
N-[5-(2-Chloro-5-oxazol-2-yl-phenyl)-pyrazin-2-yl]-3,5-difluoro-isonicotinamide;
4-Methyl-[1,2,3]thiadiazole-5-carboxylic acid [5-(2-chloro-5-oxazol-2-yl-phenyl)-pyrazin-2-yl]-amide;
3-Fluoro-N-[5-(2-methyl-5-[1,3,4]oxadiazol-2-yl-phenyl)-pyrazin-2-yl]-isonicotinamide;
3-Methyl-N-[5-(2-methyl-5-[1,3,4]oxadiazol-2-yl-phenyl)-pyrazin-2-yl]-isonicotinamide;
3,5-Difluoro-N-[5-(2-methyl-5-[1,3,4]oxadiazol-2-yl-phenyl)-pyrazin-2-yl]-isonicotinamide;
4-Methyl-[1,2,3]thiadiazole-5-carboxylic acid [5-(2-methyl-5-[1,3,4]oxadiazol-2-yl-phenyl)-pyrazin-2-yl]-amide;
3-Fluoro-N-[5-(2-methyl-5-[1,3,4]thiadiazol-2-yl-phenyl)-pyrazin-2-yl]-isonicotinamide;
3-Methyl-N-[5-(2-methyl-5-[1,3,4]thiadiazol-2-yl-phenyl)-pyrazin-2-yl]-isonicotinamide;
3,5-Difluoro-N-[5-(2-methyl-5-[1,3,4]thiadiazol-2-yl-phenyl)-pyrazin-2-yl]-isonicotinamide;
4-Methyl-[1,2,3]thiadiazole-5-carboxylic acid [5-(2-methyl-5-[1,3,4]thiadiazol-2-yl-phenyl)-pyrazin-2-yl]-amide;
N-[5-(2-Chloro-5-[1,3,4]oxadiazol-2-yl-phenyl)-pyrazin-2-yl]-3-fluoro-isonicotinamide;
N-[5-(2-Chloro-5-[1,3,4]oxadiazol-2-yl-phenyl)-pyrazin-2-yl]-3-methyl-isonicotinamide;
N-[5-(2-Chloro-5-[1,3,4]oxadiazol-2-yl-phenyl)-pyrazin-2-yl]-3,5-difluoro-isonicotinamide;
4-Methyl-[1,2,3]thiadiazole-5-carboxylic acid [5-(2-chloro-5-[1,3,4]oxadiazol-2-yl-phenyl)-pyrazin-2-yl]-amide;
3-Fluoro-N-[5-(2-methyl-5-oxazol-5-yl-phenyl)-pyrazin-2-yl]-isonicotinamide;
3-Methyl-N-[5-(2-methyl-5-oxazol-5-yl-phenyl)-pyrazin-2-yl]-isonicotinamide;
3,5-Difluoro-N-[5-(2-methyl-5-oxazol-5-yl-phenyl)-pyrazin-2-yl]-isonicotinamide;
4-Methyl-[1,2,3]thiadiazole-5-carboxylic acid [5-(2-methyl-5-oxazol-5-yl-phenyl)-pyrazin-2-yl]-amide;
3-Fluoro-N-[5-(2-methyl-5-thiazol-5-yl-phenyl)-pyrazin-2-yl]-isonicotinamide;
3-Methyl-N-[5-(2-methyl-5-thiazol-5-yl-phenyl)-pyrazin-2-yl]-isonicotinamide;
3,5-Difluoro-N-[5-(2-methyl-5-thiazol-5-yl-phenyl)-pyrazin-2-yl]-isonicotinamide;
4-Methyl-[1,2,3]thiadiazole-5-carboxylic acid [5-(2-methyl-5-thiazol-5-yl-phenyl)-pyrazin-2-yl]-amide;
N-[5-(2-Chloro-5-oxazol-5-yl-phenyl)-pyrazin-2-yl]-3-fluoro-isonicotinamide;
N-[5-(2-Chloro-5-oxazol-5-yl-phenyl)-pyrazin-2-yl]-3-methyl-isonicotinamide;
N-[5-(2-Chloro-5-oxazol-5-yl-phenyl)-pyrazin-2-yl]-3,5-difluoro-isonicotinamide;
4-Methyl-[1,2,3]thiadiazole-5-carboxylic acid [5-(2-chloro-5-oxazol-5-yl-phenyl)-pyrazin-2-yl]-amide;
3-Fluoro-N-[5-(5-isoxazol-5-yl-2-methyl-phenyl)-pyrazin-2-yl]-isonicotinamide;
N-[5-(5-Isoxazol-5-yl-2-methyl-phenyl)-pyrazin-2-yl]-3-methyl-isonicotinamide;
3,5-Difluoro-N-[5-(5-isoxazol-5-yl-2-methyl-phenyl)-pyrazin-2-yl]-isonicotinamide;
4-Methyl-[1,2,3]thiadiazole-5-carboxylic acid [5-(5-isoxazol-5-yl-2-methyl-phenyl)-pyrazin-2-yl]-amide;
3-Fluoro-N-[5-(5-isothiazol-5-yl-2-methyl-phenyl)-pyrazin-2-yl]-isonicotinamide;
N-[5-(5-Isothiazol-5-yl-2-methyl-phenyl)-pyrazin-2-yl]-3-methyl-isonicotinamide;
3,5-Difluoro-N-[5-(5-isothiazol-5-yl-2-methyl-phenyl)-pyrazin-2-yl]-isonicotinamide;
4-Methyl-[1,2,3]thiadiazole-5-carboxylic acid [5-(5-isothiazol-5-yl-2-methyl-phenyl)-pyrazin-2-yl]-amide;
N-[5-(2-Chloro-5-isoxazol-5-yl-phenyl)-pyrazin-2-yl]-3-fluoro-isonicotinamide;
N-[5-(2-Chloro-5-isoxazol-5-yl-phenyl)-pyrazin-2-yl]-3-methyl-isonicotinamide;
N-[5-(2-Chloro-5-isoxazol-5-yl-phenyl)-pyrazin-2-yl]-3,5-difluoro-isonicotinamide;
4-Methyl-[1,2,3]thiadiazole-5-carboxylic acid [5-(2-chloro-5-isoxazol-5-yl-phenyl)-pyrazin-2-yl]-amide;
3-{5-[(3-Fluoro-pyridine-4-carbonyl)-amino]-pyrazin-2yl}-4-methyl-benzoic acid methyl ester;
N-[5-(2,5-Dimethoxy-phenyl)-pyrazin-2-yl]-2,6-difluoro-benzamide;

N-[5-(2-Chloro-5-trifluoromethyl-phenyl)-pyrazin-2-yl]-2-methyl-nicotinamide;

Cyclohexanecarboxylic acid [5-(2-chloro-5-trifluoromethyl-phenyl)-pyrazin-2-yl]amide;

N-[5-(2,5-Dimethoxy-phenyl)-pyrazin-2-yl]-3-fluoro-isonicotinamide;

4-Methyl-[1,2,3]thiadiazole-5-carboxylic acid [5-(2-chloro-5-trifluoromethyl-phenyl)-pyrazin-2-yl]-amide;

N-[5-(2-Chloro-5-trifluoromethyl-phenyl)-pyrazin-2-yl]-3,5-difluoro-isonicotinamide;

N-[5-(2,5-Dimethoxy-phenyl)-pyrazin-2-yl]-3-methyl-isonicotinamide;

N-[5-(2,5-Dimethoxy-phenyl)-pyrazin-2-yl]-3,5-difluoro-isonicotinamide;

4-Methyl-[1,2,3]thiadiazole-5-carboxylic acid [5-(2,5-dimethoxy-phenyl)-pyrazin-2-yl]-amide;

Cyclohexanecarboxylic acid [5-(2,5-dimethoxy-phenyl)-pyrazin-2-yl]-amide; and

Cyclohexanecarboxylic acid [5-(2-methyl-5-oxazol-2-yl-phenyl)-pyrazin-2-yl]-amide;

or a pharmaceutically acceptable salt thereof.

10. The method of claim 1, or a pharmaceutically acceptable salt thereof, wherein $R_{12}$ is phenyl or pyridinyl optionally substituted with one or more substituents selected from the group consisting of alkyl, haloalkyl, heteroaryl, a halo, cyano, —$OR_{17}$, —$C(X3)OR_{17}$, and —$C(X3)NR_{15}R_{16}$.

11. The method of claim 1, or a pharmaceutically acceptable salt thereof, wherein $R_{13}$ is phenyl, pyridinyl, [1,2,3]-thiadiazole or cyclohexyl, each of which is optionally substituted with one or more substituents selected from the group consisting of a lower alkyl, a halo, cyano, a lower haloalkyl, and a lower alkoxy.

12. The method of claim 1, or a pharmaceutically acceptable salt thereof, wherein $R_{14}$ is H.

13. The method of claim 1, or a pharmaceutically acceptable salt thereof, wherein n is 0.

14. The method of claim 1, or a pharmaceutically acceptable salt thereof, wherein $R_{15}$ and $R_{16}$, for each occurrence are, independently, H, alkyl, or $R_{15}$ and $R_{16}$ are taken together with the nitrogen to which they are attached to form heterocyclyl or heteroaryl.

15. The method of claim 1, or a pharmaceutically acceptable salt thereof, wherein $R_{17}$ is H, alkyl, or cycloalkyl.

16. The method of claim 1, or a pharmaceutically acceptable salt thereof, wherein $R_{12}$ is phenyl or pyridinyl optionally substituted with one or more substituents selected from the group consisting of alkyl, haloalkyl, heteroaryl, a halo, cyano, —$OR_{17}$, —$C(X3)OR_{17}$, and —$C(X3)NR_{15}R_{16}$;

$R_{13}$ is phenyl, pyridinyl, [1,2,3]-thiadiazole or cyclohexyl, each of which is optionally substituted with one or more substituents selected from the group consisting of a lower alkyl, a halo, cyano, a lower haloalkyl, and a lower alkoxy;

$R_{14}$ is H;

$R_{15}$ and $R_{16}$, for each occurrence are, independently, H, alkyl, or $R_{15}$ and $R_{16}$ are taken together with the nitrogen to which they are attached to form heterocyclyl or heteroaryl;

$R_{17}$ is H, alkyl or cycloalkyl;

$X_3$ is =O; and n is 0.

17. The method of claim 16, or a pharmaceutically acceptable salt thereof, wherein $R_{12}$ is phenyl or pyridinyl optionally substituted with one or more substituents selected from the group consisting of alkyl of 1 to 4 carbon atoms, haloalkyl of 1 to 4 carbon atoms, monocyclic 5- or 6-membered heteroaryl comprising 1 or 2 heteroatoms selected from O and N, cyano, a halo selected from fluoro and chloro, —$OR_{17}$, —$C(X_3)OR_{17}$, and —$C(X_3)NR_{15}R_{16}$;

$R_{13}$ is phenyl or pyridinyl, each of which is optionally substituted with one or more substituents selected from the group consisting of an alkyl of 1 to 4 carbon atoms and a fluoro atom;

$R_{14}$ is H;

$R_{15}$ and $R_{16}$ are H;

$R_{17}$ is H, an alkyl of 1 to 4 carbon atoms or cycloalkyl;

$X_3$ is =O; and n is 0.

18. The method of claim 17, or a pharmaceutically acceptable salt thereof, wherein $R_{12}$ is phenyl, optionally substituted with one or more substituents selected from the group consisting of —$CH_3$, —$CF_3$, chloro, cyano, monocyclic 5-membered heteroaryl comprising 1 or 2 heteroatoms selected from O and N, —$OR_{17}$, —$C(O)OR_{17}$, and —$C(O)NH_2$;

$R_{13}$ is pyridinyl, which is optionally substituted with one or more substituents selected from the group consisting of an alkyl of 1 to 4 carbon atoms and a fluoro atom; and $R_{17}$ is alkyl of 1 to 4 carbon atoms or cycloalkyl.

19. The method of claim 18 for treating organ transplant rejection.

20. The method of claim 18 for treating psoriasis.

21. The method of claim 18 for treating rheumatoid arthritis.

22. The method of claim 18 for treating ulcerative colitis.

23. The method of claim 18 for treating Crohn's disease.

* * * * *